United States Patent
Dean et al.

(10) Patent No.: US 7,381,728 B2
(45) Date of Patent: Jun. 3, 2008

(54) PIPERAZINE DERIVATIVES USEFUL FOR THE TREATMENT OF GASTROINTESTINAL DISORDERS

(75) Inventors: David Kenneth Dean, Harlow (GB); Alessandra Gaiba, Harlow (GB); Nigel Paul King, Harlow (GB); Andrew Kenneth Takle, Harlow (GB); Jason Witherington, Harlow (GB)

(73) Assignee: Glaxo Group Limited, Middlesex (GB)

( * ) Notice: Subject to any disclaimer, the term of this patent is extended or adjusted under 35 U.S.C. 154(b) by 0 days.

(21) Appl. No.: 11/572,715

(22) PCT Filed: Jul. 26, 2005

(86) PCT No.: PCT/EP2005/008263
§ 371 (c)(1),
(2), (4) Date: Jan. 26, 2007

(87) PCT Pub. No.: WO2006/010629
PCT Pub. Date: Feb. 2, 2006

(65) Prior Publication Data
US 2007/0259877 A1 Nov. 8, 2007

(30) Foreign Application Priority Data
Jul. 28, 2004 (GB) .................. 0416844.9
Jul. 8, 2005 (GB) .................. 0514029.8

(51) Int. Cl.
*A61K 31/4965* (2006.01)
*C07D 241/04* (2006.01)
*C07D 295/00* (2006.01)

(52) U.S. Cl. .................. 514/255.03; 544/395
(58) Field of Classification Search .................. None
See application file for complete search history.

(56) References Cited

FOREIGN PATENT DOCUMENTS

| EP | 1 159 964 A2 | 12/2001 |
|---|---|---|
| WO | WO-95/06637 A1 | 3/1995 |
| WO | WO-97/24369 A1 | 7/1997 |
| WO | WO 98/27081 * | 6/1998 |
| WO | WO-98/27081 A1 | 6/1998 |
| WO | WO-99/42465 A2 | 8/1999 |
| WO | WO-00/05225 A1 | 2/2000 |
| WO | WO-01/23374 A1 | 4/2001 |
| WO | WO-01/32660 A1 | 5/2001 |
| WO | WO-02/36562 A2 | 5/2002 |
| WO | WO-02/074764 A2 | 9/2002 |
| WO | WO-02/074768 A1 | 9/2002 |
| WO | WO-03/053925 A1 | 7/2003 |
| WO | WO-2004/073634 A2 | 9/2004 |

OTHER PUBLICATIONS

Asakawa et al., "Ghrelin Is an Appetite-Stimulatory Signal from Stomach with Structural Resemblance to Motilin," *Gastroenterology*, 2001, vol. 120, pp. 337-345.
Date et al., "The Role of the Gastric Afferent Vagal Nerve in Ghrelin-Induced Feeding and Growth Hormone Secretion in Rats," *Gastroenterology*, 2002, vol. 123, pp. 1120-1128.
Kojima et al., "Ghrelin is a Growth-Hormone-Releasing Acylated Peptide from Stomach," *Nature*, 1999, vol. 402, pp. 656-660.
Lu et al., "Immunocytochemical Observation of Ghrelin-Containing Neurons in the Rat Arcuate Nucleus," *Neuroscience Letters*, 2002, vol. 321(3), pp. 157-160.
Masuda et al., "Ghrelin Stimulates Gastric Acid Secretion and Motility in Rats," *Biochemical and Biophysical Research Communications*, 2000, vol. 276, pp. 905-908.
Muccioli et al., "Neuroendocrine and Peripheral Activities of Ghrelin: Implications in Metabolism and Obesity," *Eur. J. Pharmacology*, 2002, vol. 440, pp. 235-254.
Murray et al., "Facilitation by Ghrelin and Metoclopramide of Nerve-Mediated Excitatory Responses in Mouse Gastric Fundus Circular Muscle," *Br. J. Pharmacology*, 2002, vol. 136, Abstract No. 18P.
Nagaya et al., "Hemodynamic, Renal, and Hormonal Effects of Ghrelin Infusion in Patients with Chronic Heart Failure," *J. Clin. Endocrinol. Metab.*, 2001, vol. 86(12), pp. 5854-5859.
Nakazato et al., "A Role for Ghrelin in the Central Regulation of Feeding," *Nature*, 2001, vol. 409, pp. 194-198.
Shintani et al., "Ghrelin, and Endogenous Growth Hormone Secretagogue, Is a Novel Orexigenic Peptide That Antagonizes Leptin Action through the Activation of Hypothalamic Neuropeptide Y/YI Receptor Pathway," *Diabetes*, 2001, vol. 50, pp. 227-232.
Sibilia et al., "Evidence for a Central Inhibitory Role of Growth Hormone Secretagogues and Ghrelin on Gastric Acid Secretion in Conscious Rats," *Neuroendocrinology*, 2002, vol. 75(2), pp. 92-97.
Trudel et al., "Ghrelin/Motilin-Related Peptide is a Potent Prokinetic to Reverse Gastric Postoperative Ileus in Rat," *Am. J. Physiol. Gastrointest. Liver Physiol.*, 2002, vol. 282, pp. G948-G952.
Tschöp et al., "Ghrelin Induces Adiposity in Rodents," *Nature*, 2000, vol. 407(6806), pp. 908-913.

* cited by examiner

*Primary Examiner*—James O. Wilson
*Assistant Examiner*—Erich A. Leeser
(74) *Attorney, Agent, or Firm*—Bonnie L. Deppenbrock

(57) ABSTRACT

The invention provides compounds of formula (I) or pharmaceutically acceptable salts thereof, wherein $R^a$, $R^b$, $R^c$, $R^d$, $R^e$, $R^f$ and Y are as defined in the specification. The compounds are partial or full agonists at the growth hormone secretagogue (GHS) receptors. Pharmaceutical compositions comprising the compounds methods of preparing the compounds, uses of the compounds and methods involving the compounds are also provided.

13 Claims, No Drawings

PIPERAZINE DERIVATIVES USEFUL FOR THE TREATMENT OF GASTROINTESTINAL DISORDERS

CROSS-REFERENCE TO RELATED APPLICATIONS

This application is filed pursuant to 35 USC 371 as a United States National Phase Aplication of International Patent Serial No. PCT/EP2005/008263 filed of Jul. 26, 2005, which claims priority from 0514029.8 filed on Jul. 8, 2005 and from 0416844.9 filed on Jul. 28, 2004 in the United Kingdom.

FIELD OF THE INVENTION

The present invention relates to novel piperazine derivatives, processes for their preparation, pharmaceutical compositions containing the same and to their use in the treatment of gastrointestinal and other disorders.

BACKGROUND OF THE INVENTION

Ghrelin is a 28 amino acid peptide predominantly produced by the stomach and to a lesser extent by the bowel, pancreas, kidney, placenta, pituitary and the arcuate nucleus of the hypothalamus. It has only recently been purified and isolated from the rat and human stomach (Kojima et al., Nature 1999; 402: 656), where it has been found in X/A endocrine cells associated with the acid-secreting parietal cells of the gastric glands. Studies have shown that ghrelin acts on growth hormone secretagogue receptors (GHS-R), stimulates the release of growth hormone, induces rat adiposity (Tschöp et al., Nature 2000, 407(6806), 908), controls gastric acid secretion (Masuda et al., Biochemical and Biophysical Research Communications 2000; 276: 905) and when released within the rodent arcuate nucleus (Kojima et al., Nature 1999; 402: 656; Lu et al., Neuroscience Letters. 2002; 321(3):157) or when administered i.c.v. (Nakazato et al., Nature 2001; 409: 194; Shintani et al., Diabetes 2001;50: 227) stimulates an increase in food consumption. Systemically-administered ghrelin may also achieve the same, possibly by changing vagal nerve input to the brainstem vagal nuclei and hence, to the arcuate nucleus (Date et al., Gastroenterology 2002; 123: 1120). These studies indicate that GHS-R agonists have therapeutic utility in the treatment of different forms of cachexia and eating disorders.

Agonists of the ghrelin receptor have been described as useful in treating a growth hormone deficient state, stimulating an increase in food consumption thereby facilitating weight gain or maintenance of weight or appetite increase. This is particularly useful for a patient having a disease or disorder, or under going a treatment, that is accompanied by weight loss. Examples of diseases or disorders accompanied by weight loss include eating disorders (including anorexia, bulimia) cancer cachexia, AIDS, wasting, cachexia, and wasting in frail elderly. Examples of treatments accompanied by weight loss include chemotherapy, radiation therapy, temporary or permanent immobilization, and dialysis.

Further work with growth hormone secretagogues [e.g., WO 97/24369] suggests roles for ghrelin receptor agonists in the treatment or prevention of frailty associated with ageing, the acceleration of the repair of fractured bone, reducing protein catabolism after major surgery or during chronic illness, improving muscle strength and mobility control of congestive heart failure, and other metabolic disorders. Studies with such compounds also indicate a role in the promotion of sleep quality [WO 97/24369], and in the improvement of congestive heart failure after administration of ghrelin (Nagaya et al., J. Clin. Endocrinol. Metab. 2001, 86, 5854-5859; Circulation 2001, 104, 1430-1435).

In both anaesthetized and conscious rodents and in conscious dogs, ghrelin increases gastric motility and emptying (anaesthetized rat motility Masuda et al., Biochemical and Biophysical Research Communications 2000; 276: 905; rat gastric emptying Trudel et al., American Journal of Physiology 2002; 282: G948; mouse gastric emptying Asakawa et al., Gastroenterology 2001; 120: 337). This action can also be illustrated in vitro, by showing an ability of rat ghrelin to facilitate electrically-evoked, excitatory nerve-mediated contractions in rodent gastric fundus strips, a response mimicked by partial 5-HT$_4$ receptor agonists and indicative of a "prokinetic-like" response (Murray et al., British Journal of Pharmacology 2002; 136: 18P). Further, in conscious rats, i.c.v. administration of ghrelin reduces gastric acid secretion (Sibilia et al, Neuroendocrinology 2002; 75: 92); s.c. administration was without effect. Trudel and colleagues (American Journal of Physiology 2002; 282: G948) showed that ghrelin could reverse the gastric stasis created by invoking paralytic ileus via intestinal manipulation. Together, all of these data indicate that ghrelin might act as a gut hormone to facilitate both nutritional intake and digestion. This concurs with the proposal that the ability of ghrelin to evoke small reductions in pancreatic insulin secretion is consistent with the release of ghrelin during fasting conditions, when it will be important to maintain appropriate levels of blood sugars (see Muccioli et al., Eur J Pharmacology 2002, 440: 235).

Thus, in addition to conditions associated with cachexia (e.g. as a result of cancer), sarcopenia and/or those chronic diseases that may be exacerbated by loss of muscle mass (e.g. osteoporosis, rheumatoid arthritis, osteoarthritis, advancing age), growth hormone deficiency (e.g., when associated with age-related conditions), other disorders of metabolism, disorders in patterns of sleep or of congestive heart failure, GHS-R agonists will be useful treatments to alleviate symptoms associated with gastro-esophageal reflux and/or with dyspepsia, with or without appetite-/metabolic-related cachexia. Examples of such conditions include the reduction in feeding and the gastric stasis and emesis associated with anti-cancer treatment and other treatments or conditions which evoke similar symptoms, the gastroparesis associated with diabetes and gastroparesis and the symptoms associated with functional dyspepsia and gastro-esophageal reflux disease. Further, an ability to stimulate intestinal motility suggests that compounds active at ghrelin receptors will be useful treatments of paralytic ileus or pseudo-obstruction, and of conditions associated with constipation, such as constipation-predominant irritable bowel syndrome.

European patent application EP1159964 claims the use of compounds which stimulate the release of growth hormone as a means of stimulating the motility of the gastrointestinal system in a patient.

WO 95/06637 discloses a series of piperazine derivatives which are said to possess 5-HT$_{1D}$ receptor antagonist activity. WO0236562, WO132660, WO0005225, WO9942465 and WO9827081 all disclose arylpiperazine sulfonamide derivatives that are claimed to be 5-HT$_6$ receptor antagonists. WO0274764, WO0274768, and WO0123374 all disclose dimethylpiperazine derivatives that are claimed to be selective 5HT$_{1B}$ receptor antagonists.

SUMMARY OF THE INVENTION

We have now found a novel class of arylpiperazine sulfonamide derivatives which exhibit a selective agonistic activity at the growth hormone secretagogue (GHS) receptors.

The present invention therefore provides a compound of formula (I) or a pharmaceutically acceptable salt thereof:

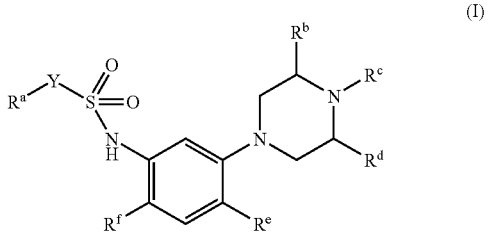

(I)

in which $R^a$ is aryl or heteroaryl;
Y is a single bond, $CH_2$, $CH_2CH_2$, or $CH=CH$;
$R^b$ is hydrogen or $C_{1-6}$alkyl;
$R^c$ is hydrogen or methyl;
$R^d$ is $C_{1-6}$alkyl;
$R^e$ is hydrogen, $C_{1-6}$alkyl, $C_{3-6}$cycloalkyl, $COC_{1-6}$alkyl, $C_{1-6}$alkoxy, halogen, hydroxyl, trifluoromethyl, trifluoromethoxy or cyano; and
$R^f$ is hydrogen, $C_{1-6}$alkyl, $C_{3-6}$cycloalkyl, $COC_{1-6}$alkyl, $C_{1-6}$alkoxy, $C_{1-6}$alkoxyC_{1-6}$alkyl, halogen, hydroxyl, trifluoromethyl, or cyano.

DETAILED DESCRIPTION

Alkyl groups, whether alone or as part of another group, may be straight chain or branched. The term "halogen" is used herein to describe, unless otherwise stated, a group selected from fluorine, chlorine, bromine or iodine.

Suitable $C_{3-6}$cycloalkyl groups include cyclopropyl, cyclobutyl, cyclopentyl and cyclohexyl.

The term "aryl" as a group or part of a group includes phenyl and naphthyl. Where used herein the term naphthyl is intended, unless otherwise stated, to denote both naphth-1-yl and naphth-2-yl groups.

The term "heteroaryl" is intended to mean a 5-6 membered monocyclic aromatic or a fused 8-11 membered bicyclic aromatic ring containing heteroatoms selected from oxygen, nitrogen and sulphur.

When the term heteroaryl represents a 5 or 6 membered group it contains a heteroatom selected from O, N or S and may optionally contain a further 1 to 3 nitrogen atoms. When heteroaryl represents a 6-membered group it contains from 1 to 3 nitrogen atoms.

When the term heteroaryl represents a fused 8-11 membered bicyclic aromatic ring it contains 1 to 3 heteroatoms selected from O, N or S.

Suitable examples of such monocyclic aromatic rings include thienyl, furanyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. The term a fused 8-11 membered bicyclic aromatic group includes groups wherein one of the rings is partially saturated.

Suitable examples of such fused aromatic rings include benzofused heterocyclic rings such as quinolinyl, isoquinolinyl, quinazolinyl, quinoxalinyl, cinnolinyl, naphthyridinyl, indolyl, indazolyl, pyrrolopyridinyl, thienopyridyl, benzofuranyl, benzothienyl, benzimidazolyl, benzoxazolyl, benzisoxazolyl, benzothiazolyl, benzisothiazolyl, benzoxadiazolyl, benzothiadiazolyl, benzodioxanyl, indolinyl, isoindolinyl, tetrahydroquinolinyl, tetrahydroisoquinolinyl, benzazepinyl or chromanyl.

The aryl and heteroaryl groups according to the definitions above included such groups wherein they may be optionally substituted by one to three substituents which may be the same or different, and which are selected from the group consisting of halogen, hydroxy, cyano, nitro, oxo, trifluoromethyl, trifluoromethoxy, fluoromethoxy, difluoromethoxy, $C_{1-6}$ alkyl, $C_{3-6}$ cycloalkyl, Cipentafluoroethyl, $C_{1-6}$ alkoxy, arylC_{1-6}$ alkoxy, $C_{1-6}$ alkylthio, $C_{1-6}$ alkoxyC_{1-6}$ alkyl, $C_{3-7}$ cycloalkylC_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonylC_{1-6}$ alkyl, arylsulfonyl, arylsulfonyloxy, arylsulfonylC_{1-6}$ alkyl, aryloxy, heteroaryloxy, aroyl, aroylC_{1-6}$ alkyl, arylC_{1-6}$ alkanoyl, aryl, heteroaryl, heterocyclyl, or a group $NR^{15}R^{16}$, $CONR^{15}R^{16}$, $SO_2NR^{15}R^{16}$, $NR^{15}COR^{16}$ or $NR^{15}SO_2R^{16}$ wherein $R^{15}$ and $R^{16}$ independently represent hydrogen, $C_{1-6}$ alkyl, $C_{3-7}$ cycloalkyl, aryl, heteroaryl or together with the nitrogen atom to form a 5- to 7-membered non-aromatic heterocyclic ring which may optionally contain an additional ring member selected from O, S or NH.

When $R^a$ is substituted by aryl or heteroaryl groups these substituents are optionally further substituted provided that the further substituents are not aryl or heteroaryl. Further substituents on such aryl and heteroaryl groups may for example be selected from halogen, cyano, $C_{1-6}$alkyl, $C_{1-6}$ alkoxy and oxo. Particularly chloro, cyano, methyl, and oxo. In another aspect, substituents on such aryl and heteroaryl groups may for example be selected from fluoro, methoxy and methoxymethyl The term "heterocyclyl" is intended to mean a 4-7 membered monocyclic saturated or partially unsaturated aliphatic ring containing 1 to 3 heteroatoms selected from oxygen, sulphur or nitrogen. Suitable examples of such monocyclic rings include pyrrolidinyl, piperidinyl, piperazinyl, morpholinyl, thiomorpholinyl, diazepanyl, azepanyl, and tetrahydrofuranyl.

One suitable group of compounds of this invention are of formula (IA): wherein

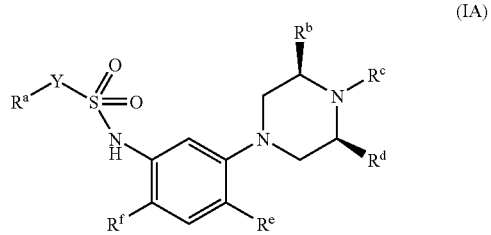

(IA)

$R^a$, $R^b$, $R^c$, $R^d$, $R^e$, $R^f$ and Y are as defined for formula (I).
A suitable group of compounds of formulae (I) and (IA) has:
$R^a$ optionally substituted with one to three substituents selected from $C_{1-6}$alkyl, halogen, dimethylamino, triflouromethyl, optionally substituted aryl or optionally substituted heteroaryl;
Y as a single bond or $CH=CH$;
$R^b$ as hydrogen or methyl;
$R^c$ as hydrogen;

$R^d$ as methyl;
$R^e$ as H, $C_{1-6}$ alkoxy, cyano, halogen or triflouromethoxy; and
$R^f$ as H, $C_{1-6}$ alkoxy cyano, halogen, hydroxyl, $C_{1-6}$ alkoxy$C_{1-6}$ alkyl or $COC_{1-6}$alkyl.

Another suitable group of compounds of formulae (I) and (IA) have:
$R^a$ optionally substituted with one to two substituents selected from $C_{1-6}$alkyl, halogen, oxo, optionally substituted aryl or optionally substituted heteroaryl;
Y as a single bond or CH=CH;
$R^b$ as methyl;
$R^c$ as hydrogen or methyl;
$R^d$ as methyl;
$R^e$ as H or $C_{1-6}$ alkoxy; and
$R^f$ as H, $C_{1-6}$ alkoxy or $COC_{1-6}$alkyl.

A further suitable group of compounds of formulae (I) or (IA) has:
$R^a$ as phenyl, thienyl, benzothiophene, naphthyl, quinolinyl, thienopyridyl, pyridyl, oxazolyl, benzoxazolyl, chromene or benzoxadiazolyl optionally substituted with one to three substituents selected from optionally substituted pyridyl, optionally substituted phenyloxy, chloro, methyl, dimethylamino, optionally substituted thienyl, optionally substituted pyrazolyl, iodo, optionally substituted pyrrolidinyl, optionally substituted isoxazolyl, flouro, bromo, optionally substituted oxazolyl, optionally substituted phenyl, isopropyl, methoxy, optionally substituted furanyl, optionally substituted benzothiophenyl, optionally substituted thiazolyl, trifluoromethyl, optionally substituted pyrazolyl, optionally substituted pyrazinyl, optionally substituted pyrimidinyl and optionally substituted phenylethoxy;
Y as a single bond or CH=CH;
$R^b$ as hydrogen or methyl;
$R^c$ as hydrogen;
$R^d$ as methyl;
$R^e$ as hydrogen, methoxy, cyano, fluoro, ethoxy or triflouromethoxy; and
$R^f$ as hydrogen, methoxy, cyano, fluoro, ethoxy, isopropoxy, hydroxyl, chloro or acetyl.

Another suitable group of compounds of formulae (I) and (IA) have
$R^a$ as phenyl, thienyl, pyridinyl, naphthyl, quinolinyl, benzothiophenyl, or thienopyridinyl optionally substituted with one to two substituents selected from methyl, chloro, cyano, iodo, oxo, dimethylamino, optionally substituted phenoxy, optionally substituted phenyl, optionally substituted pyridinyl, optionally substituted thienyl, optionally substituted pyrozolyl or optionally substituted pyrrolidinyl;
Y as a single bond or CH=CH;
$R^b$ as methyl;
$R^c$ as hydrogen;
$R^d$ as methyl;
$R^e$ as H or methoxy; and
$R^f$ as H, methoxy or acetyl.

Another suitable group of compounds of formulae (I) and (IA) have:
$R^a$ as phenyl, thienyl, or naphthyl optionally substituted with one to two substituents selected from chloro, optionally substituted thienyl, flouro, optionally substituted phenyl and optionally substituted furanyl;
Y as a single bond;
$R^b$ as methyl;
$R^c$ as hydrogen;
$R^d$ as methyl;
$R^e$ as hydrogen; and
$R^f$ as methoxy.

A further suitable group of compounds of formulae (I) or (IA) has:
$R^a$ as phenyl optionally substituted with one to two substituents selected from, flouro and optionally substituted furanyl,
Y as a single bond;
$R^b$ as methyl;
$R^c$ as hydrogen;
$R^d$ as methyl;
$R^e$ as hydrogen; and
$R^f$ as methoxy.

Specific examples of formula (I) are:
N-[3-(cis-3,5-Dimethyl-1-piperazinyl)-4-(methyloxy)phenyl]-5-(2-pyridinyl)-2-thiophenesulfonamide
4-[(3-Chloro-2-cyanophenyl)oxy]-N-[3-(cis-3,5-dimethyl-1-piperazinyl)-4-(methyloxy)phenyl]benzenesulfonamide
5-Chloro-N-[3-(cis-3,5-dimethyl-1-piperazinyl)-4-(methyloxy)phenyl]-3-methyl-1-benzothiophene-2-sulfonamide
5-(Dimethylamino)-N-[3-(cis-3,5-dimethyl-1-piperazinyl)-4-(methyloxy)phenyl]-1-naphthalenesulfonamide
N-[3-(cis-3,5-Dimethyl-1-piperazinyl)-4-(methyloxy)phenyl]-1-naphthalenesulfonamide
(E)-N-[3-(cis-3,5-Dimethyl-1-piperazinyl)-4-(methyloxy)phenyl]-2-phenylethenesulfonamide
5-Chloro-N-[3-(cis-3,5-dimethyl-1-piperazinyl)-4-(methyloxy)phenyl]-1-benzothiophene-2-sulfonamide
N-[3-(cis-3,5-Dimethyl-1-piperazinyl)-4-(methyloxy)phenyl]-4-(phenyloxy)benzenesulfonamide
N-[3-(cis-3,5-Dimethyl-1-piperazinyl)-4-(methyloxy)phenyl]-8-quinolinesulfonamide
N-[3-(cis-3,5-Dimethyl-1-piperazinyl)-4-(methyloxy)phenyl]thieno[2,3-b]pyridine-2-sulfonamide
N-[3-(cis-3,5-Dimethyl-1-piperazinyl)-4-(methyloxy)phenyl]-4-(2-thienyl)benzenesulfonamide
8-Chloro-N-[3-[(cis-3,5-dimethyl-1-piperazinyl)-4-(methyloxy)phenyl]-1-naphthalenesulfonamide
N-[5-(cis-3,5-Dimethyl-1-piperazinyl)-2-(methyloxy)phenyl]-5-(2-pyridinyl)-2-thiophenesulfonamide
4-[(3-Chloro-2-cyanophenyl)oxy]-N-[5-(cis-3,5-dimethyl-1-piperazinyl)-2-(methyloxy)phenyl]benzenesulfonamide
N-[5-(cis-3,5-Dimethyl-1-piperazinyl)-2-(methyloxy)phenyl]-4-(1H-pyrazol-1-yl)benzenesulfonamide
5-Chloro-N-[5-(cis-3,5-dimethyl-1-piperazinyl)-2-(methyloxy)phenyl)-3-methyl-1-benzothiophene-2-sulfonamide
N-[5-(cis-3,5-Dimethyl-1-piperazinyl)-2-(methyloxy)phenyl]-4-(2-thienyl)benzenesulfonamide
N-[3-(cis-3,5-Dimethyl-1-piperazinyl)-4-(methyloxy)phenyl]-2-naphthalenesulfonamide
N-[3-(cis-3,5-Dimethyl-1-piperazinyl)-4-(methyloxy)phenyl]-4-(1H-pyrazol-1-yl)benzenesulfonamide
N-[3-(cis-3,5-Dimethyl-1-piperazinyl)-4-(methyloxy)phenyl]-6-(3-thienyl)-2-pyridinesulfonamide
N-[3-(cis-3,5-Dimethyl-1-piperazinyl)-4-(methyloxy)phenyl]-5-(6-methyl-2-pyridinyl)-2-thiophenesulfonamide
N-[3-cis-3,5-Dimethyl-1-piperazinyl)-4-(methyloxy)phenyl]-4-iodobenzenesulfonamide
N-[3-(cis-3,5-Dimethyl-1-piperazinyl)-4-(methyloxy)phenyl]-4-(2-oxo-1-pyrrolidinyl)benzenesulfonamide
N-[2-Acetyl-5-(cis-3,5-dimethyl-1-piperazinyl)phenyl]-4-[(3-chloro-2-cyanophenyl)oxy]benzenesulfonamide
N-[2-Acetyl-5-(cis-3,5-dimethyl-1-piperazinyl)phenyl]-5-(2-pyridinyl)-2-thiophenesulfonamide N-[2-Acetyl-5-(cis-3,5-dimethyl-1-piperazinyl)phenyl]-4-(2-thienyl)benzenesulfonamide N-[2-Acetyl-5-(cis-3,5-dimethyl-1-piperazinyl)phenyl]-4-(1H-pyrazol-1-yl)benzenesulfonamide.

N-[3-(cis-3,5-Dimethyl-1-piperazinyl)-4-(methyloxy)phenyl]-3,5-dimethyl-4-isoxazolesulfonamide 2,3-Dichloro-N-[3-(cis-3,5-dimethyl-1-piperazinyl)-4-(methyloxy)phenyl]benzenesulfonamide 3,4-Dichloro-N-[3-(cis-3,5-dimethyl-1-piperazinyl)-4-(methyloxy)phenyl]benzenesulfonamide N-[5-(cis-3,5-Dimethyl-1-piperazinyl)-2-(methyloxy)phenyl]-2-naphthalenesulfonamide N-[5-(cis-3,5-Dimethyl-1-piperazinyl)-2-(methyloxy)phenyl]-1-naphthalenesulfonamide N-[5-(cis-3,5-Dimethyl-1-piperazinyl)-2-(methyloxy)phenyl]-4-(phenyloxy)benzenesulfonamide N-[5-(cis-3,5-Dimethyl-1-piperazinyl)-2-(methyloxy)phenyl]-4-iodobenzenesulfonamide N-[5-(cis-3,5-Dimethyl-1-piperazinyl)-2-(methyloxy)phenyl]-8-quinolinesulfonamide 3,4-Dichloro-N-[5-(cis-3,5-dimethyl-1-piperazinyl)-2-(methyloxy)phenyl]benzenesulfonamide 2,3-Dichloro-N-[5-(cis-3,5-dimethyl-1-piperazinyl)-2-(methyloxy)phenyl]benzenesulfonamide (E)-N-[5-(cis-3,5-Dimethyl-1-piperazinyl)-2-(methyloxy)phenyl]-2-phenylethenesulfonamide N-[4-Cyano-3-(cis-3,5-dimethyl-1-piperazinyl)phenyl]-4-(2-thienyl)benzenesulfonamide N-[5-(cis-3,5-Dimethyl-1-piperazinyl)-2-(methyloxy)phenyl]-5-fluoro-3-methyl-1-benzothiophene-2-sulfonamide 5'-Chloro-N-[5-(cis-3,5-dimethyl-1-piperazinyl)-2-(methyloxy)phenyl]-2,2'-bithiophene-5-sulfonamide 2-Bromo-N-[5-(cis-3,5-dimethyl-1-piperazinyl)-2-(methyloxy)phenyl]benzenesulfonamide N-[3-(cis-3,5-Dimethyl-1-piperazinyl)-4-(methyloxy)phenyl]-5-(1,3-oxazol-5-yl)-2-tbiophenesulfonamide N-[3-(cis-3,5-Dimethyl-1-piperazinyl)phenyl]-4-(2-thienyl)benzenesulfonamide 4-(5-Chloro-2-thienyl)-N-[3-(cis-3,5-dimethyl-1-piperazinyl)phenyl]benzenesulfonamide N-[3-(cis-3,5-Dimethyl-1-piperazinyl)phenyl]-4-(1H-pyrazol-1-yl)benzenesulfonamide 5-Chloro-N-[3-(cis-3,5-dimethyl-1-piperazinyl)-4-(methyloxy)phenyl]-2-naphthalenesulfonamide N-[3-(cis-3,5-Dimethyl-1-piperazinyl)-4-(methyloxy)phenyl]-4-biphenylsulfonamide 4-Bromo-N-[3-(cis-3,5-dimethyl-1-piperazinyl)-4-(methyloxy)phenyl]-3-methylbenzenesulfonamide 4-Bromo-N-[3-(cis-3,5-dimethyl-1-piperazinyl)-4-(methyloxy)phenyl]-3-fluorobenzenesulfonamide 4-Bromo-2-chloro-N-[3-(cis-3,5-dimethyl-1-piperazinyl)-4-(methyloxy)phenyl]benzenesulfonamide 4-Bromo-N-[3-(cis-3,5-dimethyl-1-piperazinyl)-4-(methyloxy)phenyl]-2-fluorobenzenesulfonamide N-[5-(cis-3,5-Dimethyl-1-piperazinyl)-4-fluoro-2-(methyloxy)phenyl]-4-(2-thienyl)benzenesulfonamide N-[5-(cis-3,5-Dimethyl-1-piperazinyl)-4-fluoro-2-(methyloxy)phenyl]-5-(2-pyridinyl)-2-thiophenesulfonamide 5-Chloro-N-[5-(cis-3,5-dimethyl-1-piperazinyl)-2-(methyloxy)phenyl]-1-benzothiophene-2-sulfonamide N-[5-(cis-3,5-Dimethyl-1-piperazinyl)-2-(methyloxy)phenyl]-4-(1,3-oxazol-5-yl)benzenesulfonamide N-[3-(cis-3,5-Dimethyl-1-piperazinyl)-4-(methyloxy)phenyl]-4-(1,3-oxazol-5-yl)benzenesulfonamide N-[3-(cis-3,5-Dimethyl-1-piperazinyl)-4-(methyloxy)phenyl]-4-methyl-3,4-dihydro-2H-1,4-benzoxazine-7-sulfonamide N-[3-(cis-3,5-Dimethyl-1-piperazinyl)-4-(methyloxy)phenyl]-4-(1-methylethyl)benzenesulfonamide N-[5-(cis-3,5-Dimethyl-1-piperazinyl)-2-(methyloxy)phenyl]-3-{[4-(methyloxy)phenyl]oxy}benzenesulfonamide N-[5-(cis-3,5-Dimethyl-1-piperazinyl)-2-(methyloxy)phenyl]1-benzothiophene-3-sulfonamide N-[5-(cis-3,5-Dimethyl-1-piperazinyl)-2-(methyloxy)phenyl]-5-(1,3-oxazol-5-yl)-2-thiophenesulfonamide N-[5-(cis-3,5-Dimethyl-1-piperazinyl)-2-(methyloxy)phenyl]-4-biphenylsulfonamide N-[3-(cis-3,5-Dimethyl-1-piperazinyl)phenyl]-1-naphthalenesulfonamide N-[3-(cis-3,5-Dimethyl-1-piperazinyl)phenyl]-2-naphthalenesulfonamide 2,3-Dichloro-N-[3-(cis-3,5-dimethyl-1-piperazinyl)phenyl]benzenesulfonamide N-[3-(cis-3,5-Dimethyl-1-piperazinyl)phenyl]-1-benzothiophene-2-sulfonamide N-[3-(cis-3,5-Dimethyl-1-piperazinyl)phenyl]-4-(1,3-oxazol-5-yl)benzenesulfonamide N-[5-(cis-3,5-Dimethyl-1-piperazinyl)-2-methylphenyl]-2-naphthalenesulfonamide N-[5-(cis-3,5-Dimethyl-1-piperazinyl)-2-methylphenyl]-1-naphthalenesulfonamide 8-Chloro-N-[5-(cis-3,5-dimethyl-1-piperazinyl)-2-(methyloxy)phenyl]-1-naphthalenesulfonamide 4-Bromo-N-[3-(cis-3,5-dimethyl-1-piperazinyl)-4-(methyloxy)phenyl]-2-methylbenzenesulfonamide 4-Bromo-N-[5-(cis-3,5-dimethyl-1-piperazinyl)-2-(methyloxy)phenyl]-3-methylbenzenesulfonamide 5-Bromo-N-[3-(cis-3,5-dimethyl-1-piperazinyl)-4-(methyloxy)phenyl]-2-thiophenesulfonamide 4-Chloro-N-[5-(cis-3,5-dimethyl-1-piperazinyl)-2-(methyloxy)phenyl]-1-naphthalenesulfonamide 3-Bromo-N-[5-(cis-3,5-dimethyl-1-piperazinyl)-2-(methyloxy)phenyl]benzenesulfonamide 5-Bromo-N-[5-(cis-3,5-dimethyl-1-piperazinyl)-2-(methyloxy)phenyl]-2-(methyloxy)benzenesulfonamide 5-Bromo-N-[5-(cis-3,5-dimethyl-1-piperazinyl)-2-(methyloxy)phenyl]-4-methyl-2-thiophenesulfonamide N-[5-(cis-3,5-Dimethyl-1-piperazinyl)-2-(methyloxy)phenyl]-5-(1,2,3-thiadiazol-4-yl)-2-thiophenesulfonamide N-[5-(cis-3,5-Dimethyl-1-piperazinyl)-2-(methyloxy)phenyl]-2,2-dimethyl-3,4-dihydro-2H-chromene-6-sulfonamide 4-Bromo-N-[5-(cis-3,5-dimethyl-1-piperazinyl)-2-methylphenyl]benzenesulfonamide 4-Bromo-N-[3-(cis-3,5-dimethyl-1-piperazinyl)-4-(methyloxy)phenyl]-2-(methyloxy)benzenesulfonamide N-[5-(cis-3,5-Dimethyl-1-piperazinyl)-2-fluorophenyl]-5-(2-pyridinyl)-2-thiophenesulfonamide N-[5-(cis-3,5-Dimethyl-1-piperazinyl)-2-fluorophenyl]-4-biphenylsulfonamide N-[5-(cis-3,5-Dimethyl-1-piperazinyl)-2-fluorophenyl]-4-iodobenzenesulfonamide 4-Bromo-N-[5-(cis-3,5-dimethyl-1-piperazinyl)-2-fluorophenyl]-2-fluorobenzenesulfonamide 4-Bromo-2-chloro-N-[5-(cis-3,5-dimethyl-1-piperazinyl)-2-fluorophenyl]benzenesulfonamide 4-Bromo-N-[5-(cis-3,5-dimethyl-1-piperazinyl)-2-fluorophenyl]-2-methylbenzenesulfonamide 4-Bromo-N-[5-(cis-3,5-dimethyl-1-piperazinyl)-2-fluorophenyl]-3-fluorobenzenesulfonamide N-[5-(cis-3,5-Dimethyl-1-piperazinyl)-2-fluoro-4-(methyloxy)phenyl]-4-iodobenzenesulfonamide N-[5-(cis-3,5-Dimethyl-1-piperazinyl)-2-(ethyloxy)phenyl]-5-(2-pyridinyl)-2-thiophenesulfonamide N-{5-(cis-3,5-Dimethyl-1-piperazinyl)-2-[(methyloxy)methyl]phenyl}-4-biphenylsulfonamide 7-Chloro-N-[5-(cis-3,5-dimethyl-1-piperazinyl)-2-(methyloxy)phenyl]-2,1,3-benzoxadiazole-4-sulfonamide N-[3-(cis-3,5-Dimethyl-1-piperazinyl)-4-(ethyloxy)phenyl]-4-iodobenzenesulfonamide 4-(5-Chloro-2-thienyl)-N-[5-(cis-3,5-dimethyl-1-piperazinyl)-2-(methyloxy)phenyl]benzenesulfonamide 4-(5-Chloro-2-thienyl)-N-[2-cyano-5-(cis-3,5-dimethyl-1-piperazinyl)phenyl]benzenesulfonamide N-[2-Cyano-5-(cis-3,5-dimethyl-1-piperazinyl)phenyl]-4-(2-thienyl)benzenesulfonamide 4-(5-Chloro-2-thienyl)-N-[5-(cis-3,5-dimethyl-1-piperazinyl)-4-fluoro-2-(methyloxy)phenyl]benzenesulfonamide N-[5-(cis-3,5-Dimethyl-1-piperazinyl)-2-(ethyloxy)phenyl]-4-iodobenzenesulfonamide N-{5-(cis-3,5-Dimethyl-1-piperazinyl)-2-[(1-methylethyl)oxy]phenyl}-4-iodobenzenesulfonamide 4-Bromo-N-[3-(cis-3,5-dimethyl-1-piperazinyl)-4-(methyloxy)phenyl]benzenesulfonamide 4-Bromo-N-[5-(cis-3,5-dimethyl-1-piperazinyl)-2-(methyloxy)phenyl]-2-methylbenzenesulfonamide 4-Bromo-N-[5-(cis-3,5-dimethyl-1-piperazinyl)-2-(methyloxy)phenyl]-2-fluorobenzenesulfonamide 4-Bromo-2-chloro-N-[5-(cis-3,5-dimethyl-1-piperazinyl)-2-(methyloxy)phenyl]benzenesulfonamide 4-Bromo-N-[5-(cis-3,5-dimethyl-1-piperazinyl)-2-(methyloxy)phenyl]-3-fluorobenzenesulfonamide 4-Bromo-N-[5-(cis-3,5-dimethyl-1-piperazinyl)-2-(methyloxy)phenyl]benzenesulfonamide N-[5-(cis-3,5-Dimethyl-1-piperazinyl)-2-(methyloxy)phenyl]-4-(4-methyl-2-thienyl)benzenesulfonamide N-[5-(cis-3,5-Dimethyl-1-piperazinyl)-2-(methyloxy)phenyl]-2-methyl-4-(4-methyl-2-thienyl)benzenesulfonamide N-[5-(cis-3,5-Dimethyl-1-piperazinyl)-2-(methyloxy)phenyl]-4-(2-furanyl)benzenesulfonamide N-[5-(cis-3,5-Dimethyl-1-piperazinyl)-2-(methyloxy)phenyl]-2-fluoro-4-(4-methyl-2-thienyl)benzenesulfonamide 3'-Chloro-N-[5-(cis-3,5-dimethyl-1-piperazinyl)-2-(methyloxy)phenyl]-4-biphenylsulfonamide N-[5-(cis-3,5-Dimethyl-1-piperazinyl)-2-(methyloxy)phenyl]-2-fluoro-4-(2-furanyl)benzenesulfonamide 2-Chloro-N-[5-(cis-3,5-dimethyl-1-piperazinyl)-2-(methyloxy)phenyl]-4-(4-methyl-2-thienyl)benzenesulfonamide N-[5-(cis-3,5-Dimethyl-1-piperazinyl)-2-(methyloxy)phenyl]-3-fluoro-4-(2-thienyl)benzenesulfonamide N-[5-(cis-3,5-Dimethyl-1-piperazinyl)-2-(methyloxy)phenyl]-3-fluoro-4-(4-methyl-2-thienyl)benzenesulfonamide N-[5-(cis-3,5-Dimethyl-1-piperazinyl)-2-(methyloxy)phenyl]-3-fluoro-4-(3-furanyl)benzenesulfonamide N-[5-(cis-3,5-Dimethyl-1-piperazinyl)-2-(methyloxy)phenyl]-3'-[(methyloxy)methyl]-4-biphenylsulfonamide N-[5-(cis-3,5-Dimethyl-1-piperazinyl)-2-(methyloxy)phenyl]-4-(3-furanyl)benzenesulfonamide N-[5-(cis-3,5-Dimethyl-1-piperazinyl)-2-(methyloxy)phenyl]-4-(3-thienyl)benzenesulfonamide N-[5-(cis-3,5-Dimethyl-1-piperazinyl)-2-hydroxyphenyl]-5-(2-pyridinyl)-2-thiophenesulfonamide N-[5-(cis-3,5-Dimethyl-1-piperazinyl)-2-(methyloxy)phenyl]-4-(2-oxo-1-pyrrolidinyl)benzenesulfonamide 5-Bromo-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-{3-[(methyloxy)methyl]phenyl}-2-thiophenesulfonamide N-[5-(cis-3,5-Dimethyl-1-piperazinyl)-2-(methyloxy)phenyl]-5-(2-fluorophenyl)-2-thiophenesulfonamide 5-Chloro-N-[5-(cis-3,5-dimethyl-1-piperazinyl)-2-(methyloxy)phenyl]-2-naphthalenesulfonamide N-[5-(cis-3,5-Dimethyl-1-piperazinyl)-2-(methyloxy)phenyl]-4-(6-methyl-2-pyridinyl)benzenesulfonamide N-[5-(cis-3,5-Dimethyl-1-piperazinyl)-2-(methyloxy)phenyl]-5-(6-methyl-2-pyridinyl)-2-thiophenesulfonamide N-[3-(cis-3,5-Dimethyl-1-piperazinyl)-4-(methyloxy)phenyl]-4-(6-methyl-2-pyridinyl)benzenesulfonamide N-[5-(cis-3,5-Dimethyl-1-piperazinyl)-2-(methyloxy)phenyl]-4-(3-pyridinyl)benzenesulfonamide N-[5-(cis-3,5-Dimethyl-1-piperazinyl)-2-(methyloxy)phenyl]-2,2'-bithiophene-5-sulfonamide N-[5-(cis-3,5-Dimethyl-1-piperazinyl)-2-(methyloxy)phenyl]-3-(2-thienyl)benzenesulfonamide N-[3-(cis-3,5-Dimethyl-1-piperazinyl)-4-(methyloxy)phenyl]-4-(3-thienyl)benzenesulfonamide 4-(1-Benzothien-3-yl)-N-[5-(cis-3,5-dimethyl-1-piperazinyl)-2-(methyloxy)phenyl]benzenesulfonamide N-[3-(cis-3,5-Dimethyl-1-piperazinyl)-4-(methyloxy)phenyl]-2,3'-bithiophene-5-sulfonamide N-[3-(cis-3,5-Dimethyl-1-piperazinyl)-4-(methyloxy)phenyl]-5-phenyl-2-thiophenesulfonamide 5-(1-Benzothien-3-yl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-[4-(methyloxy)-3-pyridinyl]-2-thiophenesulfonamide N-[3-(cis-3,5-Dimethyl-1-piperazinyl)-4-(methyloxy)phenyl]-2,2'-bithiophene-5-sulfonamide N-[5-(cis-3,5-Dimethyl-1-piperazinyl)-2-(methyloxy)phenyl]-2'-(ethyloxy)-4-biphenylsulfonamide N-[3-(cis-3,5-Dimethyl-1-piperazinyl)-4-(methyloxy)phenyl]-4'-fluoro-2'-methyl-4-biphenylsulfonamide N-[3-(cis-3,5-Dimethyl-1-piperazinyl)-4-(methyloxy)phenyl]-2'-fluoro-4-biphenylsulfonamide N-[5-(cis-3,5-Dimethyl-1-piperazinyl)-2-(methyloxy)phenyl]-2,3'-bithiophene-5-sulfonamide N-[3-(cis-3,5-Dimethyl-1-piperazinyl)-4-(methyloxy)phenyl]-2-methyl-4-(2-thienyl)benzenesulfonamide N-[3-(cis-3,5-Dimethyl-1-piperazinyl)-4-(methyloxy)phenyl]-2-methyl-4-(6-methyl-2-pyridinyl)benzenesulfonamide 3'-Chloro-N-[3-(cis-3,5-dimethyl-1-piperazinyl)-4-(methyloxy)phenyl]-4'-fluoro-4-biphenylsulfonamide N-[3-(cis-3,5-Dimethyl-1-piperazinyl)-4-(methyloxy)phenyl]-3',5'-difluoro-4-biphenylsulfonamide N-[3-(cis-3,5-Dimethyl-1-piperazinyl)-4-(methyloxy)phenyl]-3'-fluoro-4-biphenylsulfonamide N-[3-(cis-3,5-Dimethyl-1-piperazinyl)-4-(methyloxy)phenyl]-3',4'-difluoro-4-biphenylsulfonanide N-[3-(cis-3,5-Dimethyl-1-piperazinyl)-4-(methyloxy)phenyl]-2',6'-dimethyl-4-biphenylsulfonamide N-[3-(cis-3,5-Dimethyl-1-piperazinyl)-4-(methyloxy)phenyl]-4'-fluoro-4-biphenylsulfonamide N-[3-(cis-3,5-Dimethyl-1-piperazinyl)-4-(methyloxy)phenyl]-4'-methyl-4-biphenylsulfonamide N-[3-(cis-3,5-Dimethyl-1-piperazinyl)-4-(methyloxy)phenyl]-2',3'-difluoro-4-biphenylsulfonamide N-[3-(cis-3,5-Dimethyl-1-piperazinyl)-4-(methyloxy)phenyl]-3'-methyl-4-biphenylsulfonamide 2'-Chloro-N-[5-(cis-3,5-dimethyl-1-piperazinyl)-2-(methyloxy)phenyl]-4-biphenylsulfonamide N-[5-(cis-3,5-Dimethyl-1-piperazinyl)-2-(methyloxy)phenyl]-2-methyl-4-(2-thienyl)benzenesulfonamide N-[3-(cis-3,5-Dimethyl-1-piperazinyl)-4-(methyloxy)phenyl]-3'-[(methyloxy)methyl]-4-biphenylsulfonamide N-[5-(cis-3,5-Dimethyl-1-piperazinyl)-2-(methyloxy)phenyl]-2-fluoro-4-(2-thienyl)benzenesulfonamide N-[3-(cis-3,5-Dimethyl-1-piperazinyl)-4-(methyloxy)phenyl]-2-methyl-4-(4-methyl-2-thienyl)benzenesulfonamide N-[5-(cis-3,5-Dimethyl-1-piperazinyl)-2-(methyloxy)phenyl]-4-(5-methyl-2-thienyl)benzenesulfonamide N-[3-(cis-3,5-Dimethyl-1-piperazinyl)-4-(methyloxy)phenyl]-3-fluoro-4-(2-thienyl)benzenesulfonamide 2-Chloro-N-[3-(cis-3,5-dimethyl-1-piperazinyl)-4-(methyloxy)phenyl]-4-(4-methyl-2-thienyl)benzenesulfonamide N-[5-(cis-3,5-Dimethyl-1-piperazinyl)-2-(methyloxy)phenyl]-4-(4-methyl-3-thienyl)benzenesulfonamide N-[5-(cis-3,5-Dimethyl-1-piperazinyl)-2-(methyloxy)phenyl]-4-(3-furanyl)-2-methylbenzenesulfonamide N-[3-(cis-3,5-Dimethyl-1-piperazinyl)-4-(methyloxy)phenyl]-4-(3-furanyl)-2-methylbenzenesulfonamide N-[5-(cis-3,5-Dimethyl-1-piperazinyl)-2-(methyloxy)phenyl]-2-fluoro-4-(3-furanyl)benzenesulfonamide N-[5-(cis-3,5-Dimethyl-1-piperazinyl)-2-(methyloxy)phenyl]-2-fluoro-4-(6-methyl-2-pyridinyl)benzenesulfonamide 2-Chloro-N-[5-(cis-3,5-dimethyl-1-piperazinyl)-2-(methyloxy)phenyl]-4-(6-methyl-2-pyridinyl)benzenesulfonamide N-[5-(cis-3,5-Dimethyl-1-piperazinyl)-2-(methyloxy)phenyl]-2-fluoro-4-(3-thienyl)benzenesulfonamide N-[3-(cis-3,5-Dimethyl-1-piperazinyl)-4-(methyloxy)phenyl]-3-methyl-4-(2-thienyl)benzenesulfonamide N-[3-(cis-3,5-Dimethyl-1-piperazinyl)-4-(methyloxy)phenyl]-2-fluoro-4-(2-thienyl)benzenesulfonamide N-[3-(cis-3,5-Dimethyl-1-piperazinyl)-4-(methyloxy)phenyl]-2-fluoro-4-(6-methyl-2-pyridinyl)benzenesulfonamide 2-Chloro-N-[3-(cis-3,5-dimethyl-1-piperazinyl)-4-(methyloxy)phenyl]-4-(6-methyl-2-pyridinyl)benzenesulfonamide N-[5-(cis-3,5-Dimethyl-1-piperazinyl)-2-methylphenyl]-4-(2-thienyl)benzenesulfonamide N-[5-(cis-3,5-Dimethyl-1-piperazinyl)-2-methylphenyl]-4-(4-methyl-2-thienyl)benzenesulfonamide N-[5-(cis-3,5-Dimethyl-1-piperazinyl)-2-(methyloxy)phenyl]-3-methyl-4-(2-thienyl)benzenesulfonamide N-[5-(cis-3,5-Dimethyl-1-piperazinyl)-2-(methyloxy)phenyl]-3-methyl-4-(4-methyl-2-thienyl)benzenesulfonamide N-[3-(cis-3,5-Dimethyl-1-piperazinyl)-4-(methyloxy)phenyl]-4-(4-methyl-2-thienyl)benzenesulfonamide N-[5-(cis-3,5-Dimethyl-1-piperazinyl)-2-(methyloxy)phenyl]-2-methyl-4-(6-methyl-2-pyridinyl)benzenesulfonamide N-[5-(cis-3,5-Dimethyl-1-piperazinyl)-2-(methyloxy)phenyl]-3-methyl-4-(3-thienyl)benzenesulfonamide N-[5-(cis-3,5-Dimethyl-1-piperazinyl)-2-(methyloxy)phenyl]-4-(2-furanyl)-2-methylbenzenesulfonamide N-[5-(cis-3,5-Dimethyl-1-piperazinyl)-2-(methyloxy)phenyl]-2-(methyloxy)-5-(4-methyl-2-thienyl)benzenesulfonamide 2-Chloro-N-[5-(cis-3,5-dimethyl-1-piperazinyl)-2-(methyloxy)phenyl]-4-(2-thienyl)benzenesulfonamide 2-Chloro-N-[5-(cis-3,5-dimethyl-1-piperazinyl)-2-(methyloxy)phenyl]-4-(3-furanyl)benzenesulfonamide N-[5-(cis-3,5-Dimethyl-1-piperazinyl)-2-(methyloxy)phenyl]-4-(3-furanyl)-3-methylbenzenesulfonamide N-[3-(cis-3,5-Dimethyl-1-piperazinyl)-4-(methyloxy)phenyl]-4-(3-furanyl)benzenesulfonamide N-[5-(cis-3,5-Dimethyl-1-piperazinyl)-2-(methyloxy)phenyl]-2'-fluoro-4-biphenylsulfonamide 3'-Chloro-N-[5-(cis-3,5-dimethyl-1-piperazinyl)-2-(methyloxy)phelyl]-4'-fluoro-4-biphenylsulfonamide N-[5-(cis-3,5-Dimethyl-1-piperazinyl)-2-(methyloxy)phenyl]-2',3'-difluoro-4-biphenylsulfonamide 5'-Chloro-N-[5-(cis-3,5-dimethyl-1-piperazinyl)-2-(methyloxy)phenyl]-2'-(methyloxy)-4-biphenylsulfonamide N-[5-(cis-3,5-Dimethyl-1-piperazinyl)-2-(methyloxy)phenyl]-3'-methyl-4-biphenylsulfonamide N-[5-(cis-3,5-Dimethyl-1-piperazinyl)-2-(methyloxy)phenyl]-3-fluoro-4-(6-methyl-2-pyridinyl)benzenesulfonamide N-[5-(cis-3,5-Dimethyl-1-piperazinyl)-2-(methyloxy)phenyl]-5-(2-fluorophenyl)-4-methyl-2-thiophenesulfonamide N-[5-(cis-3,5-Dimethyl-1-piperazinyl)-2-(methyloxy)phenyl]-4-methyl-5-(6-methyl-2-pyridinyl)-2-thiophenesulfonamide N-[5-(cis-3,5-Dimethyl-1-piperazinyl)-2-(methyloxy)phenyl]-4-methyl-5-{3-[(methyloxy)methyl]phenyl}-2-thiophenesulfonamide N-[5-(cis-3,5-Dimethyl-1-piperazinyl)-2-(ethyloxy)phenyl]-4-(2-thienyl)benzenesulfonamide N-{5-(cis-3,5-Dimethyl-1-piperazinyl)-2-[(1-methylethyl)oxy]phenyl}-4-(2-thienyl)benzenesulfonamide N-[5-(cis-3,5-Dimethyl-1-piperazinyl)-2-(methyloxy)phenyl]-5-phenyl-2-thiophenesulfonamide 5-(2,4-Difluorophenyl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-[2-(ethyloxy)phenyl]-2-thiophenesulfonamide N-[5-(cis-3,5-Dimethyl-1-piperazinyl)-2-(methyloxy)phenyl]-4'-methyl-2,2'-bithiophene-5-sulfonamide 5-(3-Chloro-4-fluorophenyl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-(2-methylphenyl)-2-thiophenesulfonamide 5-(2,6-Dimethylphenyl)-N-[5-(cis-3,5-dimethyl-1-piperazinyl)-2-(methyloxy)phenyl]-2-thiophenesulfonamide 5-[5-Chloro-2-(methyloxy)phenyl]-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-(3-methylphenyl)-2-thiophenesulfonamide N-[5-(cis-3,5-Dimethyl-1-piperazinyl)-2-(methyloxy)phenyl]-5-(4-fluorophenyl)-2-thiophenesulfonamide N-[5-(cis-3,5-Dimethyl-1-piperazinyl)-2-(methyloxy)phenyl]-5-(4-fluoro-2-methylphenyl)-2-thiophenesulfonamide 5-(2-Chlorophenyl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-(3-fluorophenyl)-2-thiophenesulfonamide N-[5-(cis-3,5-Dimethyl-1-piperazinyl)-2-(methyloxy)phenyl]-5-(4-methylphenyl)-2-thiophenesulfonamide 5-(3-Chlorophenyl)-N-[5-(cis-3,5-dimethyl-1-piperazinyl)-2-(methyloxy)phenyl]-2-thiophenesulfonamide 5-(2,4-Difluorophenyl)-N-[3-(cis-3,5-dimethyl-1-piperazinyl)-4-(methyloxy)phenyl]-2-thiophenesulfonamide N-[3-(cis-3,5-Dimethyl-1-piperazinyl)-4-(methyloxy)phenyl]-5-[2-(ethyloxy)phenyl]-2-thiophenesulfonamide N-[3-(cis-3,5-Dimethyl-1-piperazinyl)-4-(methyloxy)phenyl]-4'-methyl-2,2'-bithiophene-5-sulfonamide N-[3-(cis-3,5-Dimethyl-1-piperazinyl)-4-(methyloxy)phenyl]-5-{3-[(methyloxy)methyl]phenyl}-2-thiophenesulfonamide 5-(3-Chloro-4-fluorophenyl)-N-[3-(cis-3,5-dimethyl-1-piperazinyl)-4-(methyloxy)phenyl]-2-thiophenesulfonamide N-[3-(cis-3,5-Dimethyl-1-piperazinyl)-4-(methyloxy)phenyl]-5-(2-methylphenyl)-2-thiophenesulfonamide 5-(2,6-Dimethylphenyl)-N-[3-(cis-3,5-dimethyl-1-piperazinyl)-4-(methyloxy)phenyl]-2-thiophenesulfonamide 5-[5-Chloro-2-(methyloxy)phenyl]-N-[3-(cis-3,5-dimethyl-1-piperazinyl)-4-(methyloxy)phenyl]-2-thiophenesulfonamide 5-(3,5-Difluorophenyl)-N-[3-(cis-3,5-dimethyl-1-piperazinyl)-4-(methyloxy)phenyl]-2-thiophenesulfonamide 5-(4-Chlorophenyl)-N-[3-(cis-3,5-dimethyl-1-piperazinyl)-4-(methyloxy)phenyl]-2-thiophenesulfonamide N-[3-(cis-3,5-Dimethyl-1-piperazinyl)-4-(methyloxy)phenyl]-5-(2-fluorophenyl)-2-thiophenesulfonamide N-[3-(cis-3,5-Dimethyl-1-piperazinyl)-4-(methyloxy)phenyl]-5-(3-methylphenyl)-2-thiophenesulfonamide 5-(2,3-Difluorophenyl)-N-[3-(cis-3,5-dimethyl-1-piperazinyl)-4-(methyloxy)phenyl]-2-thiophenesulfonamide 5-(2-Chlorophenyl)-N-[3-(cis-3,5-dimethyl-1-piperazinyl)-4-(methyloxy)phenyl]-2-thiophenesulfonamide N-[3-(cis-3,5-Dimethyl-1-piperazinyl)-4-(methyloxy)phenyl]-5-(3-fluorophenyl)-2-thiophenesulfonamide 5-(3-Chlorophenyl)-N-[3-(cis-3,5-dimethyl-1-piperazinyl)-4-(methyloxy)phenyl]-2-thiophenesulfonamide N-[5-(cis-3,5-Dimethyl-1-piperazinyl)-2-fluorophenyl]-4-(2-thienyl)benzenesulfonamide N-[5-(cis-3,5-Dimethyl-1-piperazinyl)-2-fluorophenyl]-4-(3-furanyl)benzenesulfonamide N-[5-(cis-3,5-Dimethyl-1-piperazinyl)-2-fluorophenyl]-2-fluoro-4-(2-thienyl)benzenesulfonamide 2-Chloro-N-[5-(cis-3,5-dimethyl-1-piperazinyl)-2-fluorophenyl]-4-(2-thienyl)benzenesulfonamide 2-Chloro-N-[5-(cis-3,5-dimethyl-1-piperazinyl)-2-fluorophenyl]-4-(3-furanyl)benzenesulfonamide N-[5-(cis-3,5-Dimethyl-1-piperazinyl)-2-fluorophenyl]-2-methyl-4-(2-thienyl)benzenesulfonamide N-[5-(cis-3,5-Dimethyl-1-piperazinyl)-2-fluorophenyl]-4-(3-furanyl)-2-methylbenzenesulfonamide N-[5-(cis-3,5-Dimethyl-1-piperazinyl)-2-fluorophenyl]-3-fluoro-4-(2-thienyl)benzenesulfonamide N-[5-(cis-3,5-Dimethyl-1-piperazinyl)-2-fluorophenyl]-3-fluoro-4-(3-furanyl)benzenesulfonamide N-[3-(cis-3,5-Dimethyl-1-piperazinyl)-4-(methyloxy)phenyl]-2-(methyloxy)-4-(2-thienyl)benzenesulfonamide N-[5-(cis-3,5-Dimethyl-1-piperazinyl)-2-fluoro-4-(methyloxy)phenyl]-4-(2-thienyl)benzenesulfonamide N-[5-(cis-3,5-Dimethyl-1-piperazinyl)-2-(methyloxy)phenyl]-5-(3-furanyl)-2-thiophenesulfonamide 5-(2,3-Difluorophenyl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5'-methyl-2,2'-bithiophene-5-sulfonamide N-[3-(cis-3,5-Dimethyl-1-piperazinyl)-4-(methyloxy)phenyl]-5-(3-furanyl)-2-thiophenesulfonamide N-[3-(cis-3,5-Dimethyl-1-piperazinyl)-4-(methyloxy)phenyl]-5'-methyl-2,2'-bithiophene-5-sulfonamide N-[5-(cis-3,5-Dimethyl-1-piperazinyl)-2,4-bis(methyloxy)phenyl]-4-(2-thienyl)benzenesulfonamide N-{3-(cis-3,5-Dimethyl-1-piperazinyl)-4-[(trifluoromethyl)oxy]phenyl}-4-(2-thienyl)benzenesulfonamide N-{3-(cis-3,5-Dimethyl-1-piperazinyl)-4-[(trifluoromethyl)oxy]phenyl}-5-(2-pyridinyl)-2-thiophenesulfonamide N-[5-(cis-3,5-Dimethyl-1-piperazinyl)-2-(methyloxy)phenyl]-4-(5-methyl-2-furanyl)benzenesulfonamide N-[5-(cis-3,5-Dimethyl-1-piperazinyl)-2-(methyloxy)phenyl]-3-fluoro-4-(5-methyl-2-furanyl)benzenesulfonamide N-[5-(cis-3,5-Dimethyl-1-piperazinyl)-2-(methyloxy)phenyl]-5-(2-methyl-1,3-thiazol-4-yl)-2-thiophenesulfonamide N-[5-(cis-3,5-Dimethyl-1-piperazinyl)-2-(methyloxy)phenyl]-4-methyl-3,4-dihydro-2H-1,4-benzoxazine-7-sulfonamide 4-Bromo-N-[3-(cis-3,5-dimethyl-1-piperazinyl)phenyl]-2-(methyloxy)benzenesulfonamide N-[2-Chloro-5-(cis-3,5-dimethyl-1-piperazinyl)phenyl]-5-(2-pyridinyl)-2-thiophenesulfonamide 4-Bromo-N-[5-(cis-3,5-dimethyl-1-piperazinyl)-2-(methyloxy)phenyl]-1-naphthalenesulfonamide 5-(5-Chloro-1,2,4-thiadiazol-3-yl)-N-[5-(cis-3,5-dimethyl-1-piperazinyl)-2-(methyloxy)phenyl]-2-thiophenesulfonamide 2-Bromo-N-[5-(cis-3,5-dimethyl-1-piperazinyl)-2-(methyloxy)phenyl]-4-(trifluoromethyl)benzenesulfonamide 4-Bromo-2,6-dichloro-N-[5-(cis-3,5-dimethyl-1-piperazinyl)-2-(methyloxy)phenyl]benzenesulfonamide 2,6-Dichloro-N-[5-(cis-3,5-dimethyl-1-piperazinyl)-2-(methyloxy)phenyl]benzenesulfonamide 2,4-Dibromo-N-[5-(cis-3,5-dimethyl-1-piperazinyl)-2-(methyloxy)phenyl]benzenesulfonamide 2,4-Dichloro-N-[5-(cis-3,5-dimethyl-1-piperazinyl)-2-(methyloxy)phenyl]-5-methylbenzenesulfonamide 4-Bromo-N-[5-(cis-3,5-dimethyl-1-piperazinyl)-2-fluorophenyl]-2-(methyloxy)benzenesulfonamide 4-Bromo-N-[5-(cis-3,5-dimethyl-1-piperazinyl)-2-fluorophenyl]-3-methylbenzenesulfonamide N-[5-(cis-3,5-Dimethyl-1-piperazinyl)-2-fluorophenyl]-2-(methyloxy)-4-(2-thienyl)benzenesulfonamide N-[5-(cis-3,5-Dimethyl-1-piperazinyl)-2-fluorophenyl]-4-(3-furanyl)-2-(methyloxy)benzenesulfonamide N-[5-(cis-3,5-Dimethyl-1-piperazinyl)-2-fluorophenyl]-2-(methyloxy)-4-(4-methyl-2-thienyl)benzenesulfonamide N-[5-(cis-3,5-Dimethyl-1-piperazinyl)-2-fluorophenyl]-4-(4-methyl-2-thienyl)benzenesulfonamide N-[5-(cis-3,5-Dimethyl-1-piperazinyl)-2-fluorophenyl]-2-methyl-4-(4-methyl-2-thienyl)benzenesulfonamide N-[5-(cis-3,5-Dimethyl-1-piperazinyl)-2-fluorophenyl]-3-methyl-4-(4-methyl-2-thienyl)benzenesulfonamide N-[5-(cis-3,5-Dimethyl-1-piperazinyl)-2-(methyloxy)phenyl]-4-(1,3-thiazol-2-yl)benzenesulfonamide N-[5-(cis-3,5-Dimethyl-1-piperazinyl)-2-(methyloxy)phenyl]-4-(1-methyl-1H-pyrrol-2-yl)benzenesulfonamide N-[5-(cis-3,5-Dimethyl-1-piperazinyl)-2-(methyloxy)phenyl]-4-(2-pyrazinyl)benzenesulfonamide N-[5-(cis-3,5-Dimethyl-1-piperazinyl)-2-(methyloxy)phenyl]-4-(2-pyrimidinyl)benzenesulfonamide N-[5-(cis-3,5-Dimethyl-1-piperazinyl)-2-(methyloxy)phenyl]-6-(2-furanyl)-3-pyridinesulfonamide N-[5-(cis-3,5-Dimethyl-1-piperazinyl)-2-(methyloxy)phenyl]-6-(2-thienyl)-3-pyridinesulfonamide N-[5-(cis-3,5-Dimethyl-1-piperazinyl)-2-(methyloxy)phenyl]-6-(5-methyl-2-furanyl)-3-pyridinesulfonamide N-[5-(cis-3,5-Dimethyl-1-piperazinyl)-2-(methyloxy) phenyl]-6-(4-methyl-2-thienyl)-3-pyridinesulfonamide N-[5-(cis-3,5-Dimethyl-1-piperazinyl)-2-(methyloxy) phenyl]-5-(5-methyl-2-furanyl)-2-pyridinesulfonamide N-[2-(Methyloxy)-5-(cis-3,4,5-trimethyl-1-piperazinyl) phenyl]-4-(2-thienyl)benzenesulfonamide 2-Chloro-N-[5-(cis-3,5-dimethyl-1-piperazinyl)-2-(methyloxy)phenyl]-4-(3-thienyl)benzenesulfonamide 2-Chloro-N-[5-(cis-3,5-dimethyl-1-piperazinyl)-2-(methyloxy)phenyl]-4-(5-methyl-2-thienyl)benzenesulfonamide N-[5-(cis-3,5-Dimethyl-1-piperazinyl)-2-(methyloxy) phenyl]-3-(2-furanyl)benzenesulfonamide N-[5-(cis-3,5-Dimethyl-1-piperazinyl)-2-(methyloxy) phenyl]-3-(3-furanyl)benzenesulfonamide N-[5-(cis-3,5-Dimethyl-1-piperazinyl)-2-(methyloxy) phenyl]-3-(4-methyl-2-thienyl)benzenesulfonamide N-[5-(cis-3,5-Dimethyl-1-piperazinyl)-2-(methyloxy) phenyl]-3-methyl-4-(5-methyl-2-thienyl)benzenesulfonamide N-[3-(cis-3,5-Dimethyl-1-piperazinyl)phenyl]-2-(methyloxy)-4-(4-methyl-2-thienyl)benzenesulfonamide N-[3-(cis-3,5-Dimethyl-1-piperazinyl)phenyl]-4-(2-furanyl)-2-(methyloxy)benzenesulfonamide N-[3-(cis-3,5-Dimethyl-1-piperazinyl)phenyl]-2-(methyloxy)-4-(2-thienyl)benzenesulfonamide N-[5-(cis-3,5-Dimethyl-1-piperazinyl)-2-(methyloxy) phenyl]-2-methyl-4-(3-thienyl)benzenesulfonamide N-[5-(cis-3,5-Dimethyl-1-piperazinyl)-2-(methyloxy) phenyl]-2-fluoro-4-(5-methyl-2-thienyl)benzenesulfonamide N-[5-(cis-3,5-Dimethyl-1-piperazinyl)-2-(methyloxy) phenyl]-2,5-difluoro-4-(4-methyl-2-thienyl)benzenesulfonamide N-[5-(cis-3,5-Dimethyl-1-piperazinyl)-2-(methyloxy) phenyl]-2-methyl-4-(5-methyl-2-thienyl)benzenesulfonamide N-[5-(cis-3,5-Dimethyl-1-piperazinyl)-2-(methyloxy) phenyl]-3-fluoro-4-(3-thienyl)benzenesulfonamide N-[5-(cis-3,5-Dimethyl-1-piperazinyl)-2-(methyloxy) phenyl]-3-fluoro-4-(5-methyl-2-thienyl)benzenesulfonamide N-[5-(cis-3,5-Dimethyl-1-piperazinyl)-2-(methyloxy) phenyl]-2,5-difluoro-4-(2-furanyl)benzenesulfonamide N-[5-(cis-3,5-Dimethyl-1-piperazinyl)-2-(methyloxy) phenyl]-5-(3-pyridinyl)-2-thiophenesulfonamide N-[3-(cis-3,5-Dimethyl-1-piperazinyl)-4-(methyloxy) phenyl]-2'-methyl-4-biphenylsulfonamide N-[3-(cis-3,5-Dimethyl-1-piperazinyl)-4-(methyloxy) phenyl]-5-(4-fluorophenyl)-2-thiophenesulfonamide N-[5-(cis-3,5-Dimethyl-1-piperazinyl)-2-(methyloxy) phenyl]-2',4'-difluoro-4-biphenylsulfonamide N-[5-(cis-3,5-Dimethyl-1-piperazinyl)-2-(methyloxy) phenyl]-3',4'-difluoro-4-biphenylsulfonamide N-[2-Chloro-5-(cis-3,5-dimethyl-1-piperazinyl)phenyl]-4-(2-furanyl)benzenesulfonamide N-[2-Chloro-5-(cis-3,5-dimethyl-1-piperazinyl)phenyl]-5-(2-fluorophenyl)-2-thiophenesulfonamide N-[5-(cis-3,5-Dimethyl-1-piperazinyl)-2-(methyloxy) phenyl]-3-fluoro-4-(5-methyl-3-thienyl)benzenesulfonamide N-[5-(cis-3,5-Dimethyl-1-piperazinyl)-2-(methyloxy) phenyl]-2-fluoro-4-(5-methyl-3-thienyl)benzenesulfonamide N-[5-(cis-3,5-Dimethyl-1-piperazinyl)-2-(methyloxy) phenyl]-4-(5-methyl-3-thienyl)benzenesulfonamide 2-Chloro-N-[5-(cis-3,5-dimethyl-1-piperazinyl)-2-(methyloxy)phenyl]-4-(5-methyl-3-thienyl)benzenesulfonamide N-[5-(cis-3,5-Dimethyl-1-piperazinyl)-2-(methyloxy) phenyl]-7-(2-furanyl)-2,1,3-benzoxadiazole-4-sulfonamide 2-Chloro-N-[5-(cis-3,5-dimethyl-1-piperazinyl)-2-(methyloxy)phenyl]-4-(5-methyl-2-furanyl)benzenesulfonamide N-[5-(cis-3,5-Dimethyl-1-piperazinyl)-2-(methyloxy) phenyl]-3-fluoro-4-(2-furanyl)benzenesulfonamide 2-Chloro-N-[5-(cis-3,5-dimethyl-1-piperazinyl)-2-(methyloxy)phenyl]-4-(2-furanyl)benzenesulfonamide N-[5-(cis-3,5-Dimethyl-1-piperazinyl)-2-(methyloxy) phenyl]-2-fluoro-4-(5-methyl-2-furanyl)benzenesulfonamide N-[3-(cis-3,5-Dimethyl-1-piperazinyl)-4-(ethyloxy)phenyl]-4-(2-thienyl)benzenesulfonamide N-{2-(Methyloxy)-5-[(3S)-3-methyl-1-piperazinyl]phenyl}-4-(2-thienyl)benzenesulfonamide N-{2-(Methyloxy)-5-[(3R)-3-methyl-1-piperazinyl]phenyl}-4-(2-thienyl)benzenesulfonamide N-[5-(cis-3,5-Dimethyl-1-piperazinyl)-2-hydroxyphenyl]-4-(5-methyl-2-furanyl)benzenesulfonamide N-[5-(cis-3,5-Dimethyl-1-piperazinyl)-2-hydroxyphenyl]-4-(2-furanyl)benzenesulfonamide N-[5-(cis-3,5-Dimethyl-1-piperazinyl)-2-hydroxyphenyl]-3-fluoro-4-(5-methyl-2-furanyl)benzenesulfonamide N-[5-(cis-3,5-Dimethyl-1-piperazinyl)-2-hydroxyphenyl]-5-(2-fluorophenyl)-2-thiophenesulfonamide N-[5-(cis-3,5-Dimethyl-1-piperazinyl)-2-(methyloxy) phenyl]-4-[(phenylmethyl)oxy]benzenesulfonamide Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic, salicylic, lactic, mandelic or naphthalenesulfonic acid The compounds of formula (I) may be prepared in crystalline or non-crystalline form, and, if crystalline, may optionally be hydrated or solvated. This invention includes within its scope stoichiometric hydrates as well as compounds containing variable amounts of water.

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The subject invention also includes isotopically-labeled compounds, which are identical to those recited in formulae (I) and (IA), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{35}S$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention can generally be prepared by carrying out the procedures disclosed in the Schemes and/or in the Examples below, by substituting a readily available isotopically labeled reagent for a non-isotopically labeled reagent.

Compounds of the invention may be prepared using procedures which are analogous to those known in the art. However, the present invention also provides processes for the preparation of a compound of formula (I) or a pharmaceutically acceptable salt thereof, comprising:

Process (a) Coupling of a compound of formula (II)

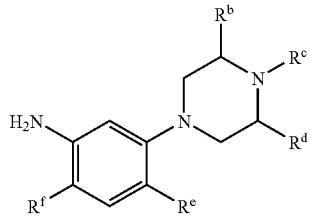

(II)

wherein $R^b$, $R^c$, $R^d$, $R^e$ and $R^f$ are as defined in formula (I) or protected derivatives thereof, with a compound of formula (III) wherein $R^a$ and Y are as defined in formula (I) and $L^1$ is a suitable leaving group, such as a suitable halogen group (e.g. chlorine) or a pentafluorophenyloxy group.

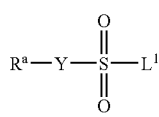

(III)

Process (a) typically comprises the use of a base, such as pyridine. Process (a) may comprise the use of a base, such as pyridine in an appropriate solvent such as dichloromethane. Alternatively process (a) may comprise the use of a solid supported base, such as morpholinomethyl-polystyrene HL resin in an appropriate solvent such as dichloromethane.

Compounds of formulae (III) are commercially available or may be prepared according to known methods or analogous to known methods.

Or Process (b) Interconversion of compounds of formula (I) to other compounds of formula (I).

Process (b) may be performed using conventional interconversion procedures such as epimerization, oxidation, reduction, hydrogenation, alkylation, dealkylation, nucleophilic or electrophilic aromatic substitution, ester hydrolysis, amide bond formation or transition metal mediated coupling reactions. Examples of transition metal mediated coupling reactions useful as interconversion procedures include the following: palladium catalyzed coupling reactions between organic electrophiles, such as aryl halides, and organometallic reagents, for example stannanes (Stille cross-coupling reactions) or other suitable reagents, for example boronic acids (Suzuki cross-coupling reactions); palladium catalyzed amination and amidation reactions between organic electrophiles, such as aryl halides, and nucleophiles, such as amines and amides; copper catalyzed amidation reactions between organic electrophiles (such as aryl halides) and nucleophiles such as amides; and copper mediated coupling reactions between phenols and boronic acids.

Compounds of formula (II) may be prepared in accordance with the following scheme:

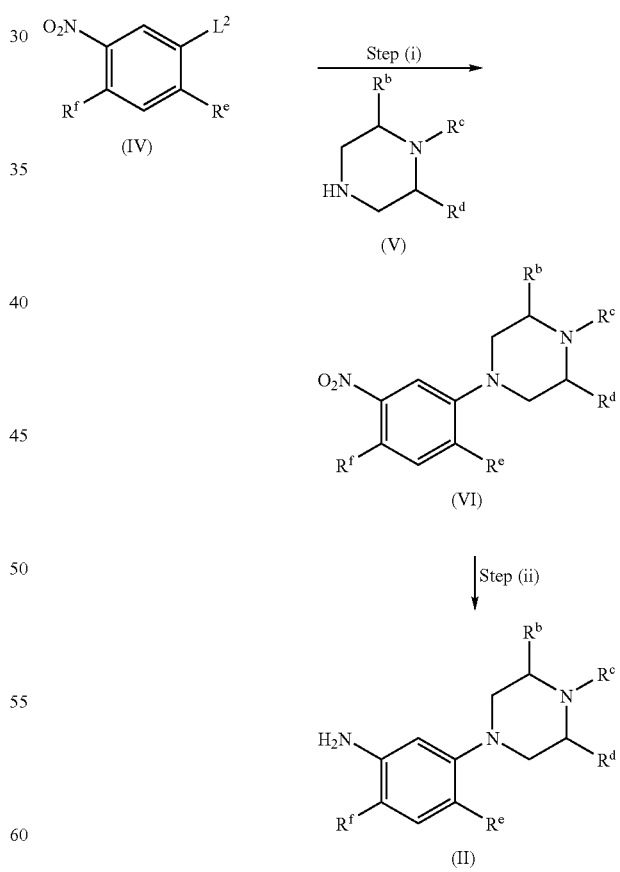

wherein $R^b$, $R^c$, $R^d$, $R^e$ and $R^f$ are defined as above, $L^2$ is a suitable leaving group, such as halogen (e.g. bromine).

When the leaving group $L^2$ is a halogen atom such (e.g. bromine or chlorine), step (i) typically comprises of treatment of a compound of formula (IV) with a piperazine of formula (V) with a transition metal catalyst such as a palladium salt (e.g. palladium (II) acetate), in combination with a suitable ligand, such as BINAP (2,2'-bis(diphenylphosphino)-1,1'-binaphthyl), in the presence of a base such as cesium carbonate, in an appropriate solvent such as dioxane at an appropriate temperature such as reflux.

Step (i) may also comprise the reaction of a compound of formula (IV) with a piperazine of formula (V) in an appropriate solvent such as 1-methyl-2-pyrrolidinone at an appropriate temperature such as 160° C. (for example, in a microwave reactor).

Step (ii) comprises the reduction of the nitro group in a compound of formula (VI) to an aniline of formula (II). Step (ii) may typically be performed under transition metal catalyzed hydrogenation conditions, for example, under an atmosphere of hydrogen employing a suitable catalyst, such as palladium on charcoal, in a suitable solvent, such as ethanol or using iron and aqueous ammonium chloride in an appropriate solvent such as methanol at an appropriate temperature (eg reflux).

Compounds of formulae (IV) and (V) are commercially available or may be prepared according to known methods or by analogy to known methods.

Or Process (c) reacting a compound of formula (VII)

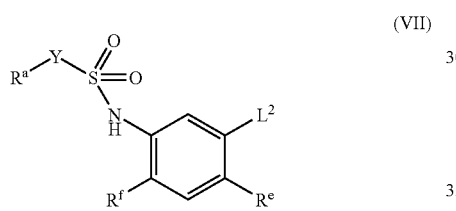

(VII)

wherein $R^a$, $R^e$, $R^f$ and Y are defined as above, $L^2$ is a suitable leaving group, such as halogen (e.g. iodine, bromine or chlorine), with a piperazine of formula (V) to give a compound of formula (I).

Process (c) may typically be performed with a transition metal catalyst such as a palladium salt (e.g. tris(dibenzylideneacetone)dipalladium(0)) in combination with a suitable ligand (e.g. 2-dicyclohexylphosphino-2'-(N,N-dimethylamino)biphenyl) in the presence of a base such as sodium tert-butoxide in an appropriate solvent such as dioxane at an appropriate temperature such as reflux. The reaction may also be carried out in a microwave reactor in an appropriate solvent such as dioxane at an appropriate temperature such as 125° C.

Compounds of formula (VII) may be interconverted to other compounds of formula (VII).

Compounds of formula (VII) may be prepared from an aniline of formula (VIII) and compound of formula (III) in an analogous manner to that described in process (a)

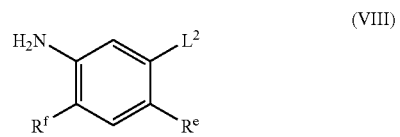

(VIII)

Anilines of formula (VIII) are commercially available or may be prepared according to known methods or analogous to known methods. For example compounds of formula (VIII) may be prepared by reduction of a nitro compound of formula (IV) using iron and aqueous ammonium chloride at an appropriate temperature such as reflux.

Compounds of formula (II) may also be prepared in accordance with the following scheme:

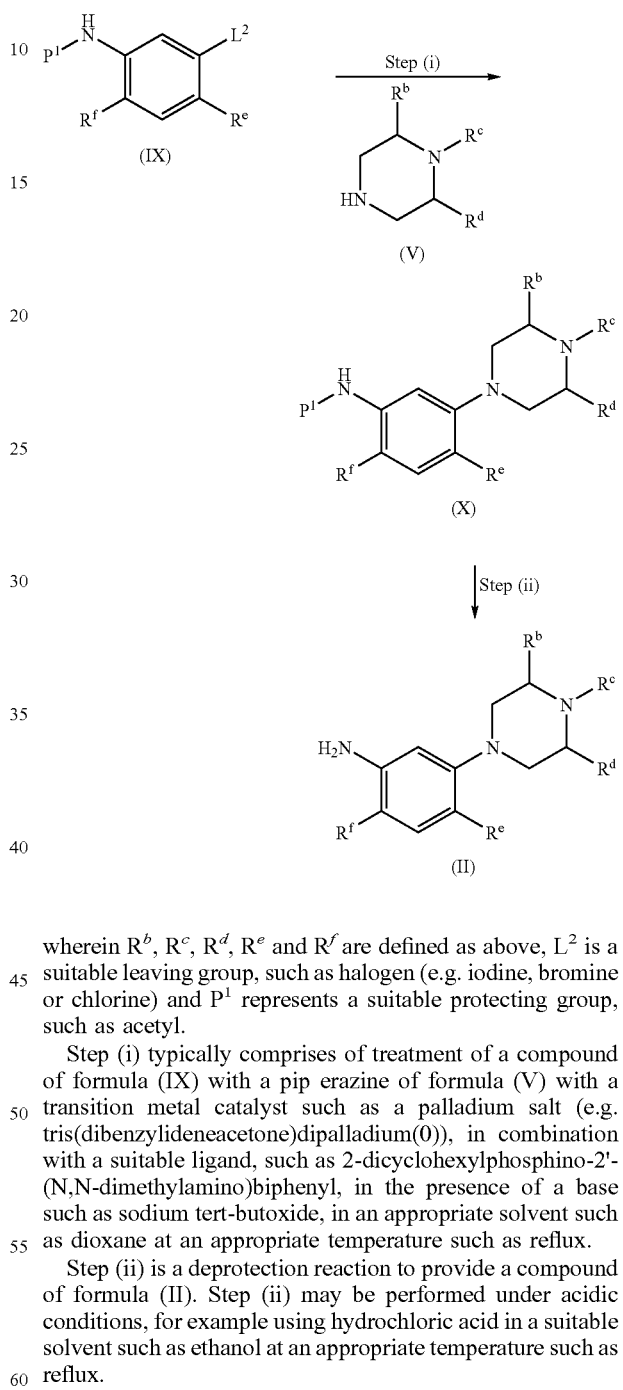

wherein $R^b$, $R^c$, $R^d$, $R^e$ and $R^f$ are defined as above, $L^2$ is a suitable leaving group, such as halogen (e.g. iodine, bromine or chlorine) and $P^1$ represents a suitable protecting group, such as acetyl.

Step (i) typically comprises of treatment of a compound of formula (IX) with a piperazine of formula (V) with a transition metal catalyst such as a palladium salt (e.g. tris(dibenzylideneacetone)dipalladium(0)), in combination with a suitable ligand, such as 2-dicyclohexylphosphino-2'-(N,N-dimethylamino)biphenyl, in the presence of a base such as sodium tert-butoxide, in an appropriate solvent such as dioxane at an appropriate temperature such as reflux.

Step (ii) is a deprotection reaction to provide a compound of formula (II). Step (ii) may be performed under acidic conditions, for example using hydrochloric acid in a suitable solvent such as ethanol at an appropriate temperature such as reflux.

Those skilled in the art will appreciate that it may be necessary to protect certain groups. Suitable protecting groups and methods for their attachment and removal are conventional in the art of organic chemistry, such as those described in T. W. Greene 'Protective Groups in Organic Synthesis' (J. Wiley and Son, 1991). For example, suitable protecting groups for the piperazine group include t-butyloxycarbonyl, benzyl, trifluoroacetyl, benzyloxycarbonyl, 2',2',2'-trichloroethoxycarbonyl, and methyl the latter of which may be removed with 1-chloroethyl chloroformate according to standard procedures.

The compounds of formula (I) have been found to be GHS-R agonists in the GTPγS and FLIPR (Flourometric Light Inaging Plate Reader) assay described herein.

Compounds of formula (I) and their pharmaceutically acceptable salts are therefore of use in the treatment of conditions or disorders which are mediated by compounds acting at the growth hormone secretagogue (GHS) receptors. In particular the compounds of formula (I) and their pharmaceutically acceptable salts are of use in the treatment of cachexia, sarcopenia, osteoporosis, rheumatoid arthritis, osteoarthritis, frailty associated with aging, growth hormone deficiency, metabolic disorders, sleep disorders, or congestive heart failure. The compounds of the invention will be useful treatments to alleviate symptoms associated with gastro-esophageal reflux and/or with dyspepsia, with or without appetite-/metabolic-related cachexia, the treatments of paralytic ileus or pseudo-obstruction, and of conditions associated with constipation, such as constipation-predominant irritable bowel syndrome.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions/disorders which can be mediated via the GHS receptors. In particular the invention provides a compound of formula (I) or a pharmaceutically acceptable salt thereof for use as a therapeutic substance in the treatment of cachexia, sarcopenia, osteoporosis, rheumatoid arthritis, osteoarthritis, frailty associated with aging, growth hormone deficiency, metabolic disorders, sleep disorders, congestive heart failure, alleviation of symptoms associated with gastro-esophageal reflux and/or with dyspepsia, with or without appetite-/metabolic-related cachexia, the treatments of paralytic ileus or pseudo-obstruction, and of conditions associated with constipation, such as constipation-predominant irritable bowel syndrome. It is to be understood that compounds of formula (I) may also be used in combination with other therapeutic substances.

The invention further provides a method of treatment of conditions or disorders in mammals including humans which can be mediated via the GHS receptors, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the GHS receptors.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinized maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilizing a compound of the invention or pharmaceutically acceptable salt thereof and a sterile vehicle. Formulations for injection may be presented in unit dosage form e.g. in ampoules or in multi-dose, utilizing a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilized before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilizing agents, dispersing agents, suspending agents, thickening agents, or colouring agents. Drops may be formulated with an aqueous or non-aqueous base also comprising one or more dispersing agents, stabilizing agents, solubilizing agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilized components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

No toxicological effects are indicated/expected when a compound (of the invention) is administered in the above mentioned dosage range.

All publications, including but not limited to patents and patent applications, cited in this specification are herein incorporated by reference as if each individual publication were specifically and individually indicated to be incorporated by reference herein as though fully set forth.

The following descriptions and Examples illustrate the preparation of compounds of the invention. Each Example was characterized either as the free base or hydrochloride salt or occasionally as the formic acid salt directly from mass directed autoprep HPLC. The hydrochloride salts were prepared by dissolving the pure material in dichloromethane or methanol and acidifying with ethereal HCl.

Where so indicated in the experimental section microwave heating was performed in Biotage Initiator 60 or Personal Chemistry Optimizer instruments. These instruments allowed the control of temperature up to 250° C. and allowed pressures up to 20 bar with microwave radiation up to 300 W at 2.45 GHz.

Conditions, Hardware and Software used for Mass Directed Auto-Purification System Hardware
Waters 2525 Binary Gradient Module
Waters 515 Makeup Pump
Waters Pump Control Module
Waters 2767 Inject Collect
Waters Column Fluidics Manager
Waters 2996 Photodiode Array Dectector
Waters ZQ Mass Spectrometer
Gilson 202 fraction collector
Gilson Aspec waste collector Software
Waters Masslynx version 4 SP2

Column
The columns used are Waters Atlantis, the dimensions of which are 19 mm×100 mm (small scale) and 30 mm×100 mm (large scale). The stationary phase particle size is 5 µm.

Solvents
A: Aqueous solvent=Water+0.1% Formic Acid
B: Organic solvent=Acetonitrile+0.1% Formic Acid
Make up solvent=Methanol: Water 80:20
Needle rinse solvent=Methanol Methods
There are four methods used depending on the analytical retention time of the compound of interest. They all have a 13.5-minute runtime, which comprises of a 10-minute gradient followed by a 13.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 mins)

Flow rate
All of the above methods have a flow rate of either 20 mls/min (Small Scale) or 40 mls/min (Large Scale)

Conditions, Hardware and Software for Analytical LCMS Systems

Hardware
Agilent 1100 Gradient Pump
Agilent 1100 Autosampler
Agilent 1100 DAD Dectector
Agilent 1100 Degasser
Agilent 1100 Oven
Agilent 1100 Controller
Waters ZQ Mass Spectrometer
Sedere Sedex 55, Sedere Sedex 85 or Polymer Labs PL-ELS-2100

Software
Waters MassLynx version 4.0 SP2

Column
The column used is a Waters Atlantis, the dimensions of which are 4.6 mm×50 mm. The stationary phase particle size is 3 µm.

Solvents
A: Aqueous solvent=Water+0.05% Formic Acid
B: Organic solvent=Acetonitrile+0.05% Formic Acid Method The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate

The above method has a flow rate of 3 ml/mins

Conditions used for NMR Hardware

Bruker 400 MHz Ultrashield

Bruker B-ACS60 Autosampler

Bruker Advance 400 Console

Bruker DPX250

Bruker AVANCE 500

Bruker DRX600

Software

User interface—NMR Kiosk

Controlling software—XWin NMR version 3.0

EXAMPLES

Description 1 cis-3,5-Dimethyl-1-[2-(methyloxy)-5-nitrophenyl]
piperazine (D1)

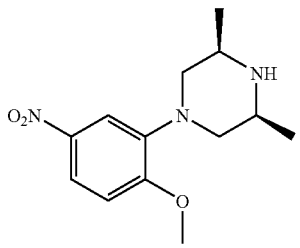

Cesium carbonate (9.77 g, 30 mmol), palladium (II) acetate (448 mg, 2 mmol) and rac-2,2'-bis(diphenylphosphino)-1,1'-binapthyl (1.87 g, 3 mmol) were stirred under an inert atmosphere in tetrahydrofuran (40 ml) for 30 minutes. 2-Bromo-4-nitroanisole (4.64 g, 20 mmol) and cis-2,6-dimethylpiperazine (6.85 g, 60 mmol) in tetrahydrofuran (20 ml) was added and the mixture heated at reflux for 24 hours. After cooling to room temperature the reaction mixture was diluted with ethyl acetate and extracted with 2N hydrochloric acid (×3). The aqueous extract was stirred with ethyl acetate and activated charcoal, filtered through celite. The aqueous component of the filtrate was separated and the pH of the solution was adjusted to pH 7 with 50% potassium hydroxide solution and the solution evaporated in vacuo to a small volume. The residue was basified to pH 10 with 50% potassium hydroxide solution and extracted with dichloromethane (×3). The combined organic extracts were washed with saturated brine, dried over anhydrous sodium sulfate and concentrated in vacuo to afford the title product (D1). MS (ES+) m/e 266 [M+H]+.

Description 2

3-(cis-3,5-Dimethyl-1-piperazinyl)-4-(methyloxy) aniline (D2)

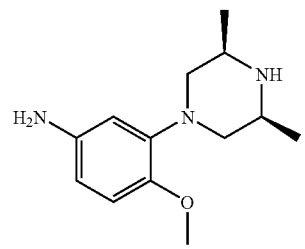

cis-3,5-Dimethyl-1-[2-(methyloxy)-5-nitrophenyl]piperazine (D1) (10 g, 38 mmol) and 10% palladium on charcoal were dissolved in ethanol (200 ml) and hydrogenated at room temperature under an atmosphere hydrogen for 16 hours. The mixture was filtered through celite and the filtrate concentrated in vacuo to afford the title product (D2). MS (ES+) m/e 236 [M+H]+.

Description 3 cis-3,5-Dimethyl-1-[4-(methyloxy)-3-nitrophenyl] piperazine (D3)

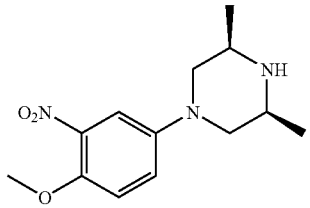

Palladium (II) acetate (941 mg, 4.2 mmol) and rac-2,2'-bis(diphenylphosphino)-1,1'-binapthyl (3.93 g, 6 mmol) were heated to 50° C. in dioxane (200 ml) for 30 minutes. Cesium carbonate (20.48 g, 63 mmol), 4-bromo-2-nitroanisole (9.75 g, 42 mmol) and cis-2,6-dimethylpiperazine (14.39 g, 126 mmol) were added and the mixture heated at reflux for 18 hours. The solids were filtered through celite and washed with ethyl acetate. The residue was concentrated and dissolved in ethyl acetate and extracted with 2N hydrochloric acid (×5). The combined extracts were washed in ethyl acetate (×3), basified with 0.880 ammonia and extracted with dichloromethane (×5). The combined organic extracts were concentrated, redissolved in ethyl acetate and washed with water (×3), saturated brine, dried over anhydrous sodium sulfate and concentrated. The residue was purified by column chromatography (Biotage Horizon, dichloromethane to 1:9 2M ammonia in methanol:dichloromethane) to afford the title product (D3). MS (ES+) m/e 266 [M+H]+.

Description 4

5-(cis-3,5-Dimethyl-1-piperazinyl)-2-(methyloxy) aniline (D4)

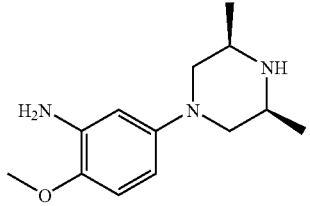

A mixture of cis-3,5-dimethyl-1-[4-(methyloxy)-3-nitrophenyl]piperazine (D3) (2.65 g, 10 mmol) in ethanol (60 ml)

containing palladium on charcoal (300 mg, 10% paste) was stirred under aone atmosphere of hydrogen gas overnight. The mixture was filtered through celite, the pad washed in ethanol and the combined ethanol solutions evaporated. The residue was purified by column chromatography (Biotage (SiO$_2$) 100 g, dichloromethane to 1:10 2M ammonia in methanol:dichloromethane) to afford the title product (D4). MS (ES+) m/e 236 [M+H]$^+$.

Description 5

1-[4-(cis-3,5-Dimethyl-1-piperazinyl)-2-nitrophenyl] ethanone (D5)

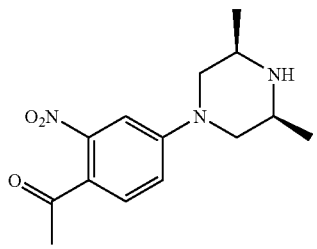

A mixture of 1-(4-chloro-2-nitrophenyl)ethanone (WO 9322287) (700 mg, 3.5 mmol) and cis-2,6-dimethylpiperazine (1.2 g, 10.5 mmol) in 1-methyl-2-pyrrolidinone (12 ml) was heated at 160° C. in a microwave reactor for 40 min. The reaction mixture was cooled, diluted with ethyl acetate and washed with water (×3), brine, dried over anhydrous magnesium sulfate and concentrated in vacuo. The resulting 1:1 mixture of the title compound (D5) MS (ES+) m/e [M+H]$^+$278 and 1-[4-chloro-2-(cis-3,5-dimethyl-1-piperazinyl)phenyl]ethanone MS (ES+) m/e [M+H]$^+$267/269 was used crude in the next reaction.

Description 6

1-[2-Amino-4-(cis-3,5-dimethyl-1-piperazinyl)phenyl]ethanone (D6)

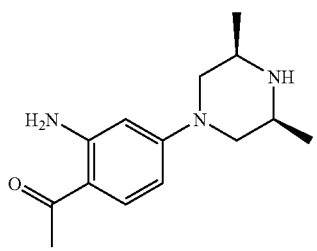

A mixture of the crude product from Description 5 in ethyl acetate (150 ml) containing palladium on charcoal (300 mg, 10% paste) was stirred under an atmosphere of hydrogen gas for 2 hours. The mixture was filtered through celite and the filtrate concentrated in vacuo. The residue was purified by column chromatography (dichloromethane to 1:20 2M ammonia in methanol:dichloromethane) to afford the title product (D6). MS (ES+) m/e 248 [M+H]$^+$.

Description 7

Phenyl 6-bromo-2-pyridinesulfonate (D7)

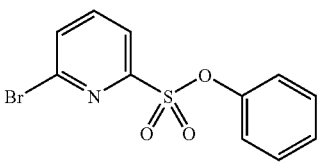

n-Butyl magnesium chloride (2.0 M in THF, 2.25 ml, 45 mmol) was added to a stirred solution of n-butyl lithium (1.6 M in hexanes, 5.56 ml, 8.9 mmol) at 0° C. under argon. After 10 minutes at 0° C. the mixture was cooled to −10° C. A solution of 2,6-dibromopyridine (3.0 g, 12.7 mmol) in toluene (35 ml) was added over 10 minutes and the mixture was stirred at −10° for 2 hours. After cooling to −40° C., sulfur dioxide gas was bubbled into the mixture for 5 minutes and the reaction was stirred at −40° C. for 30 minutes. Sulfuryl chloride (1.1 ml, 13.6 mmol) was added and the mixture was allowed to warm to room temperature. The resulting mixture was added over 5 minutes to a stirred mixture of phenol (1.25 g, 13.3 mmol) and triethylamine (7.0 ml, 50.6 mmol) in acetonitrile (30 ml) at 0° C. The mixture was stirred at 0° C. for 30 minutes and then at room temperature for 2 hours. The mixture was concentrated in vacuo and the residue partitioned between ethyl acetate and dilute sodium bicarbonate solution. The organic phase was washed with water, brine, dried over anhydrous magnesium sulfate and concentrated in vacuo to afford the title product (D7). MS (ES+) m/e 314/316 [M+H]$^+$.

Description 8

Phenyl 6-(3-thienyl)-2-pyridinesulfonate (D8)

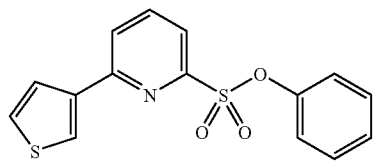

A mixture of phenyl 6-bromo-2-pyridinesulfonate (D7) (1.0 g, 7.2 mmol), 3-thienylboronic acid (532 mg, 8 mmol), [1,1'-bis(diphenylphosphino)ferrocene]-dichloropalladium (II) complex with dichloromethane (80 mg) in sodium carbonate (2M solution, 5 ml) and 1-methyl-2-pyrrolidinone (8 ml) was heated at 130° C. in a microwave reactor for 5 minutes. The reaction mixture was diluted with water and extracted with ethyl acetate. The organic phase was washed with water, brine, dried over anhydrous magnesium sulfate and concentrated in vacuo. The residue was purified by column chromatography (1:40 to 1:5 ethyl acetate:hexanes) to afford the title product (D8). MS (ES+) m/e 318 [M+H]$^+$.

Description 9

6-(3-Thienyl)-2-pyridinesulfonic acid sodium salt (D9)

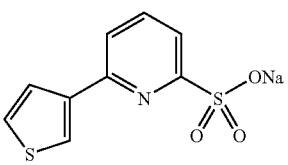

A mixture of phenyl 6-(3-thienyl)-2-pyridinesulfonate (D8) (634 mg, 2 mmol) and aqueous sodium hydroxide solution (1M, 12 ml) in ethanol (20 ml) was stirred at 60° C. for 18 hours. After cooling to room temperature the solution was concentrated in vacuo. The resulting residue was diluted with water, the pH was adjusted to pH 4-5 with 1M hydrochloric acid and the solution was washed with diethyl ether. The aqueous phase was concentrated in vacuo and the residue purified by reverse phase C18 silica chromatography (water to 1:10 methanol:water) to afford the title product (D9). MS (ES−) m/e 240 [M−Na]$^-$.

Description 10

6-(3-Thienyl)-2-pyridinesulfonyl chloride (D10)

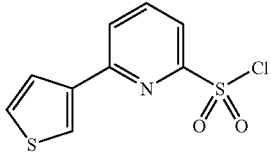

A mixture of 6-(3-thienyl)-2-pyridinesulfonic acid sodium salt (D9) and N,N-dimethylformamide (1 drop) in thionyl chloride (2 ml) was heated at 70° C. for 2 hours. After cooling to room temperature the solution was concentrated in vacuo and the residue co-evaporated with toluene (×2). The residue was triturated with diethyl ether to afford the title product (D10).

Description 11

Phenyl 5-(6-methyl-2-pyridinyl)-2-thiophenesulfonate (D11)

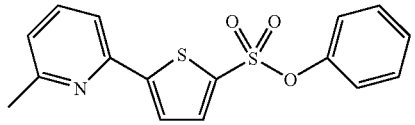

A mixture of phenyl 5-(trimethylstannanyl)-2-thiophenesulfonate (1.3 g, 3.2 mmol) (WO 9827069), 2-bromo-6-methylpyridine (550 mg, 3.2 mmol) and dichlorobis(triphenylphosphine)palladium (II) (100 mg) in 1-methyl-2-pyrrolidinone (10 ml) was heated at 90° C. under argon for 4 hours. After cooling to room temperature the mixture was diluted with water and extracted with ethyl acetate. The organic phase was washed with water, brine, dried over anhydrous magnesium sulfate and concentrated in vacuo. The residue was purified by chromatography (1:10 ethyl acetate:pentane) to afford the title product (D11). MS (ES+) m/e 332 [M+H]$^+$.

Description 12

5-(6-Methyl-2-pyridinyl)-2-thiophenesulfonyl chloride (D12)

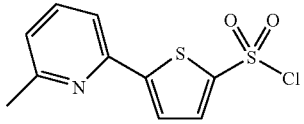

The title product (D12) was prepared from phenyl 5-(6-methyl-2-pyridinyl)-2-thiophenesulfonate (D11) using the procedures described in Description 9 and 10 (D9-D10). MS (ES+) 274/276 [M+H]$^+$.

Description 13

5-(cis-3,5-Dimethyl-1-piperazinyl)-2-fluoroaniline (D13)

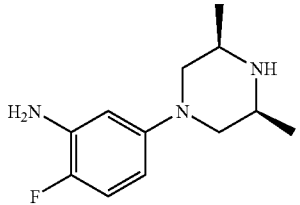

Step 1: N-(5-Bromo-2-fluorophenyl)acetamide

5-Bromo-2-fluoroaniline (14.79 g, 78 mmol) was heated at reflux in acetic acid (50 ml) and acetic anhydride (50 ml) for 8 hours. The solution was concentrated in vacuo, azeotroping with toluene. The residue was partitioned between ethyl acetate and saturated aqueous sodium bicarbonate solution. The organic phase was washed with water (×3), brine, dried over anhydrous magnesium sulfate and concentrated in vacuo. The residue was purified by chromatography on silica gel (gradient of hexane to ethyl acetate) to afford the title compound. MS (ES+) m/e 232/234 [M+H]$^+$.

Step 2: N-[5-(cis-3,5-Dimethyl-1-piperazinyl)-2-fluorophenyl]acetamide

The product of Step 1 (5.12 g, 18.7 mmol), cis-2,6-dimethyl piperazine (3.20 g, 28.1 mmol), sodium tert-butoxide (5.39 g, 56.1 mmol), tris(dibenzylideneacetone)dipalladium(0) (343 mg, 0.37 mmol) and 2-dicyclohexylphosphino-2'-(N,N-dimethylamino)biphenyl (444 mg, 1.12 mmol) were heated at reflux for 16 hours in 1,4-dioxane (50 ml). The solution was filtered through celite washing through with ethyl acetate. The filtrate was concentrated in vacuo, and the residue partitioned between ethyl acetate and saturated aqueous sodium bicarbonate solution. The organic phase was washed with water, 50% saturated brine solution, brine, dried over anhydrous sodium sulfate and concentrated in vacuo. The residue was purified by chromatography on silica gel (ethyl acetate, then a gradient of dichloromethane to 10% 2M methanolic ammonia in dichloromethane) to afford the title compound. MS (ES+) m/e 266 [M+H]$^+$.

Step 3: 5-(cis-3,5-Dimethyl-1-piperazinyl)-2-fluoroaniline (D13)

The product of Step 2 (9.27 g, 35 mmol) was heated at reflux in 5N hydrochloric acid (100 ml) for 3 hours. The solution was washed with ethyl acetate (×2), basified to pH10 with 0.880 ammonia and extracted with dichloromethane (×3). The combined extracts were washed with brine, dried over anhydrous sodium sulfate and concentrated in vacuo. The residue was purified by chromatography on silica gel (gradient of dichloromethane to 20% 2M methanolic ammonia in dichloromethane) to afford the title compound (D13). MS (ES+) m/e 224 [M+H]$^+$.

Description 14

4-Bromo-1-(ethyloxy)-2-nitrobenzene (D14)

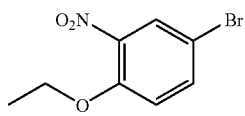

4-Bromo-2-nitrophenol (5.0 g, 23 mmol) and potassium carbonate (9.52 g, 69 mmol) were suspended in 2-butanone (100 ml). Ethyl iodide (2.2 ml, 28 mmol) was added dropwise at room temperature and stirred for 30 minutes. The suspension was heated at reflux for 18 hours, cooled and filtered, and the residue washed with acetone. The filtrate was concentrated in vacuo to a crude solid that was used without further purification (D14). 1H-NMR (CDCl$_3$) δ 7.42 (1H, d, J 2.5 Hz), 7.60 (1H, dd, J 9.0, 2.5 Hz), 6.96 (1H, d, J 9.0 Hz), 4.17 (2H, q, J 7.0 Hz), 1.47 (3H, t, J 7.0 Hz).

Description 15

4-Bromo-1-[(1-methylethyl)oxy]-2-nitrobenzene (D15)

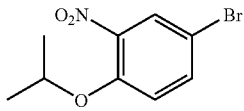

The title compound (D15) was prepared using a similar method to that described in Description 14 substituting ethyl iodide with isopropyl iodide. 1H-NMR (CDCl$_3$) δ 7.90 (1H, d, J 2.5 Hz), 7.58 (1H, dd, J 9.0 Hz), 6.97 (1H, d, J 9.0 Hz), 4.64 (1H, m), 1.39 (6H, d, J6.0 Hz).

Description 16

4-Bromo-1-[(methyloxy)methyl]-2-nitrobenzene (D16)

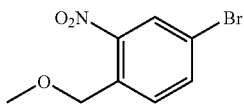

4-Bromo-1-(bromomethyl)-2-nitrobenzene (*Heterocycles* 1994, 39, 767) (8.3 g, 28 mmol) was dissolved in methanol (75 ml) at 0° C. 30% Sodium methoxide in methanol solution (10.7 ml, 56 mmol) was added dropwise and the solution stirred at room temperature for 4 hours. The mixture was concentrated to a small volume and partitioned between ethyl acetate and saturated aqueous sodium hydrogen carbonate solution. The organic layer was separated and then washed with saturated aqueous sodium bicarbonate solution, water (×3), brine, dried over anhydrous sodium sulfate and concentrated in vacuo. The residue was purified by chromatography on silica gel (hexane to ethyl acetate) to afford the title compound (D16). MS (ES+) m/e 246/248 [M+H]$^+$.

Description 17

1-Bromo-2,4-bis(methyloxy)-5-nitrobenzene (D17)

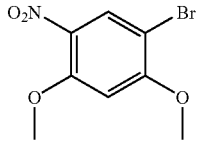

1,3-Dimethoxy-4-nitrobenzene (5.0 g, 27 mmol) in chloroform (50 ml) at 0° C., was treated with a solution of bromine (1.68 ml, 33 mmol) in chloroform (50 ml). The solution was stirred with warming to room temperature for 4 hours, washed with 10% sodium thiosulfate solution and brine then dried over anhydrous magnesium sulfate and concentrated in vacuo. The crude product was used without further purification (D17). MS (ES+) m/e 262/264 [M+H]$^+$.

Description 18

5-(cis-3,5-Dimethyl-1-piperazinyl)-4-fluoro-2-(methyloxy)aniline (D18)

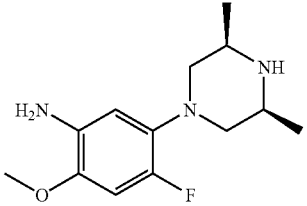

Step 1: N-[4-Fluoro-2-(methyloxy)phenyl]acetamide

A solution of 4-fluoro-2-(methyloxy)aniline (*Heterocycles* 1992, 34, 2301-2311) (5.6 g, 40 mmol) and triethylamine (6.9 ml, 50 mmol) in dichloromethane (200 ml) at 0° C. was treated with acetyl chloride (2.85 ml, 40 mmol). After stirring at room temperature for 1 hour the solution was washed with 2N hydrochloric acid. The organic phase was separated, washed with water and brine then dried over anhydrous magnesium sulfate and concentrated in vacuo. The residue was purified by chromatography on silica gel (1:5 to 1:2 ethyl acetate in dichloromethane) to afford the title compound. MS (ES+) m/e 184 [M+H]$^+$.

Step 2: N-[5-Bromo-4-fluoro-2-(methyloxy)phenyl]acetamide

Bromine (1.8 ml, 34 mmol) was added dropwise to a solution of the product of Step 1 (5.69 g, 31 mmol) in acetic acid (100 ml). After 18 hours at room temperature additional bromine (0.3 ml) was added and the solution stirred for a further 3 hours. The solution was partitioned between water and ethyl acetate and the layers separated. The organic phase was then washed with aqueous sodium thiosulfate solution, water and brine, dried over anhydrous magnesium sulfate and concentrated in vacuo to give the title compound. MS (ES+) m/e 262/264 [M+H]$^+$.

Step 3: N-[5-(cis-3,5-Dimethyl-1-piperazinyl)-4-fluoro-2-(methyloxy)phenyl]acetamide The title compound was prepared from the product of Step 2 using a similar method to that described in Step 2 of Description 13. MS (ES+) m/e 296 [M+H]$^+$.

Step 4: 5-[cis-3,5-Dimethyl-1-piperazinyl]-4-fluoro-2-(methyloxy)aniline (D18)

A mixture of product from Step 3 (883 mg, 3 mmol) in ethanol (40 ml) containing concentrated hydrochloric acid (2 ml) was heated at reflux for 15 hours. After cooling, the mixture was purified using an SCX ion exchange cartridge (Varian bond-elute) eluting with methanol and then 2M ammonia in methanol. The appropriate basic fractions were reduced in vacuo to afford the title compound (D18). MS (ES+) m/e 254 [M+H]$^+$.

Description 19

5-(cis-3,5-Dimethyl-1-piperazinyl)-2-fluoro-4-(methyloxy)aniline (D19)

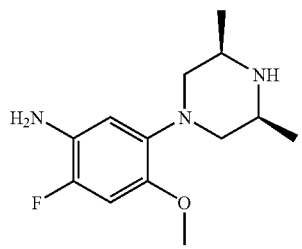

The title compound (D19) was prepared using a similar method to that described in Description 18 (D18) substituting 4-fluoro-2-(methyloxy)aniline with 2-fluoro-4-(methyloxy)aniline hydrochloride. MS (ES+) m/e 254 [M+H]+.

Description 20

2-Amino-4-(cis-3,5-dimethyl-1-piperazinyl)benzonitrile (D20)

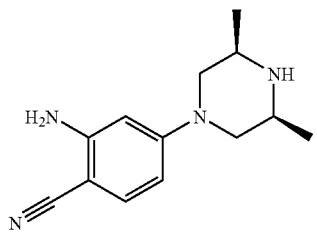

Step 1: 4-(cis-3,5-Dimethyl-1-piperazinyl)-2-nitrobenzonitrile

A mixture of 4-chloro-2-nitrobenzonitrile (*Tetrahedron* 1994, 50, 5515-5126) (650 mg, 3.56 mmol), sodium methoxide (270 mg, 5.00 mmol) and acetato-(2'-di-tert-butylphosphino-1,1'-biphenyl-2-yl)palladium (II) (115 mg, 0.25 mmol) was treated with triethylamine (0.25 ml, 1.79 mmol) followed by cis-2,6-dimethylpiperazine (488 mg, 4.27 mmol) and the mixture heated to 85° C. under an inert atmosphere over 30 minutes. The mixture was then kept at this temperature for 16 hours. The mixture was then filtered through kieselguhr, washing with toluene (50 ml) and the filtrate reduced in vacuo. The residue was then purified using an SCX ion exchange cartridge (Varian bond-elute) eluting with methanol followed by 2M ammonia in methanol to afford a dark residue which was purified by mass directed autoprep BPLC to afford the title compound as the formic acid salt. MS (ES+) m/e 261 [M+H]+.

Step 2: 2-Amino-4-(cis-3,5-dimethyl-1-piperazinyl)benzonitrile (D20)

A solution of the product of Step 1 (186 mg, 0.71 mmol) in ethanol (14 ml) and methanol (3-4 ml) was treated with palladium on charcoal (37 mg, 10% paste) and stirred under an atmosphere of hydrogen for 16 hours. The mixture was then filtered through celite, washing with ethanol and the then evaporated in vacuo. Purification of the residue by mass directed autoprep HPLC gave the title compound (D20) as the formic acid salt. MS (ES+) m/e 231 [M+H]+.

Descriptions 21-29

Descriptions 21-29 (D21-D29) were prepared using a similar method to that described for Description 3 (D3) followed by Description 2 (D2) substituting 4-bromo-2-nitroanisole for the appropriate aryl halide indicated in the table:

| Description | Aryl Halide | MS [M + H]+ |
|---|---|---|
| 3-(cis-3,5-Dimethyl-1-piperazinyl)aniline (D21) | 1-Bromo-3-nitrobenzene | 206 |
| 5-(cis-3,5-Dimethyl-1-piperazinyl)-2-(ethyloxy)aniline (D22) | 4-Bromo-1-(ethyloxy)-2-nitrobenzene (D14) | 250 |
| 5-(cis-3,5-Dimethyl-1-piperazinyl)-2-[(1-methylethyl)oxy]aniline (D23) | 4-Bromo-1-[(1-methylethyl)oxy]-2-nitrobenzene (D15) | 264 |
| 5-(cis-3,5-Dimethyl-1-piperazinyl)-2-[(methyloxy)methyl]aniline (D24) | 4-Bromo-1-[(methyloxy)methyl]-2-nitrobenzene (D16) | 250 |
| 5-(cis-3,5-Dimethyl-1-piperazinyl)-2,4-bis(methyloxy)aniline (D25) | 1-Bromo-2,4-bis(methyloxy)-5-nitrobenzene (D17) | 266 |
| 3-(cis-3,5-Dimethyl-1-piperazinyl)-4-[(phenylmethyl)oxy]aniline (D26) | 2-Bromo-4-nitro-1-[(phenylmethyl)oxy]benzene (WO 2001004111) | 312 |
| 3-(cis-3,5-Dimethyl-1-piperazinyl)-4-(ethyloxy)aniline (D27) | 2-Bromo-1-(ethyloxy)-4-nitrobenzene (WO 9719084) | 250 |
| 4-Amino-2-(cis-3,5-dimethyl-1-piperazinyl)benzonitrile (D28) | 2-Bromo-4-nitrobenzonitrile (Bulletin des Societes Chimiques Belges 1971, 80(3-4), 245-52) | 231 |
| 5-(cis-3,5-Dimethyl-1-piperazinyl)-2-methylaniline (D29) | 4-Bromo-1-methyl-2-nitrobenzene | 220 |

Description 30

4-Bromo-2-(methyloxy)benzenesulfonyl chloride (D30)

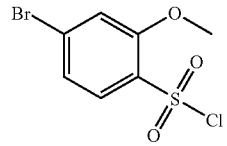

To chlorosulfonic acid (20 ml) at 0° C. was added dropwise 3-bromoanisole (18.7 g, 0.1 mol) at such a rate that the internal temperature remained below 5° C. The mixture was stirred at 0° C. for 1 hour and added dropwise to crushed ice. The mixture was extracted with ethyl acetate and the combined organic layers were washed with water and brine, dried over anhydrous magnesium sulfate and concentrated in vacuo. The residue was purified by chromatography on silica gel (1:25 ethyl acetate:pentane) to afford the title compound; 4-bromo-2-(methyloxy)benzenesulfonyl chloride (D30) 1H-NMR (CDCl$_3$) δ 7.81 (1H, d, J 8 Hz), 7.28 (1H, d, J 2 Hz), 7.26 (1H, dd, J 8, 2 Hz), 4.07 (3H, s) and an isomer; 2-bromo-4-(methyloxy)benzenesulfonyl chloride 1H-NMR (CDCl$_3$) δ 8.12 (1H, d), 7.33 (1H, d), 6.97 (1H, dd), 3.92 (3H, s).

Description 31

4-(2-Thienyl)benzenesulfonyl chloride and 4-(5-chloro-2-thienyl)benzenesulfonyl chloride (D31)

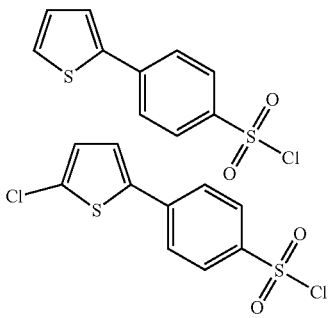

A suspension of 4-(2-thienyl)benzenesulfonic acid (WO 9827069) (10 mmol) in thionyl chloride (30 ml) was treated dropwise with N,N-dimethylformamide (5 drops) and the resulting mixture heated at 50° C. for 3 hours. The mixture was then concentrated in vacuo, azeotroped with toluene (×3) and the residue washed with 3% aqueous sodium hydrogen carbonate, water and brine, dried over magnesium sulfate and concentrated in vacuo to a crude solid (D31), containing a mixture of the title compounds (in a 2.6:1 ratio respectively) that was used without further purification. 4-(2-thienyl)benzenesulfonyl chloride, major component; 1H-NMR (CDCl$_3$) δ 8.03 (2H, d, J 8.8 Hz), 7.81 (2H, d, J 8.8 Hz), 7.50 (1H, dd, J 3.8, 1.0 Hz), 7.46 (1H, dd, J 5.1, 1.1 Hz), 7.16 (1H, dd, J 5.1, 3.8 Hz) and 4-(5-chloro-2-thienyl)benzenesulfonyl chloride, minor component): 1H-NMR (CDCl$_3$) δ 8.03 (2H, d), 7.71 (2H, d), 7.28 (1H, d), 6.98 (1H, d).

Description 32

6-Chloro-3-pyridinesulfonyl chloride hydrochloride (D32)

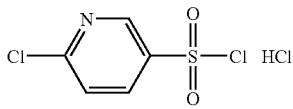

Step 1: 6-Chloro-3-pyridinesulfonic acid sodium salt

A solution of 6-chloro-3-pyridinesulfonyl chloride (5.0 g, 24 mmol) (C. Rath. Annalen. 1931, 487, 105-119) in dioxane (10 ml) and the solution cooled to 0° C. A solution of sodium hydroxide (1.88 g, 47 mmol) in water (20 ml) was added drop-wise to the stirred solution over 10 mins. After another 10 mins 0.5 pellet of NaOH was added and after a further 15 minutes the pH was adjusted to pH 7 with 2M hydrochloric acid and the solvent was vacuumed down. The material was dried on a Dean and Stark trap to give the title compound. MS (ES−) 192/194 [M−H]$^-$.

Step 2: 6-Chloro-3-pyridinesulfonyl chloride hydrochloride (D32)

A mixture of the product of Step 1 (430 mg, 2 mmol) in thionyl chloride (3 ml) and N,N-dimethylformide (2 drops) was heated at 70° C. for 3 hours. After cooling to room temperature the solvent was evaporated and the residue co-evaporated with toluene (×2) to give the title compound (D32) which was used directly in Step 1 of Example 272. 1H-NMR (CDCl$_3$) δ 7.61 (1H, m), 8.25 (1H, m), 9.03 (1H, m).

Description 33

5-Bromo-2-pyridinesulfonyl chloride (D33)

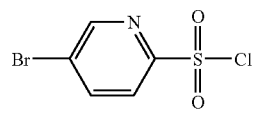

Step 1: 5-Bromo-2-[(phenylmethyl)thio]pyridine

A solution of phenylmethanethiol (1 ml, 8 mmol) in N,N-dimethylformamide (15 ml) under an atmosphere of argon was treated with sodium hydride (352 mg, 8.8 mmol, 60% dispersion in oil). After stirring at room temperature for 15 minutes a solution of 5-bromo-2-chloropyridine (1.84 g, 9.6 mmol) in N,N-dimethylformamide (5 ml) was added. After 2 hours, water and ethyl acetate were added. The organic layer was separated and washed with water, brine and dried over anhydrous magnesium sulfate and concentrated in vacuo. The residue was then purified by chromatography on silica gel eluting with 5% ethyl acetate in pentane to give the title compound. MS (ES+) 280/282 [M+H]$^+$.

Step 2: 5-Bromo-2-pyridinesulfonyl chloride (D33)

A mixture of the product of Step 1 (560 mg, 2 mmol) in carbon tetrachloride (20 ml) and water (5 ml) was stirred at 0° C. Chlorine gas was bubbled through the reaction mixture for 15 minutes, the solution was stirred for a further 15 minutes and argon was then bubbled through the solution for 15 minutes. Ice water and dichloromethane were added and the organic phase was separated, dried over anhydrous magnesium sulfate and evaporated to give the title compound (D33) which was used directly in the next reaction. 1H-NMR (CDCl₃) 8.9 (1H, m), 8.2 (1H, m), 6 8.0 (1H, m).

Description 34

5-(cis-3,5-Dimethyl-1-piperazinyl)-2-chloroaniline (D34)

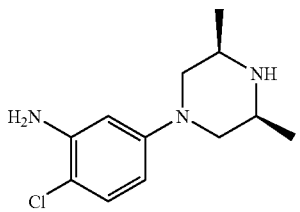

Step 1: 2-Chloro-5-iodoaniline

To 1-chloro-4-iodo-2-nitrobenzene (1.27 g, 4.49 mmol) in methanol (20 ml) was added iron powder (1.25 g, 22 mmol) and the reaction heated to 50° C. A solution of ammonium chloride (1.92 g, 36 mmol) in water (10 ml) was added slowly and the reaction heated to 70° C. overnight. Reaction was cooled, filtered through celite, washed with methanol and solvent reduced in vacuo. The residue was purified by chromatography on silica gel (gradient of hexane to 10% ethyl acetate in hexane) to afford the title compound. MS (ES+) m/e 254 [M+H]⁺.

Step 2: 5-(cis-3,5-Dimethyl-1-piperazinyl)-2-chloroaniline (D34)

2-Chloro-5-iodoaniline (630 mg, 2.49 mmol) was heated at reflux in acetic acid (7 ml) and acetic anhydride (7 ml) for 18 hours. The solution was concentrated in vacuo, azeotroping with toluene. The residue was partitioned between ethyl acetate and saturated aqueous sodium bicarbonate solution. The organic phase separated and washed with saturated aqueous sodium bicarbonate solution, water, brine, dried over anhydrous magnesium sulfate and concentrated in vacuo to afford a mixture of the mono- and di-acylated acetamide (N-(2-chloro-5-iodophenyl)acetamide and N-acetyl-N-(2-chloro-5-iodophenyl)acetamide). To this product (820 mg) in 1,4-dioxane (12 ml) was added cis-2,6-dimethyl piperazine (416 mg, 3.64 mmol), sodium tert-butoxide (700 mg, 7.29 mmol), tris(dibenzylideneacetone) dipalladium(0) (45 mg, 0.049 mmol) and 2-dicyclohexylphosphino-2'-(N,N-dimethylamino)biphenyl (39 mg, 0.098 mmol) and the reaction heated at reflux for 18 hours under argon. The reaction mixture was cooled, diluted with ethyl acetate (30 ml) and stirred with a mixture of celite and charcoal. The solution was filtered through celite washing with ethyl acetate. The filtrate was concentrated in vacuo, and the residue partitioned between ethyl acetate and saturated aqueous sodium bicarbonate solution. The organic phase was washed with water, 50% saturated brine solution, brine, dried over anhydrous sodium sulfate and concentrated in vacuo. The residue was treated with 5N HCl (20 ml) and heated at reflux for 24 hours under argon. The reaction was cooled, and the solution washed with ethyl acetate (×3), poured onto ice, basified with 0.880 ammonia and extracted with dichloromethane (×4). The combined extracts were washed with water, brine, dried over anhydrous sodium sulfate and concentrated in vacuo. The residue was purified by chromatography on silica gel (gradient of 2% to 10% methanol in dichloromethane) to afford the title compound (D34). MS (ES+) m/e 240/242 [M+H]⁺.

Description 35

4-Bromo-N-[2-chloro-5-(cis-3,5-dimethyl-1-piperazinyl)phenyl]benzenesulfonamide (D35)

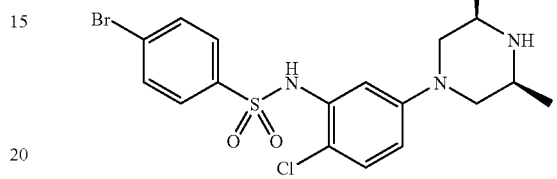

A solution of 5-(cis-3,5-dimethyl-1-piperazinyl)-2-chloroaniline (D34) (108 mg, 0.45 mmol) in pyridine:dichloromethane (1:1, 4 ml) was treated with 4-bromobenzenesulfonyl chloride (138 mg, 0.54 mmol). The solution was stirred at room temperature for 2 hours, quenched with methanol and concentrated in vacuo. The residue was applied to a SCX cartridge (Varian bond-elute, 5 g) and washed with methanol and 2M ammonia in methanol. The combined basic fractions were concentrated in vacuo and the resulting residue was purified by column chromatography (FlashMaster) (dichloromethane to 5% methanol:dichloromethane) to afford some pure product. The impure fractions were purified further by MDAP, and combined with the above pure product to afford the title product (D35). MS (ES+) m/e 458/460/462 [M+H]⁺.

Description 36

5-Bromo-N-[2-chloro-5-(cis-3,5-dimethyl-1-piperazinyl)phenyl]-2-thiophenesulfonamide (D36)

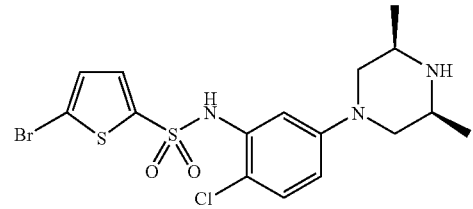

A solution of 5-(cis-3,5-Dimethyl-1-piperazinyl)-2-chloroaniline (D34) (100 mg, 0.42 mmol) in pyridine:dichloromethane (1:1, 4 ml) was treated with 5-bromo-2-thiophenesulfonyl chloride (132 mg, 0.51 mmol). The solution was stirred at room temperature for 2 hours, quenched with methanol and concentrated in vacuo. The residue was applied to a SCX cartridge (Varian bond-elute, 5 g) and washed with methanol and 2M ammonia in methanol. The combined basic fractions were concentrated in vacuo and the resulting residue was purified by column chromatography (FlashMaster) (gradient of dichloromethane to 4% metlianol:dichloromethane) to afford the title product (D36). MS (ES+) m/e 464/466/468 [M+H]⁺.

Description 37

4-Bromo-N-[5-(cis-3,5-dimethyl-1-piperazinyl)-2-(methyloxy)phenyl]-2,5-difluorobenzenesulfonamide (D37)

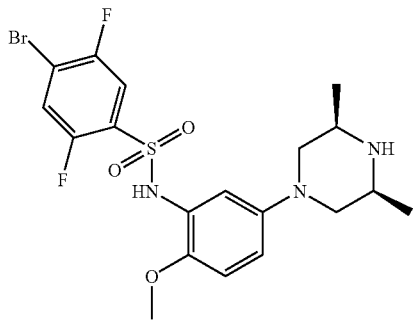

A solution of 5-(cis-3,5-dimethyl-1-piperazinyl)-2-(methyloxy)aniline (D4) (500 mg, 2.12 mmol) in dichloromethane (30 ml) was treated with morpholinomethyl-polystyrene HL resin (1 g, 4 mmol/g loading, 4.24 mmol) followed by 4-bromo-2,5-difluorobenzene sulfonyl chloride (930 mg, 3.2 mmol). The resulting solution was stirred room temperature for 18 hours and was then filtered, washing with dichloromethane, and the filtrate concentrated in vacuo. The residue was then purified using an SCX ion exchange cartridge (Varian bond-elute) eluting with methanol followed by ammonia (0.5M to 2M in methanol). The appropriate fractions were combined and reduced in vacuo to afford a crude product which was purified further by trituration with methanol to afford the desired product D37. MS (ES+) m/e 490/492 [M+H]$^+$.

Description 38

4,4,5,5-Tetramethyl-2-(5-methyl-3-thienyl)-1,3,2-dioxaborolane (D38)

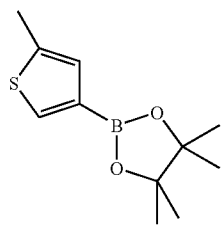

To 4-bromo-2-methylthiophene (1.5 g, 8.5 mmol) in THF (17 ml) was added bis[(1,1-dimethylethyl)phosphanyl]palladium (218 mg, 0.43 mmol), then N,N-diethylethanamine (2.5 g, 25.4 mmol) and 4,4,5,5-tetramethyl-1,3,2-dioxaborolane (1.63 g, 12.7 mmol) and the resulting mixture heated at 40° C. under argon for 2 hours. The reaction was cooled and then filtered, washing with tert-butyl methyl ether. The washings were reduced in vacuo and the residue purified by chromatography on silica gel (gradient of hexane to 3% ethyl acetate:hexane) to afford the title compound (D38). MS (ES+) m/e 225 [M+H]$^+$.

Description 39

5-(cis-3,5-Dimethyl-1-piperazinyl)-2-[(phenylmethyl)oxy]aniline (D39)

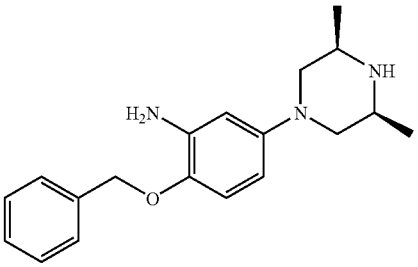

Step 1: 4-Bromo-2-nitro-1-[(phenylmethyl)oxy]benzene

To a solution of 4-bromo-2-nitrophenol (5.2 g, 23.8 mmol) in 2-butanone (100 ml) was added potassium carbonate (9.0 g, 65.1 mmol) followed by benzyl bromide (2.6 ml, 21.8 mmol). The resulting mixture was stirred at room temperature for 30 minutes and then heated to reflux overnight. The solids were then removed by filtration, washing with acetone, and the filtrate reduced in vacuo. The residue was dissolved in ethyl acetate and washed with 2M aqueous sodium hydroxide solution (×3) and then brine. The organic layer was separated, dried over anhydrous magnesium sulfate, filtered and reduced in vacuo to afford the title product. 1H-NMR (d6-DMSO) δ 8.14 (1H, d, J 3.5 Hz), 7.84 (1H, dd, J 11.0, 3.5 Hz), 7.45-7.39 (5H, m), 7.37-7.33 (2H, m), 5.32 (2H, s).

Step 2: cis-3,5-Dimethyl-1-{3-nitro-4-[(phenylmethyl)oxy]phenyl}piperazine

To a solution of 4-bromo-2-nitro-1-[(phenylmethyl)oxy]benzene (7.0 g, 22.7 mmol) in dioxane (120 ml) was added cis-2,6-dimethylpiperazine (7.8 g, 67.4 mmol) followed by cesium carbonate (11.0 g, 33.8 mmol), rac-2,2'-bis(diphenylphosphino)-1,1'-binapthyl (2.1 g, 3.4 mmol) and palladium acetate (516 mg, 2.3 mmol). The resulting mixture was heated at 100° C. under an atmosphere of argon overnight. The mixture was allowed to cool, charcoal was added and the mixture stirred at room temperature for 30 minutes. The solids were then removed by filtration through celite and the residue washed with ethyl acetate. The filtrate was then reduced in vacuo and the residue dissolved in 2M aqueous hydrochloric acid and ethyl acetate added. A yellow solid formed that was immiscible in both phases so the mixture was filtered and the solid washed with ethyl acetate. The biphasic filtrate was then separated and the aqueous layer washed with more ethyl acetate. The aqueous was then basified with 0.880 ammonia and the yellow solid collected by filtration added. The resulting basified aqueous solution was then extracted with dichloromethane (×2) and the combined dichloromethane layers dried over anhydrous magnesium sulfate, filtered and reduced in vacuo. The residue was then purified by chromatography on silica gel (gradient 0 to 15% methanol in dichloromethane) to afford the title product. MS (ES+) m/e 342 [M+H]$^+$.

Step 3: 5-(cis-3,5-Dimethyl-1-piperazinyl)-2-[(phenylmethyl)oxyl aniline (D39)

A mixture of cis-3,5-dimethyl-1-{3-nitro-4-[(phenylmethyl)oxy]phenyl}piperazine (3.7 g, 10.8 mmol) in methanol (60 ml) was treated with iron powder (3.03 g, 54.3 mmol) and the resulting mixture heated to 50° C. under an atmosphere of argon. After 15 minutes, a solution of ammonium chloride (4.64 g, 86.7 mmol) in water (30 ml) was added and the resulting mixture heated to 70° C. and kept at this temperature for 17 hours. The mixture was then allowed to cool over 1.5 hours and was then filtered through celite, washing with methanol and the filtrate reduced in vacuo. The residue was re-suspended in methanol, filtered again and the filtrate reduced and the residue purified by chromatography on silica gel (gradient: dichloromethane to dichloromethane:methanol 25:1 to 8.5:1.5) to give a brown residue which partially solidified on standing overnight. Trituration with diethyl ether afforded the title product (D39). MS (ES+) m/e 312 [M+H]$^+$.

Description 40

4-Bromo-N-{5-(cis-3,5-dimethyl-1-piperazinyl)-2-[(phenylmethyl)oxy]phenyl}benzenesulfonamide (D40)

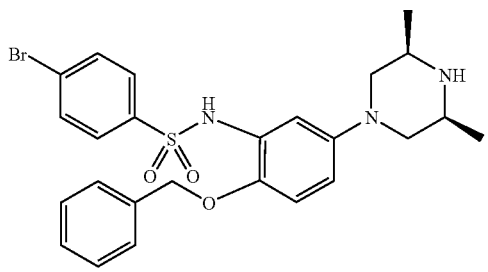

A solution of 5-(cis-3,5-dimethyl-1-piperazinyl)-2-[(phenylmethyl)oxy]aniline (D39) (500 mg, 1.61 mmol) in dichloromethane (8 ml) and pyridine (8 ml) was added 4-bromobenzenesulfonyl chloride (820 mg, 3.21 mmol) and the resulting mixture stirred at room temperature, under an atmosphere of argon for 2 hours. The mixture was then reduced in vacuo, azeotroped with methanol and the residue partitioned between dichloromethane (75 ml) and saturated aqueous sodium hydrogen carbonate (75 ml). The layers were separated, the aqueous re-extracted with dichloromethane (50 ml) and the combined organic layers washed with brine (125 ml), dried over anhydrous magnesium sulphate, filtered and reduced in vacuo. The residue was purified by chromatography on silica gel (gradient: dichloromethane:methanol 25:1 to 10:1) to afford the title compound (D40). MS (ES+) m/e 530/532 [M+H]$^+$.

Description 41

4-Bromo-N-{5-(cis-3,5-dimethyl-1-piperazinyl)-2-[(phenylmethyl)oxy]phenyl}-3-fluorobenzenesulfonamide (D41)

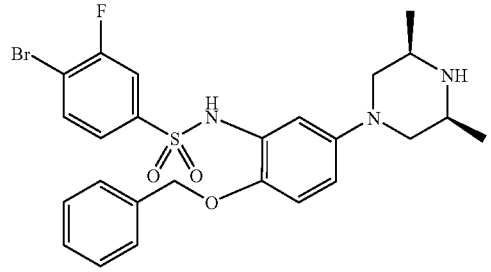

The title compound (D41) was prepared using a similar method to that described for 4-Bromo-N-{5-(cis-3,5-dimethyl-1-piperazinyl)-2-[(phenylmethyl)oxy]phenyl}benzenesulfonamide (D40) substituting 4-bromo-3-fluorobenzenesulfonyl chloride for 4-bromobenzenesulfonyl chloride. MS (ES+) m/e 548/550 [M+H]$^+$.

Description 42

5-Bromo-N-{5-(cis-3,5-dimethyl-1-piperazinyl)-2-[(phenylmethyl)oxy]phenyl}-2-thiophenesulfonamide (D42)

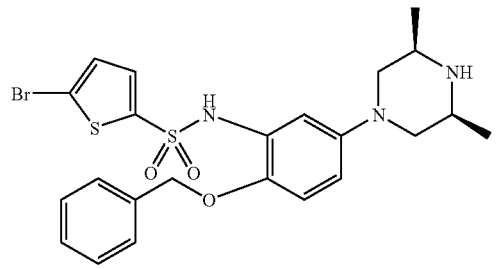

A solution of 5-(cis-3,5-dimethyl-1-piperazinyl)-2-[(phenylmethyl)oxy]aniline (D39) (300 mg, 0.96 mmol) in dichloromethane (5 ml) and pyridine (5 ml) was added 5-bromo-2-thiophenesulfonyl chloride (505 mg, 1.93 mmol) and the mixture stirred at room temperature for 4 hours. The mixture was then reduced in vacuo and the residue purified by SCX (eluting with methanol then ammonia 2M in methanol). The appropriate fractions were combined and reduced and the residue purified by trituaration with methanol to afford the title compound (D42). MS (ES+) m/e 536/538 [M+H]$^+$.

Descriptions 43-46

Descriptions 43-46 (D43-D46) were prepared from the appropriate aryl halide and boronic acid indicated in the table using a similar method to that described for Examples 126-196.

| Description | Aryl Halide | Boronic acid | MS [M + H]$^+$ |
|---|---|---|---|
| N-{5-(cis-3,5-Dimethyl-1-piperazinyl)-2-[(phenylmethyl)oxy]phenyl}-4-(5-methyl-2-furanyl)benzenesulfonamide (D43) | D40 | (5-Methyl-2-furanyl)boronic acid | 532 |
| N-{5-(cis-3,5-Dimethyl-1-piperazinyl)-2-[(phenylmethyl)oxy]phenyl}-4-(2-furanyl)benzenesulfonamide (D44) | D40 | 2-Furanylboronic acid | 518 |

| Description | Aryl Halide | Boronic acid | MS [M + H]+ |
|---|---|---|---|
| N-{5-(cis-3,5-Dimethyl-1-piperazinyl)-2-[(phenylmethyl)oxy]phenyl}-3-fluoro-4-(5-methyl-2-furanyl)benzenesulfonamide (D45) | D41 | (5-Methyl-2-furanyl)boronic acid | 550 |
| N-{5-(cis-3,5-Dimethyl-1-piperazinyl)-2-[(phenylmethyl)oxy]phenyl}-5-(2-fluorophenyl)-2-thiophenesulfonamide (D46) | D42 | (2-Fluorophenyl)boronic acid | 552 |

Description 47

Bis{4-[(phenylmethyl)oxy]phenyl}disulfide (D47)

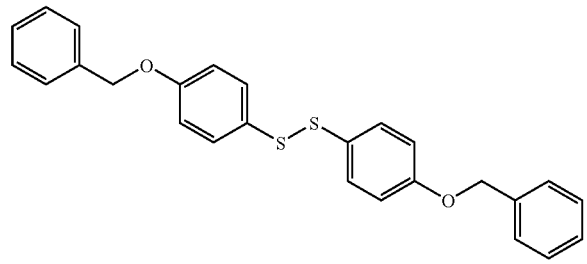

To solid potassium carbonate (11.59 g, 83.89 mmol) was added 4,4'-dithiodiphenol (7.00 g, 27.96 mmol), as a solid under argon, followed by N,N-dimethylformamide (130 ml). The stirred suspension was then heated to 80° C. over 2.25 h. Benzyl chloride (7.24 ml, 62.91 mmol) was then added over 2-3 minutes and the mixture stirred at 80° C. overnight. The mixture was then allowed to cool slowly to room temperature over the weekend. The resulting mixture was then poured into water (800 ml) and extracted with dichloromethane (3×250 ml). The organic extracts were combined and dried over sodium sulfate, filtered and evaporated to give a pale yellow solid which was tritureated with hot methanol (80 ml) which was allowed to cool slowly overnight to afford the title compound (D47). 1H-NMR (CDCl$_3$) d 7.43-7.33 (14H, m), 6.90 (4H, dd, J 6.8 Hz, 2.0 Hz), 5.05 (4H, s).

Description 48

4-[(Phenylmethyl)oxy]benzenesulfonyl chloride (D48)

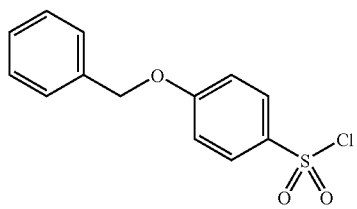

To a suspension of bis{4-[(phenylmethyl)oxy]phenyl}disulfide (D47) (10.87 g, 25.24 mmol) in acetic acid (290 ml) at room temperature under argon was added N-chlorosuccinimide (16.85 g, 126.2 mmol) potion-wise over 10 minutes and the resulting mixture allowed to stir at room temperature overnight. The mixture was then poured into water (1200 ml) to give an emulsion which was extracted with dichloromethane (3×500 ml). The aqueous fraction was then filtered over celite and the solid washed with dichloromethane (500 ml). The emulsion was still present so the aqueous layer was stirred with solid sodium chloride and then re-extracted with dichloromethane (500 ml). All the dichloromethane layers were combined and dried over sodium sulfate, filtered, evaporated and dried to give to afford the title compound. 1H-NMR (CDCl$_3$) d 8.00-7.96 (2H, m), 7.43-7.36 (5H, m), 7.13-7.10 (2H, m), 5.18 (2H, s).

Description 49

Pentafluorophenyl 4-[(phenylmethyl)oxy]benzenesulfonate (D49)

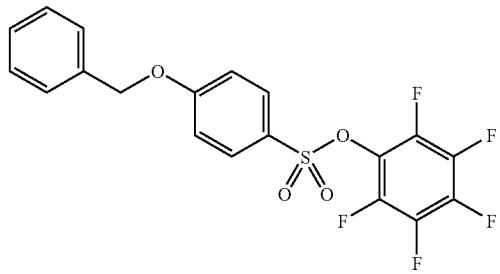

To a stirred solution of 4-[(phenyhnethyl)oxy]benzenesulfonyl chloride (D48) (13.77 g, 48.70 mmol) in dichloromethane (265 ml) was added triethylamine (9.16 ml, 65.75 mmol) under argon and the mixture cooled to −15° C. A solution of pentafluorophenol (9.86 g, 53.57 mmol) in dichloromethane (20 ml+20 ml wash) was then added quickly and the reaction allowed to wami slowly to room temperature over 1.75 h. Hydrochloric acid (2M, 250 ml) was then added and the mixture stirred for 20-30 min and the layers separated. The aqueous layer was then re-extracted with dichloromethane (100 ml) and the combined organic fractions washed with saturated aqueous sodium hydrogen carbonate (200 ml). The layers were separated and the aqueous re-extracted with dichloromethane (100 ml). All the dichloromethane layers were combined and dried over sodium sulfate, filtered and evaporated. The resulting solid was then dissolved in dichloromethane (40 ml) with warming, and allowed to cool and then purified by chromatography on silica gel eluting with 10-15% diethyl ether/hexane to afford the title compound (D49). 1H-NMR (d6-DMSO) d 7.97-7.94 (2H, m), 7.50-7.31 (7H, m), 5.29 (2H, s).

Example 1

N-[3-(cis-3,5-Dimethyl-1-piperazinyl)-4-(methyloxy)phenyl]-5-(2-pyridinyl)-2-thiophenesulfonamide (E1)

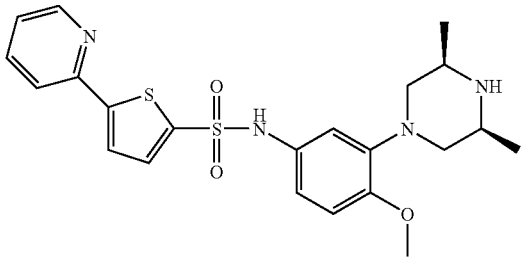

3-(cis-3,5-Dimethyl-1-piperazinyl)-4-(methyloxy)aniline (D2) (100 mg, 0.42 mmol) in dichloromethane (10 ml) was stirred with morpholinomethyl-polystyrene HL resin (320 mg, 4 mmol/g loading, 1.28 mmol) at ambient temperature. 5-(2-Pyridinyl)-2-thiophenesulfonyl chloride (110 mg, 0.4 mmol) was added and the mixture stirred for 18 hours. Argopore-trisamine scavenger resin (100 mg, 4 mmol/g loading, 0.4 mmol) was then added and the mixture stirred for a further 30 minutes. The resin was removed by filtration, washed with dichloromethane and the filtrate concentrated in vacuo. The residue was purified by column chromatography (1:19 2M ammonia in methanol: dichloromethane) to afford the title product (E1). MS (ES+) 459 [M+H]$^+$.

Examples 2-10

Examples 2-10 (E2-E10) were prepared using an analogous method to that described for Example 1 (E1) from 3-(cis-3,5-dimethyl-1-piperazinyl)-4-(methyloxy)aniline (D2) and the appropriate sulfonyl chloride indicated in the table:

Example 11

N-[3-(cis-3,5-Dimethyl-1-piperazinyl)-4-(methyloxy)phenyl]-4-(2-thienyl)benzenesulfonamide (E11)

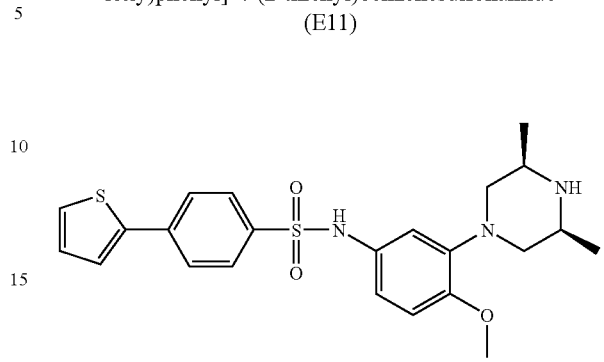

A solution of 3-(cis-3,5-dimethyl-1-piperazinyl)-4-(methyloxy)aniline (D2) (117 mg, 0.5 mmol) in pyridine:dichloromethane (1:1, 4 ml) was treated with a solution 4-(2-thienyl)benzenesulfonyl chloride (WO 9827069) (143 mg, 0.55 mmol) in dichloromethane (2 ml). The solution was stirred at room temperature for 24 hours, quenched with methanol (2 ml) and concentrated in vacuo. The residue was dissolved in dichloromethane and washed with water (×3). The organic phase was applied to a SCX cartridge (Varian bond-elute, 5 g) and washed with methanol and 2M ammonia in methanol. The combined basic fractions were concentrated in vacuo and the resulting residue was purified by column chromatography (dichloromethane to 1:4 2M ammonia in methanol:dichloromethane) to afford the title product (E11). MS (ES+) m/e 458 [M+H]$^+$.

| Example | Sulfonyl chloride | LC/MS (M + H)+ |
|---|---|---|
| 4-[(3-Chloro-2-cyanophenyl)oxy]-N-[3-(cis-3,5-dimethyl-1-piperazinyl)-4-(methyloxy)phenyl]benzenesulfonamide (E2) | 4-[(3-Chloro-2-cyanophenyl)oxy]benzenesulfonyl chloride | 527/529 |
| 5-Chloro-N-[3-(cis-3,5-dimethyl-1-piperazinyl)-4-(methyloxy)phenyl]-3-methyl-1-benzothiophene-2-sulfonamide (E3) | 5-Chloro-3-methyl-1-benzothiophene-2-sulfonyl chloride | 480/482 |
| 5-(Dimethylamino)-N-[3-(cis-3,5-dimethyl-1-piperazinyl)-4-(methyloxy)phenyl]-1-naphthalenesulfonamide (E4) | 5-(Dimethylamino)-1-naphthalenesulfonyl chloride | 469 |
| N-[3-(cis-3,5-Dimethyl-1-piperazinyl)-4-(methyloxy)phenyl]-1-naphthalenesulfonamide (E5) | 1-Naphthalenesulfonyl chloride | 426 |
| (E)—N-[3-(cis-3,5-Dimethyl-1-piperazinyl)-4-(methyloxy)phenyl]-2-phenylethenesulfonamide (E6) | (E)-2-Phenylethenesulfonyl chloride | 402 |
| 5-Chloro-N-[3-(cis-3,5-dimethyl-1-piperazinyl)-4-(methyloxy)phenyl]-1-benzothiophene-2-sulfonamide (E7) | 5-Chloro-1-benzothiophene-2-sulfonyl chloride (U.S. Pat. No. 5,731,315) | 466/468 |
| N-[3-(cis-3,5-Dimethyl-1-piperazinyl)-4-(methyloxy)phenyl]-4-(phenyloxy)benzenesulfonamide (E8) | 4-(Phenyloxy)benzenesulfonyl chloride | 468 |
| N-[3-(cis-3,5-Dimethyl-1-piperazinyl)-4-(methyloxy)phenyl]-8-quinolinesulfonamide (E9) | 8-Quinolinesulfonyl chloride | 427 |
| N-[3-(cis-3,5-Dimethyl-1-piperazinyl)-4-(methyloxy)phenyl]thieno[2,3-b]pyridine-2-sulfonamide (E10) | Thieno[2,3-b]pyridine-2-sulfonyl chloride (EP 271273) | 433 |

Example 12

Example 12 (E12) was prepared using an analogous method to that described for Example 11 (E11) from 3-(cis-3,5-dimethyl-1-piperazinyl)-4-(methyloxy)aniline (D2) and the appropriate sulfonyl chloride indicated in the table:

| Example | Sulfonyl Chloride | LC/MS (M + H+) |
| --- | --- | --- |
| 8-Chloro-N-[3-(cis-3,5-dimethyl-1-piperazinyl)-4-(methyloxy)phenyl]-1-naphthalenesulfonamide (E12) | 8-Chloro-1-naphthalenesulfonyl chloride (EP 511826) | 460/462 |

Examples 13-16

Examples 13-16 (E13-E16) were prepared using an analogous method to that described for Example 1 (E1) from 5-(cis-3,5-dimethyl-1-piperazinyl)-2-(methyloxy)aniline (D4) and the appropriate sulfonyl chloride indicated in the table:

| Example | Sulfonyl Chloride | LC/MS (M + H+) |
| --- | --- | --- |
| N-[5-(cis-3,5-Dimethyl-1-piperazinyl)-2-(methyloxy)phenyl]-5-(2-pyridinyl)-2-thiophenesulfonamide (E13) | 5-(2-Pyridinyl)-2-thiophenesulfonyl chloride | 459 |
| 4-[(3-Chloro-2-cyanophenyl)oxy]-N-[5-(cis-3,5-dimethyl-1-piperazinyl)-2-(methyloxy)phenyl]benzenesulfonamide (E14) | 4-[(3-Chloro-2-cyanophenyl)oxy]benzenesulfonyl chloride | 527/529 |
| N-[5-(cis-3,5-Dimethyl-1-piperazinyl)-2-(methyloxy)phenyl]-4-(1H-pyrazol-1-yl)benzenesulfonamide (E15) | 4-(1H-Pyrazol-1-yl)benzenesulfonyl chloride | 442 |
| 5-Chloro-N-[5-(cis-3,5-dimethyl-1-piperazinyl)-2-(methyloxy)phenyl]-3-methyl-1-benzothiophene-2-sulfonamide (E16) | 5-Chloro-3-methyl-1-benzothiophene-2-sulfonyl chloride | 480/482 |

Example 17

N-[5-(cis-3,5-Dimethyl-1-piperazinyl)-2-(methyloxy)phenyl]-4-(2-thienyl)benzenesulfonamide (E17)

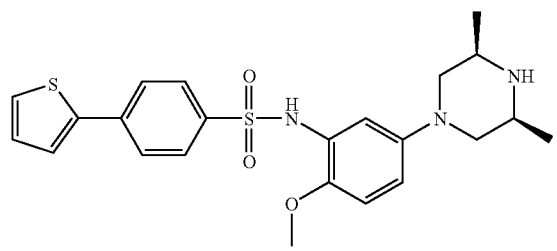

A solution of 5-(cis-3,5-dimethyl-1-piperazinyl)-2-(methyloxy)aniline (D4) (200 mg, 0.85 mmol) in pyridine (5 ml) was treated 4-(2-thienyl)benzenesulfonyl chloride (WO 9827069) (258 mg, 1.0 mmol). The solution was stirred at room temperature for 24 hours and concentrated in vacuo. The residue was co-evaporated with methanol and toluene (×3). The residue was dissolved in dichloromethane and washed with saturated sodium bicarbonate solution. The organic phase was washed with water, brine, dried over anhydrous magnesium sulfate and concentrated in vacuo. The residue was purified by column chromatography (1:40 to 1:20 2M ammonia in methanol:dichloromethane) to afford the title product (E17). MS (ES+) m/e 458 [M+H]+.

Examples 18-22

Examples 18-22 (E18-E22) were prepared using an analogous method to that described for Example 17 (E17) from 3-(cis-3,5-dimethyl-1-piperazinyl)-4-(methyloxy)aniline (D2) and the appropriate sulfonyl chloride indicated in the table:

| Example | Sulfonyl Chloride | LC/MS (M + H+) |
| --- | --- | --- |
| N-[3-(cis-3,5-Dimethyl-1-piperazinyl)-4-(methyloxy)phenyl]-2-naphthalenesulfonamide (E18) | 2-Naphthalenesulfonyl chloride | 426 |
| N-[3-(cis-3,5-Dimethyl-1-piperazinyl)-4-(methyloxy)phenyl]-4-(1H-pyrazol-1-yl)benzenesulfonamide (E19) | 4-(1H-Pyrazol-1-yl)benzenesulfonyl chloride | 442 |
| N-[3-(cis-3,5-Dimethyl-1-piperazinyl)-4-(methyloxy)phenyl]-6-(3-thienyl)-2-pyridinesulfonamide (E20) | 6-(3-Thienyl)-2-pyridinesulfonyl chloride (Description 10) | 459 |
| N-[3-(cis-3,5-Dimethyl-1-piperazinyl)-4-(methyloxy)phenyl]-5-(6-methyl-2-pyridinyl)-2-thiophenesulfonamide (E21) | 5-(6-Methyl-2-pyridinyl)-2-thiophenesulfonyl chloride (Description 12) | 473 |
| N-[3-cis-3,5-Dimethyl-1-piperazinyl)-4-(methyloxy)phenyl]-4-iodobenzenesulfonamide (E22) | 4-Iodobenzenesulfonyl chloride | 502 |

Example 23

N-[3-(cis-3,5-Dimethyl-1-piperazinyl)-4-(methyloxy)phenyl]-4-(2-oxo-1-pyrrolidinyl)benzenesulfonamide (E23)

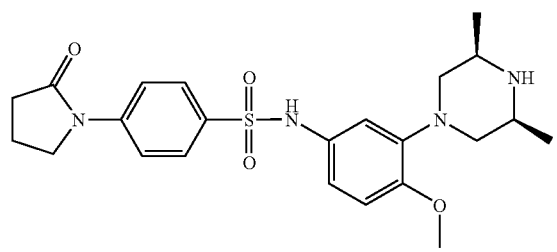

A mixture of N-[3-cis-3,5-dimethyl-1-piperazinyl)-4-(methyloxy)phenyl]-4-iodobenzenesulfonamide (E22) (170 mg, 0.34 mmol), 2-pyrrolidinone (0.05 ml, 0.68 mmol), potassium carbonate (169 mg, 1.22 mmol), copper (I) iodide (19 mg, 0.1 mmol) and N,N'-dimethyl-1,2-ethanediamine (0.01 ml, 0.1 mmol) in dioxane (3 ml) was heated at 140° C. in a microwave reactor for 50 min. The reaction mixture was applied to a SCX cartridge (Varian bond-elute) and washed with methanol and 2M ammonia in methanol. The combined basic fractions were concentrated in vacuo and the resulting residue was purified by column chromatography (dichloromethane to 1:7 2M ammonia in methanol:dichloromethane) to afford the title product (E23). MS (ES+) m/e 459 [M+H]$^+$.

Examples 24-27

Examples 24-27 (E24-E27) were prepared using an analogous method to that described for Example 17 (E17) from 1-[2-amino-4-(cis-3,5-dimethyl-1-piperazinyl)phenyl]ethanone (D6) and the appropriate sulfonyl chloride indicated in the table:

| Example | Sulfonyl Chloride | LC/MS (M + H$^+$) |
|---|---|---|
| N-[2-Acetyl-5-(cis-3,5-dimethyl-1-piperazinyl)phenyl]-4-[(3-chloro-2-cyanophenyl)oxy]benzenesulfonamide (E24) | 4-[(3-Chloro-2-cyanophenyl)oxy]benzene sulfonyl chloride | 539/541 |
| N-[2-Acetyl-5-(cis-3,5-dimethyl-1-piperazinyl)phenyl]-5-(2-pyridinyl)-2-thiophenesulfonamide (E25) | 5-(2-Pyridinyl)-2-thiophenesulfonyl chloride | 471 |
| N-[2-Acetyl-5-(cis-3,5-dimethyl-1-piperazinyl)phenyl]-4-(2-thienyl)benzenesulfonamide (E26) | 4-(2-Thienyl)benzenesulfonyl chloride | 470 |
| N-[2-Acetyl-5-(cis-3,5-dimethyl-1-piperazinyl)phenyl]-4-(1H-pyrazol-1-yl)benzenesulfonamide (E27) | 4-(1H-Pyrazol-1-yl)benzenesulfonyl chloride | 454 |

Examples 28-30

Examples 28-30 (E28-E30) were prepared using similar methods to that described for Example 1 (E1) from 3-(cis-3,5-dimethyl-1-piperazinyl)-4-(methyloxy)aniline (D2) and the appropriate sulfonyl chloride indicated in the table:

| Example | Sulfonyl Chloride | LC/MS (M + H$^+$) |
|---|---|---|
| N-[3-(cis-3,5-Dimethyl-1-piperazinyl)-4-(methyloxy)phenyl]-3,5-dimethyl-4-isoxazolesulfonamide (E28) | 3,5-Dimethyl-4-isoxazolesulfonyl chloride | 395 |
| 2,3-Dichloro-N-[3-(cis-3,5-dimethyl-1-piperazinyl)-4-(methyloxy)phenyl]benzenesulfonamide (E29) | 2,3-Dichlorobenzenesulfonyl chloride | 444/446 |
| 3,4-Dichloro-N-[3-(cis-3,5-dimethyl-1-piperazinyl)-4-(methyloxy)phenyl]benzenesulfonamide (E30) | 3,4-Dichlorobenzenesulfonyl chloride | 444/446 |

Examples 31-38

Examples 31-38 (E31-E38) were prepared using similar methods to that described below from 5-(cis-3,5-dimethyl-1-piperazinyl)-2-(methyloxy)aniline (D4) and the appropriate sulfonyl chloride listed in the table:

5-(cis-3,5-Dimethyl-1-piperazinyl)-2-(methyloxy)aniline (D4) (100 mg, 0.42 mmol) in dichloromethane (10 ml) was stirred with morpholinomethyl-polystyrene HL resin (315 mg, 4 mmol/g loading, 1.26 mmol) at ambient temperature. The appropriate sulfonyl chloride (0.51 mmol) was then added and the mixture stirred at room temperature overnight. Argopore-trisamine scavenger resin (105 mg, 4 mmol/g loading, 0.42 mmol) was then added and the mixture stirred for a further 2.5 hours. The resin was removed by filtration and the filtrate concentrated in vacuo. The residue was then purified further by chromatography on silica gel eluting with (0 to 10% methanol in dichloromethane) followed by further purification by mass directed autoprep HPLC, and/or using an SCX ion exchange cartridge (Varian bond-elute) eluting with methanol followed by ammonia (2M in methanol), where appropriate, to afford the desired product which was characterized as either the free base or hydrochloride salt.

| Example | Sulfonyl Chloride | MS [M + H]$^+$ |
|---|---|---|
| N-[5-(cis-3,5-Dimethyl-1-piperazinyl)-2-(methyloxy)phenyl]-2-naphthalenesulfonamide (E31) | 2-Naphthalenesulfonyl chloride | 426 |
| N-[5-(cis-3,5-Dimethyl-1-piperazinyl)-2-(methyloxy)phenyl]-1-naphthalenesulfonamide (E32) | 1-Naphthalenesulfonyl chloride | 426 |

-continued

| Example | Sulfonyl Chloride | MS [M + H]+ |
|---|---|---|
| N-[5-(cis-3,5-Dimethyl-1-piperazinyl)-2-(methyloxy)phenyl]-4-(phenyloxy)benzenesulfonamide (E33) | 4-(Phenyloxy)benzenesulfonyl chloride | 468 |
| N-[5-(cis-3,5-Dimethyl-1-piperazinyl)-2-(methyloxy)phenyl]-4-iodobenzenesulfonamide (E34) | 4-Iodobenzenesulfonyl chloride | 502 |
| N-[5-(cis-3,5-Dimethyl-1-piperazinyl)-2-(methyloxy)phenyl]-8-quinolinesulfonamide (E35) | 8-Quinolinesulfonyl chloride | 427 |
| 3,4-Dichloro-N-[5-(cis-3,5-dimethyl-1-piperazinyl)-2-(methyloxy)phenyl]benzenesulfonamide (E36) | 3,4-Dichlorobenzenesulfonyl chloride | 444/446 |
| 2,3-Dichloro-N-[5-(cis-3,5-dimethyl-1-piperazinyl)-2-(methyloxy)phenyl]benzenesulfonamide (E37) | 2,3-Dichlorobenzenesulfonyl chloride | 444/446 |
| (E)-N-[5-(cis-3,5-Dimethyl-1-piperazinyl)-2-(methyloxy)phenyl]-2-phenylethenesulfonamide (E38) | (E)-2-Phenylethenesulfonyl chloride | 402 |

Examples 39-54

Examples 39-54 (E39-E54) were prepared using similar methods to that described below from the appropriate aniline and sulfonyl chloride listed in the table: The appropriate aniline (1 eq) in pyridine (0.1-0.4M) was treated with the appropriate sulfonyl chloride (1.5 eq) and the resulting mixture stirred at room temperature until the reaction was complete (1 hour—overnight). The mixture was then concentrated in vacuo and the residue partitioned between dichloromethane and saturated aqueous sodium bicarbonate solution and the layers separated. The aqueous layer was re-extracted with dichloromethane (×2) and the combined organic layers washed with brine, dried over anhydrous magnesium sulfate, filtered and concentrated in vacuo. The residue was then purified, where appropriate, using an SCX ion exchange cartridge (Varian bond-elute) eluting with methanol followed by ammonia (1M in methanol) and then ammonia (2M in methanol) and the appropriate fractions combined and concentrated in vacuo to afford a crude product. Further purification by mass directed autoprep HPLC and/or by trituration (with methanol or DMSO/MeCN) or by chromatography on silica gel eluting with (0 to 10% methanol in dichloromethane) afforded the desired product which was characterized either as the free base or hydrochloride salt.

| Example | Sulfonyl Chloride | Aniline | MS [M + H]+ |
|---|---|---|---|
| N-[4-Cyano-3-(cis-3,5-dimethyl-1-piperazinyl)phenyl]-4-(2-thienyl)benzenesulfonamide (E39) | 4-(2-Thienyl)benzenesulfonyl chloride (using D31) | D28 | 453 |
| N-[5-(cis-3,5-Dimethyl-1-piperazinyl)-2-(methyloxy)phenyl]-5-fluoro-3-methyl-1-benzothiophene-2-sulfonamide (E40) | 5-Fluoro-3-methyl-1-benzothiophene-2-sulfonyl chloride | D4 | 464 |
| 5'-Chloro-N-[5-(cis-3,5-dimethyl-1-piperazinyl)-2-(methyloxy)phenyl]-2,2'-bithiophene-5-sulfonamide (E41) | 5'-Chloro-2,2'-bithiophene-5-sulfonyl chloride (WO02100830) | D4 | 498/500 |
| 2-Bromo-N-[5-(cis-3,5-dimethyl-1-piperazinyl)-2-(methyloxy)phenyl]benzenesulfonamide (E42) | 2-Bromobenzenesulfonyl chloride | D4 | 454/456 |
| N-[3-(cis-3,5-Dimethyl-1-piperazinyl)-4-(methyloxy)phenyl]-5-(1,3-oxazol-5-yl)-2-thiophenesulfonamide (E43) | 5-(1,3-Oxazol-5-yl)-2-thiophenesulfonyl chloride | D2 | 449 |
| N-[3-(cis-3,5-Dimethyl-1-piperazinyl)phenyl]-4-(2-thienyl)benzenesulfonamide (E44) | 4-(2-Thienyl)benzenesulfonyl chloride (using D31) | D21 | 428 |
| 4-(5-Chloro-2-thienyl)-N-[3-(cis-3,5-dimethyl-1-piperazinyl)phenyl]benzenesulfonamide (E45) | 4-(5-Chloro-2-thienyl)benzenesulfonyl chloride (using D31) | D21 | 462/464 |
| N-[3-(cis-3,5-Dimethyl-1-piperazinyl)phenyl]-4-(1H-pyrazol-1-yl)benzenesulfonamide (E46) | 4-(1H-Pyrazol-1-yl)benzenesulfonyl chloride | D21 | 412 |
| 5-Chloro-N-[3-(cis-3,5-dimethyl-1-piperazinyl)-4-(methyloxy)phenyl]-2-naphthalenesulfonamide (E47) | 5-Chloro-2-naphthalenesulfonyl chloride | D2 | 460/462 |

-continued

| Example | Sulfonyl Chloride | Aniline | MS [M + H]+ |
|---|---|---|---|
| N-[3-(cis-3,5-Dimethyl-1-piperazinyl)-4-(methyloxy)phenyl]-4-biphenylsulfonamide (E48) | 4-Biphenylsulfonyl chloride | D2 | 452 |
| 4-Bromo-N-[3-(cis-3,5-dimethyl-1-piperazinyl)-4-(methyloxy)phenyl]-3-methylbenzenesulfonamide (E49) | 4-Bromo-3-methylbenzenesulfonyl chloride | D2 | 468/470 |
| 4-Bromo-N-[3-(cis-3,5-dimethyl-1-piperazinyl)-4-(methyloxy)phenyl]-3-fluorobenzenesulfonamide (E50) | 4-Bromo-3-fluorobenzenesulfonyl chloride | D2 | 472/474 |
| 4-Bromo-2-chloro-N-[3-(cis-3,5-dimethyl-1-piperazinyl)-4-(methyloxy)phenyl]benzenesulfonamide (E51) | 4-Bromo-2-chlorobenzenesulfonyl chloride | D2 | 488/490/492 |
| 4-Bromo-N-[3-(cis-3,5-dimethyl-1-piperazinyl)-4-(methyloxy)phenyl]-2-fluorobenzenesulfonamide (E52) | 4-Bromo-2-fluorobenzenesulfonyl chloride | D2 | 472/474 |
| N-[5-(cis-3,5-Dimethyl-1-piperazinyl)-4-fluoro-2-(methyloxy)phenyl]-4-(2-thienyl)benzenesulfonamide (E53) | 4-(2-Thienyl)benzenesulfonyl chloride (WO9827069) | D18 | 476 |
| N-[5-(cis-3,5-Dimethyl-1-piperazinyl)-4-fluoro-2-(methyloxy)phenyl]-5-(2-pyridinyl)-2-thiophenesulfonamide (E54) | 5-(2-Pyridinyl)-2-thiophenesulfonyl chloride | D18 | 477 |

Examples 55-68

Examples 55-68 (E55-E68) were prepared using methods similar to that described below from the appropriate aniline and sulfonyl chloride listed in the table:

The appropriate aniline (1 eq) in pyridine (ca. 0.1M) was treated with the appropriate sulfonyl chloride (1.2-1.9 eq) and the resulting mixture stirred at room temperature until the reaction was complete (2 hours—overnight). The mixture was then concentrated in vacuo and the residue partitioned between dichloromethane and saturated aqueous sodium bicarbonate solution and the layers separated using a hydrophobic phase-separation cartridge. The organic layer was washed with additional saturated aqueous sodium bicarbonate solution and then concentrated in vacuo. The residue was then purified using an SCX ion exchange cartridge (Varian bond-elute) eluting with methanol followed by ammonia (1 to 2M in methanol) or by chromatography on silica gel eluting with (0 to 10% methanol in dichloromethane) to afford a crude product. Further purification by mass directed autoprep HPLC or trituration (with dichloromethane) afforded the desired product which was characterized as either the free base or hydrochloride salt.

| Example | Sulfonyl Chloride | Aniline | MS [M + H]+ |
|---|---|---|---|
| 5-Chloro-N-[5-(cis-3,5-dimethyl-1-piperazinyl)-2-(methyloxy)phenyl]-1-benzothiophene-2-sulfonamide (E55) | 5-Chloro-1-benzothiophene-2-sulfonyl chloride (U.S. Pat. No. 5,731,315) | D4 | 466/468 |
| N-[5-(cis-3,5-Dimethyl-1-piperazinyl)-2-(methyloxy)phenyl]-4-(1,3-oxazol-5-yl)benzenesulfonamide (E56) | 4-(1,3-Oxazol-5-yl)benzenesulfonyl chloride | D4 | 443 |
| N-[3-(cis-3,5-Dimethyl-1-piperazinyl)-4-(methyloxy)phenyl]-4-(1,3-oxazol-5-yl)benzenesulfonamide (E57) | 4-(1,3-Oxazol-5-yl)benzenesulfonyl chloride | D2 | 443 |
| N-[3-(cis-3,5-Dimethyl-1-piperazinyl)-4-(methyloxy)phenyl]-4-methyl-3,4-dihydro-2H-1,4-benzoxazine-7-sulfonamide (E58) | 4-Methyl-3,4-dihydro-2H-1,4-benzoxazine-7-sulfonyl chloride | D2 | 447 |
| N-[3-(cis-3,5-Dimethyl-1-piperazinyl)-4-(methyloxy)phenyl]-4-(1-methylethyl)benzenesulfonamide (E59) | 4-(1-Methylethyl)benzenesulfonyl chloride | D2 | 418 |
| N-[5-(cis-3,5-Dimethyl-1-piperazinyl)-2-(methyloxy)phenyl]-3-{[4-(methyloxy)phenyl]oxy}benzenesulfonamide (E60) | 3-{[4-(Methyloxy)phenyl]oxy}benzenesulfonyl chloride | D4 | 498 |
| N-[5-(cis-3,5-Dimethyl-1-piperazinyl)-2-(methyloxy)phenyl]-1-benzothiophene-3-sulfonamide (E61) | 1-Benzothiophene-3-sulfonyl chloride | D4 | 432 |
| N-[5-(cis-3,5-Dimethyl-1-piperazinyl)-2-(methyloxy)phenyl]-5-(1,3-oxazol-5-yl)-2-thiophenesulfonamide (E62) | 5-(1,3-Oxazol-5-yl)-2-thiophenesulfonyl chloride | D4 | 449 |

| Example | Sulfonyl Chloride | Aniline | MS [M + H]+ |
|---|---|---|---|
| N-[5-(cis-3,5-Dimethyl-1-piperazinyl)-2-(methyloxy)phenyl]-4-biphenylsulfonamide (E63) | 4-Biphenylsulfonyl chloride | D4 | 452 |
| N-[3-(cis-3,5-Dimethyl-1-piperazinyl)phenyl]-1-naphthalenesulfonamide (E64) | 1-Naphthalenesulfonyl chloride | D21 | 396 |
| N-[3-(cis-3,5-Dimethyl-1-piperazinyl)phenyl]-2-naphthalenesulfonamide (E65) | 2-Naphthalenesulfonyl chloride | D21 | 396 |
| 2,3-Dichloro-N-[3-(cis-3,5-dimethyl-1-piperazinyl)phenyl]benzenesulfonamide (E66) | 2,3-Dichlorobenzenesulfonyl chloride | D21 | 414/416 |
| N-[3-(cis-3,5-Dimethyl-1-piperazinyl)phenyl]-1-benzothiophene-2-sulfonamide (E67) | 1-Benzothiophene-2-sulfonyl chloride | D21 | 402 |
| N-[3-(cis-3,5-dimethyl-1-piperazinyl)phenyl]-4-(1,3-oxazol-5-yl)benzenesulfonamide (E68) | 4-(1,3-Oxazol-5-yl)benzenesulfonyl chloride | D21 | 413 |

Examples 69-81

Examples 69-81 (E69-E81) were prepared using methods similar to that described below from the appropriate aniline and sulfonyl chloride listed in the table: A solution of the appropriate aniline (1 eq) in dichloromethane (ca. 0.06-0.13M) was treated with morpholinomethyl-polystyrene HL resin (4-4.2 mmol/g loading, 2 eq) followed by the appropriate sulfonyl chloride (1.5-2.0 eq). The resulting solution was stirred room temperature for (1-2 days) and was then filtered, washing with methanol, and the filtrate concentrated in vacuo. The residue was then purified using an SCX ion exchange cartridge (Varian bond-elute) eluting with methanol followed by ammonia (0.5M to 2M in methanol). The appropriate fractions were combined and reduced in vacuo to afford a crude product which was purified further by mass directed autoprep HPLC or trituration (with diethyl ether, DMSO/MeCN or methanol) and/or by chromatography on silica gel eluting with (0 to 10% methanol in dichloromethane) to afford the desired product which was characterized as either the free base or hydrochloride salt.

| Example | Sulfonyl Chloride | Aniline | MS [M + H]+ |
|---|---|---|---|
| N-[5-(cis-3,5-Dimethyl-1-piperazinyl)-2-methylphenyl]-2-naphthalenesulfonamide (E69) | 2-Naphthalenesulfonyl chloride | D29 | 410 |
| N-[5-(cis-3,5-Dimethyl-1-piperazinyl)-2-methylphenyl]-1-naphthalenesulfonamide (E70) | 1-Naphthalenesulfonyl chloride | D29 | 410 |
| 8-Chloro-N-[5-(cis-3,5-dimethyl-1-piperazinyl)-2-(methyloxy)phenyl]-1-naphthalenesulfonamide (E71) | 8-Chloro-1-naphthalenesulfonyl chloride | D4 | 460/462 |
| 4-Bromo-N-[3-(cis-3,5-dimethyl-1-piperazinyl)-4-(methyloxy)phenyl]-2-methylbenzenesulfonamide (E72) | 4-Bromo-2-methylbenzenesulfonyl chloride | D2 | 468/470 |
| 4-Bromo-N-[5-(cis-3,5-dimethyl-1-piperazinyl)-2-(methyloxy)phenyl]-3-methylbenzenesulfonamide (E73) | 4-Bromo-3-methylbenzenesulfonyl chloride | D4 | 468/470 |
| 5-Bromo-N-[3-(cis-3,5-dimethyl-1-piperazinyl)-4-(methyloxy)phenyl]-2-thiophenesulfonamide (E74) | 5-Bromo-2-thiophenesulfonyl chloride | D2 | 460/462 |
| 4-Chloro-N-[5-(cis-3,5-dimethyl-1-piperazinyl)-2-(methyloxy)phenyl]-1-naphthalenesulfonamide (E75) | 4-Chloro-1-naphthalenesulfonyl chloride | D4 | 460/462 |
| 3-Bromo-N-[5-(cis-3,5-dimethyl-1-piperazinyl)-2-(methyloxy)phenyl]benzenesulfonamide (E76) | 3-Bromobenzenesulfonyl chloride | D4 | 454/456 |
| 5-Bromo-N-[5-(cis-3,5-dimethyl-1-piperazinyl)-2-(methyloxy)phenyl]-2-(methyloxy)benzenesulfonamide (E77) | 5-Bromo-2-(methyloxy)benzenesulfonyl chloride | D4 | 484/486 |
| 5-Bromo-N-[5-(cis-3,5-dimethyl-1-piperazinyl)-2-(methyloxy)phenyl]-4-methyl-2-thiophenesulfonamide (E78) | 5-Bromo-4-methyl-2-thiophenesulfonyl chloride (WO2004/043366) | D4 | 474/476 |

| Example | Sulfonyl Chloride | Aniline | MS [M + H]+ |
| --- | --- | --- | --- |
| N-[5-(cis-3,5-Dimethyl-1-piperazinyl)-2-(methyloxy)phenyl]-5-(1,2,3-thiadiazol-4-yl)-2-thiophenesulfonamide (E79) | 5-(1,2,3-Thiadiazol-4-yl)-2-thiophenesulfonyl chloride | D4 | 466 |
| N-[5-(cis-3,5-Dimethyl-1-piperazinyl)-2-(methyloxy)phenyl]-2,2-dimethyl-3,4-dihydro-2H-chromene-6-sulfonamide (E80) | 2,2-Dimethyl-3,4-dihydro-2H-chromene-6-sulfonyl chloride | D4 | 460 |
| 4-Bromo-N-[5-(cis-3,5-Dimethyl-1-piperazinyl)-2-methylphenyl]benzenesulfonamide (E81) | 4-Bromobenzenesulfonyl chloride | D29 | 438/440 |

Examples 82-100

Examples 82-100 (E82-E100) were prepared using methods similar to that described below from the appropriate aniline and sulfonyl chloride listed in the table:

A solution of the appropriate aniline (1 eq) in dichloromethane and pyridine (1:1, 0.07M) was treated with the appropriate sulfonyl chloride (1.2 eq) and the resulting solution stirred at room temperature overnight with more sulfonyl chloride being added if appropriate. The mixture was then concentrated in vacuo and the residue partitioned between dichloromethane and saturated aqueous sodium bicarbonate solution and the layers separated. The aqueous layer was re-extracted with dichloromethane (×2) and the combined organic layers washed with brine, dried over anhydrous magnesium sulfate, filtered and concentrated in vacuo. The crude product was then purified further by mass directed autoprep HPLC to afford the desired product which was characterized as either the free base or hydrochloride salt.

| Example | Sulfonyl Chloride | Aniline | MS [M + H]+ |
| --- | --- | --- | --- |
| 4-Bromo-N-[3-(cis-3,5-dimethyl-1-piperazinyl)-4-(methyloxy)phenyl]-2-(methyloxy)benzenesulfonamide (E82) | 4-Bromo-2-(methyloxy)benzenesulfonyl chloride (D30) | D2 | 484/486 |
| N-[5-(cis-3,5-Dimethyl-1-piperazinyl)-2-fluorophenyl]-5-(2-pyridinyl)-2-thiophenesulfonamide (E83) | 5-(2-Pyridinyl)-2-thiophenesulfonyl chloride | D13 | 447 |
| N-[5-(cis-3,5-Dimethyl-1-piperazinyl)-2-fluorophenyl]-4-biphenylsulfonamide (E84) | 4-Biphenylsulfonyl chloride | D13 | 440 |
| N-[5-(cis-3,5-Dimethyl-1-piperazinyl)-2-fluorophenyl]-4-iodobenzenesulfonamide (E85) | 4-Iodobenzenesulfonyl chloride | D13 | 490 |
| 4-Bromo-N-[5-(cis-3,5-dimethyl-1-piperazinyl)-2-fluorophenyl]-2-fluorobenzenesulfonamide (E86) | 4-Bromo-2-fluorobenzenesulfonyl chloride | D13 | 460/462 |
| 4-Bromo-2-chloro-N-[5-(cis-3,5-dimethyl-1-piperazinyl)-2-fluorophenyl]benzenesulfonamide (E87) | 4-Bromo-2-chlorobenzenesulfonyl chloride | D13 | 476/478/480 |
| 4-Bromo-N-[5-(cis-3,5-dimethyl-1-piperazinyl)-2-fluorophenyl]-2-methylbenzenesulfonamide (E88) | 4-Bromo-2-methylbenzenesulfonyl chloride | D13 | 456/458 |
| 4-Bromo-N-[5-(cis-3,5-dimethyl-1-piperazinyl)-2-fluorophenyl]-3-fluorobenzenesulfonamide (E89) | 4-Bromo-3-fluorobenzenesulfonyl chloride | D13 | 460/462 |
| N-[5-(cis-3,5-Dimethyl-1-piperazinyl)-2-fluoro-4-(methyloxy)phenyl]-4-iodobenzenesulfonamide (E90) | 4-Iodobenzenesulfonyl chloride | D19 | 520 |

-continued

| Example | Sulfonyl Chloride | Aniline | MS [M + H]+ |
|---|---|---|---|
| N-[5-(cis-3,5-Dimethyl-1-piperazinyl)-2-(ethyloxy)phenyl]-5-(2-pyridinyl)-2-thiophenesulfonamide (E91) | 5-(2-Pyridinyl)-2-thiophenesulfonyl chloride | D22 | 473 |
| N-{5-(cis-3,5-Dimethyl-1-piperazinyl)-2-[(methyloxy)methyl]phenyl}-4-biphenylsulfonamide (E92) | 4-Biphenylsulfonyl chloride | D24 | 466 |
| 7-Chloro-N-[5-(cis-3,5-dimethyl-1-piperazinyl)-2-(methyloxy)phenyl]-2,1,3-benzoxadiazole-4-sulfonamide (E93) | 7-Chloro-2,1,3-benzoxadiazole-4-sulfonyl chloride | D4 | 452/454 |
| N-[3-(cis-3,5-Dimethyl-1-piperazinyl)-4-(ethyloxy)phenyl]-4-iodobenzenesulfonamide (E94) | 4-Iodobenzenesulfonyl chloride | D27 | 516 |
| 4-(5-Chloro-2-thienyl)-N-[5-(cis-3,5-dimethyl-1-piperazinyl)-2-(methyloxy)phenyl]benzenesulfonamide (E95) | 4-(5-Chloro-2-thienyl)benzenesulfonyl chloride (using D31) | D4 | 492/494 |
| 4-(5-Chloro-2-thienyl)-N-[2-cyano-5-(cis-3,5-dimethyl-1-piperazinyl)phenyl]benzenesulfonamide (E96) | 4-(5-Chloro-2-thienyl)benzenesulfonyl chloride (using D31) | D20 | 487/489 |
| N-[2-Cyano-5-(cis-3,5-dimethyl-1-piperazinyl)phenyl]-4-(2-thienyl)benzenesulfonamide (E97) | 4-(2-Thienyl)benzenesulfonyl chloride (using D31) | D20 | 453 |
| 4-(5-Chloro-2-thienyl)-N-[5-(cis-3,5-dimethyl-1-piperazinyl)-4-fluoro-2-(methyloxy)phenyl]benzenesulfonamide (E98) | 4-(5-Chloro-2-thienyl)benzenesulfonyl chloride (using D31) | D18 | 510/512 |
| N-[5-(cis-3,5-Dimethyl-1-piperazinyl)-2-(ethyloxy)phenyl]-4-iodobenzenesulfonamide (E99) | 4-Iodobenzenesulfonyl chloride | D22 | 516 |
| N-{5-(cis-3,5-Dimethyl-1-piperazinyl)-2-[(1-methylethyl)oxy]phenyl}-4-iodobenzenesulfonamide (E100) | 4-Iodobenzenesulfonyl chloride | D23 | 530 |

Example 101

4-Bromo-N-[3-(cis-3,5-dimethyl-1-piperazinyl)-4-(methyloxy)phenyl]benzenesulfonamide (E101)

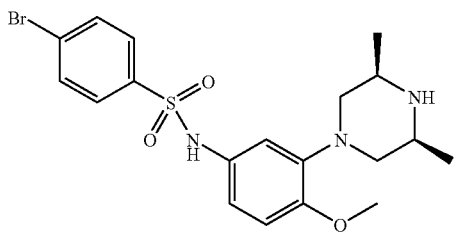

A solution of 3-(cis-3,5-dimethyl-1-piperazinyl)-4-(methyloxy)aniline (D2) (800 mg, 3.40 mmol) in dichloromethane (50 ml) was treated with morpholinomethyl-polystyrene HL resin (1.70 g, 4.0 mmol/g loading, 6.80 mmol) followed by 4-bromobenzenesulfonyl chloride (1.30 g, 5.09 mmol). The resulting solution was stirred at room temperature overnight and was then filtered, washing with methanol, and the filtrate concentrated in vacuo. The residue was then purified using an SCX ion exchange cartridge (Varian bond-elute) eluting with methanol followed by ammonia (2M in methanol). The appropriate fractions were combined and reduced in vacuo to afford a crude product which was purified further by chromatography on silica gel eluting with (0 to 20% methanol in dichloromethane) to afford the title compound (E101). MS (ES+) m/e 454/456 [M+H]+.

The hydrochloride salt of the product was prepared by dissolving the pure material from chromatography in dichloromethane and acidifying with ethereal HCl.

Example 102

4-Bromo-N-[5-(cis-3,5-dimethyl-1-piperazinyl)-2-(methyloxy)phenyl]-2-methylbenzenesulfonamide (E102)

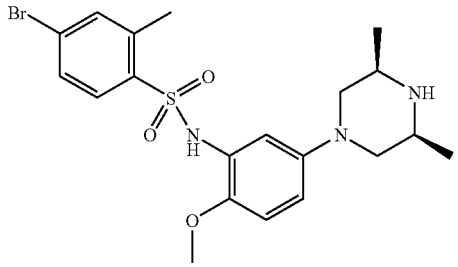

A solution of 5-(cis-3,5-dimethyl-1-piperazinyl)-2-(methyloxy)aniline (D4) (1.20 g, 5.1 mmol) in dichloromethane (35 ml) was treated with morpholinomethyl-polystyrene HL resin (2.43 g, 4.2 mmol/g loading, 10.2 mmol) followed by 4-bromo-2-methylbenzenesulfonyl chloride (2.75 g, 10.2 mmol). The resulting solution was stirred at room temperature overnight, the resin filtered off, the solvent evaporated in vacuo and the residue passed through an SCX column eluting first with methanol and then 2M ammonia in methanol. The basic fractions were combined and solvent evaporated in vacuo to afford a crude product which was purified further by chromatography on silica gel using a Flashmaster and an elution gradient of 0 to 10% methanol in dichloromethane. The relevant fractions were combined and the solvent evaporated in vacuo to afford the title compound (E102). MS (ES+) m/e 468/470 [M+H]+.

Example 103

4-Bromo-N-[5-(cis-3,5-dimethyl-1-piperazinyl)-2-(methyloxy)phenyl]-2-fluorobenzenesulfonamide (E103)

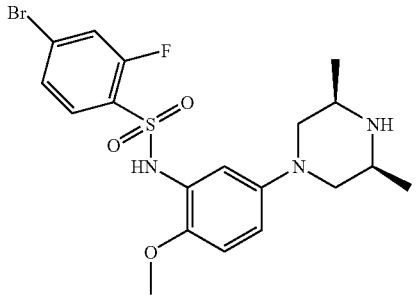

A solution of 5-(cis-3,5-dimethyl-1-piperazinyl)-2-(methyloxy)aniline (D4) (1.20 g, 5.09 mmol) in dichloromethane (35 ml) was treated with morpholinomethyl-polystyrene HL resin (2.43 g, 4.2 mmol/g loading, 10.2 mmol) followed by 4-bromo-2-fluorobenzenesulfonyl chloride (2.79 g, 10.2 mmol). The resulting solution was stirred at room temperature overnight, the resin was then filtered off, the solvent evaporated in vacuo and the residue was then passed through an SCX column eluting first with methanol and then by 2M ammonia in methanol. The basic fractions were combined and solvent evaporated in vacuo to afford a crude product which was dry loaded onto a column and purified further by chromatography using a Flashmaster and an elution gradient of 0 to 10% methanol in dichloromethane The relevant fractions were collected, combined and solvent evaporated to afford the title compound (E103). MS (ES+) m/e 472/474 [M+H]+.

Example 104

4-Bromo-2-chloro-N-[5-(cis-3,5-dimethyl-1-piperazinyl)-2-(methyloxy)phenyl]benzenesulfonamide (E104)

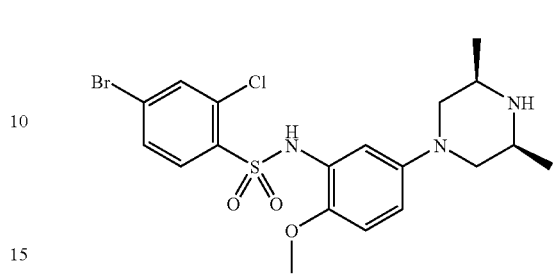

A solution of 5-(cis-3,5-dimethyl-1-piperazinyl)-2-(methyloxy)aniline (D4) (1.20 g, 5.09 mmol) in dichloromethane (35 ml) was treated with morpholinomethyl-polystyrene HL resin (2.43 g, 4.2 mmol/g loading, 10.21 mmol) and then the 4-bromo-2-chlorobenzenesulfonyl chloride (2.96 g, 10.21 mmol). The resulting solution was stirred at room temperature overnight. The resin and was filtered, washed with methanol, and the solvent evaporated in vacuo. The residue was then passed through an SCX column eluting first with methanol followed by 2M ammonia in methanol. The basic fractions were collectedand solvent evaporated in vacuo to afford a crude product which was purified further by chromatography using a Flashmaster using an elution gradient of 0 to 5% methanol in dichloromethane. The relevant fractions were collected, combined and the solvent evaporated in vacuo to afford the title compound (E104). MS (ES+) m/e 488/490/492 [M+H]+.

Example 105

4-Bromo-N-[5-(cis-3,5-dimethyl-1-piperazinyl)-2-(methyloxy)phenyl]-3-fluorobenzenesulfonamide (E105)

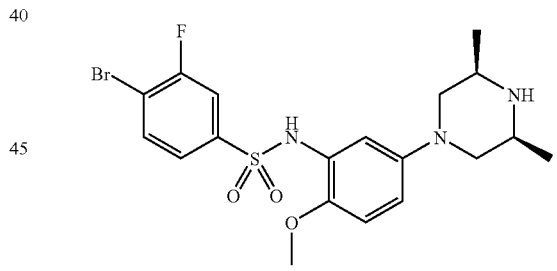

A solution of 5-(cis-3,5-dimethyl-1-piperazinyl)-2-(methyloxy)aniline (D4) (400 mg,1.70 mmol) in dichloromethane (15 ml) was treated with morpholinomethyl-polystyrene HL resin (1.00 g, 3.4 mmol/g loading) followed by 4-bromo-3-fluorobenzenesulfonyl chloride (0.50 ml, 930 mg, 3.40 mmol). The resulting solution was stirred at room temperature for overnight (20 hours). The reaction mixture and was then filtered, washed with methanol, and the solvent evaporated in vacuo. The residue was applied to an SCX column eluting first with methanol and then 2M ammonia in methanol. The fractions containing product were collected, combined and evaporated in vacuo to afford a crude product which was dry loaded onto a column and purified further by chromatography using a Flashmaster with an eluting gradient of 0 to 5% methanol in dichloromethane over 40 mins. Fractions containing product were combined and evaporated in vacuo to afford the title compound (E105). MS (ES+) m/e 472/474 [M+H]+.

Example 106

4-Bromo-N-[5-(cis-3,5-dimethyl-1-piperazinyl)-2-(methyloxy)phenyl]benzenesulfonamide (E106)

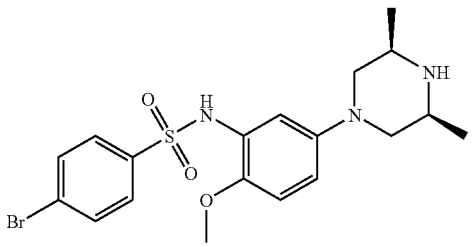

A solution of 5-(cis-3,5-dimethyl-1-piperazinyl)-2-(methyloxy)aniline (D4) (1.20 g, 5.1 mmol) in dichloromethane (35 ml) was treated with morpholinomethyl-polystyrene HL resin (2.45 g, 4.2 mmol/g loading, 10.29 mmol) followed by 4-bromobenzenesulfonyl chloride (2.60 g, 10.2 mmol). The resulting solution was stirred at room temperature overnight (~24hours)and then the resin filtered off with methanol and the solvent evaporated in vacuo. The residue was passed through an SCX column eluting first with methanol followed by 2M ammonia in methanol. The relevant fractions were collected, combined and the solvent evaporated in vacuo. The crude product was purified by Flashmaster causing an elution gradient of 0 to 10% methanol in dichloromethane. The relevant fractions were collected, combined and the solvent evaporated to afford the title compound (E106). MS (ES+) m/e 454/456 [M+H]+.

Example 107

N-[5-(cis-3,5-Dimethyl-1-piperazinyl)-2-(methyloxy)phenyl]-4-(4-methyl-2-thienyl)benzenesulfonamide (E107)

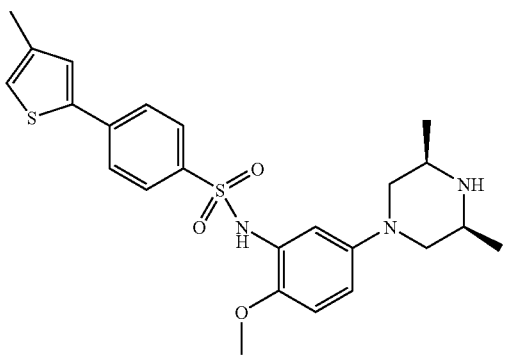

To a mixture of 4-bromo-N-[5-(cis-3,5-dimethyl-1-piperazinyl)-2-(methyloxy)phenyl]benzenesulfonamide (E106) (100 mg, 0.22 mmol) and (4-methyl-2-thienyl)boronic acid (71 mg, 0.50 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol). The appropriate fractions were combined and solvent evaporated in vacuo and the residue purified further by mass directed autoprep HPLC to afford the title compound (E107). MS (ES+) m/e 472 [M+H]+.

Example 108

N-[5-(cis-3,5-Dimethyl-1-piperazinyl)-2-(methyloxy)phenyl]-2-methyl-4-(4-methyl-2-thienyl)benzenesulfonamide (E108)

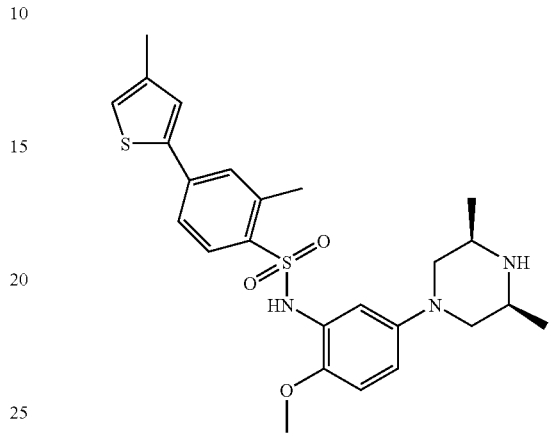

To a mixture of 4-bromo-N-[5-(cis-3,5-dimethyl-1-piperazinyl)-2-(methyloxy)phenyl]-2-methylbenzenesulfonamide (E102) (120 mg, 0.26 mmol) and (4-methyl-2-thienyl)boronic acid (73 mg, 0.51 mmol) in DME (3 ml) was added potassium tert-butoxide (263 mg, 2.34 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol). The appropriate fractions were combined and evaporated in vacuo and the residue purified further by mass directed autoprep HPLC to afford the title compound (E108). MS (ES+) m/e 486 [M+H]+.

Example 109

N-[5-(cis-3,5-Dimethyl-1-piperazinyl)-2-(methyloxy)phenyl]-4-(2-furanyl)benzenesulfonamide (E109)

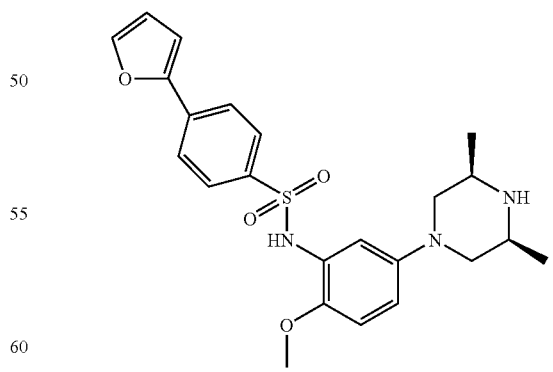

To a mixture of 4-bromo-N-[5-(cis-3,5-dimethyl-1-piperazinyl)-2-(methyloxy)phenyl]benzenesulfonamide (E106) (100 mg, 0.22 mmol) and 2-furanylboronic acid (50 mg, 0.45 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol). The appropriate fractions were combined and evaporated in vacuo and the residue purified further by mass directed autoprep HPLC to afford the title compound (E109). MS (ES+) m/e 442 [M+H]+.

Example 110

N-[5-(cis-3,5-Dimethyl-1-piperazinyl)-2-(methyloxy)phenyl]-2-fluoro-4-(4-methyl-2-thienyl)benzenesulfonamide (E110)

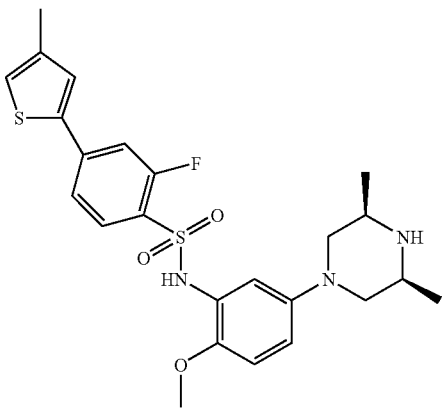

To a mixture of 4-bromo-N-[5-(cis-3,5-dimethyl-1-piperazinyl)-2-(methyloxy)phenyl]-2-fluorobenzenesulfonamide (E103) (100 mg, 0.21 mmol) and (4-methyl-2-thienyl)boronic acid (60 mg, 0.42 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol) The appropriate fractions were combined and evaporated in vacuo and the residue purified further by mass directed autoprep HPLC to afford the title compound (E110). MS (ES+) m/e 490 [M+H]+.

Example 111

3'-Chloro-N-[5-(cis-3,5-dimethyl-1-piperazinyl)-2-(methyloxy)phenyl]-4-biphenylsulfonamide (E111)

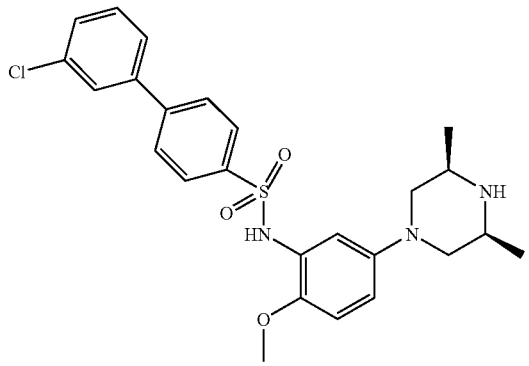

To a mixture of 4-bromo-N-[5-(cis-3,5-dimethyl-1-piperazinyl)-2-(methyloxy)phenyl]benzenesulfonamide (E106) (75 mg, 0.17 mmol) and (3-chlorophenyl)boronic acid (56 mg, 0.36 mmol) in DME (3 ml) was added potassium tert-butoxide (180 mg, 1.60 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol). The appropriate fractions were combined and evaporated in vacuo and the residue purified further by mass directed autoprep HPLC to afford the title compound (E111). MS (ES+) m/e 486/488 [M+H]+.

Example 112

N-[5-(cis-3,5-Dimethyl-1-piperazinyl)-2-(methyloxy)phenyl]-2-fluoro-4-(2-furanyl)benzenesulfonamide (E112)

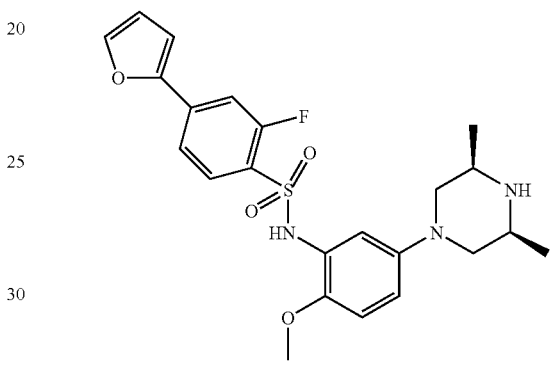

To a mixture of 4-bromo-N-[5-(cis-3,5-dimethyl-1-piperazinyl)-2-(methyloxy)phenyl]-2-fluorobenzenesulfonamide (E103) (100 mg, 0.21 mmol) and 2-furanylboronic acid (50 mg, 0.42 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated in vacuo and purified using an SCX cartridge eluting with methanol followed by ammonia (2M in methanol). The appropriate fractions were combined and evaporated in vacuo and the residue purified further by mass directed autoprep HPLC to afford the title compound (E112). MS (ES+) m/e 460 [M+H]+.

Example 113

2-Chloro-N-[5-(cis-3,5-dimethyl-1-piperazinyl)-2-(methyloxy)phenyl]-4-(4-methyl-2-thienyl)benzenesulfonamide (E113)

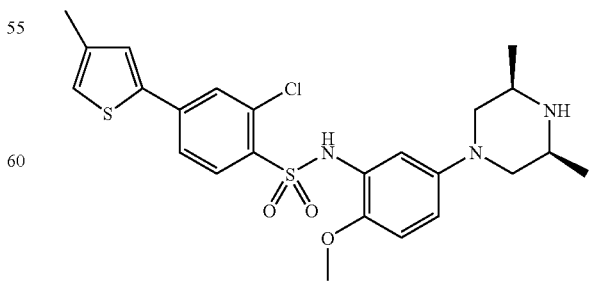

To a mixture of 4-bromo-2-chloro-N-[5-(cis-3,5-dimethyl-1-piperazinyl)-2-(methyloxy)phenyl]benzenesulfonamide (E104) (70 mg, 0.14 mmol) and (4-methyl-2-thienyl) boronic acid (40 mg, 0.28 mmol) in DME (3 ml) was added potassium tert-butoxide (142 mg, 1.26 mmol) and tetrakis(triphenylphosphine)palladium(0) (12 mg, 0.01 mmol) in water (1 ml) and the resulting mixture stirred in a microwave (set at high absorbance) at 100° C. for 30 minutes. Additional (4-methyl-2-thienyl)boronic acid (20 mg, 0.14 mmol) and tetrakis(triphenylphosphine)palladium(0) (12 mg, 0.01 mmol) were then added and the mixture stirred in a microwave (set at high absorbance) at 100° C. for a further 30 minutes. The solvent was evaporated after transfer to a new flask with methanol and a few drops of toluene and the residue passed through an SCX column eluting with methanol followed by 2M ammonia in methanol. The appropriate fractions were collected and evaporated in vacuo and the residue purified further by mass directed autoprep HPLC to afford the title compound (E113). MS (ES+) m/e 506/508 [M+H]+.

The hydrochloride salt of the product was prepared by dissolving the pure material from chromatography in 1 ml dichloromethane and treating with 0.5 ml HCl (1M) in ether.

Example 114

N-[5-(cis-3,5-Dimethyl-1-piperazinyl)-2-(methyloxy)phenyl]-3-fluoro-4-(2-thienyl)benzenesulfonamide (E114)

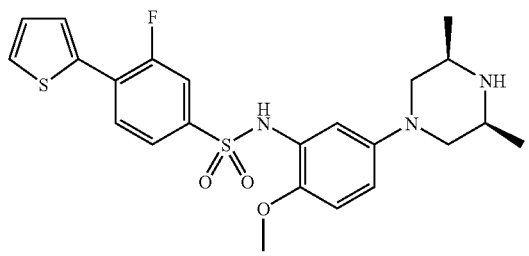

To a mixture of 4-bromo-N-[5-(cis-3,5-dimethyl-1-piperazinyl)-2-(methyloxy)phenyl]-3-fluorobenzenesulfonamide (E105) (100 mg, 0.21 mmol) and 2-thienylboronic acid (54 mg, 0.42 mmol) in DME (3 ml) was added potassium tert-butoxide (212 mg, 1.89 mmol) and tetrakis(triphenylphosphine)palladium(0) (12 mg, 0.01 mmol) in water (1 ml) and the resulting mixture stirred in a microwave (set at high absorbance) at 100° C. for 30 minutes. Additional 2-thienylboronic acid (27 mg, 0.21 mmol) and tetrakis(triphenylphosphine)palladium(0) (12 mg, 0.01 mmol) were then added and the mixture stirred in a microwave (set at high absorbance) at 100° C. for a further 45 minutes. The solvent was evaporated with addition of a few drops of toluene and the residue passed through an SCX column eluting with methanol followed by 2M ammonia in methanol. The abasic fractions were combined and the solvent evaporated. The crude product was purified by mass directed autoprep HPLC, the relevant fractions collected and solvent evaporated to afford the title compound (E114). MS (ES+) m/e 476 [M+H]+.

The hydrochloride salt of the product was prepared by dissolving the pure material from chromatography in 1 ml dichloromethane and a few drops of methanol and acidifying with 0.5 ml HCl (1M) in ether.

Example 115

N-[5-(cis-3,5-Dimethyl-1-piperazinyl)-2-(methyloxy)phenyl]-3-fluoro-4-(4-methyl-2-thienyl)benzenesulfonamide (E115) GSK719250A (KC104997-020B3)

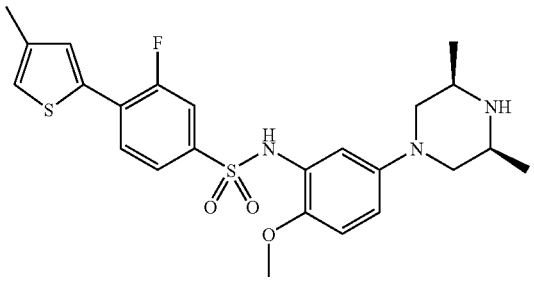

To a mixture of 4-bromo-N-[5-(cis-3,5-dimethyl-1-piperazinyl)-2-(methyloxy)phenyl]-3-fluorobenzenesulfonamide (E105) (100 mg, 0.21 mmol) and (4-methyl-2-thienyl)boronic acid (60 mg, 0.42 mmol) in DME (3 ml) was added potassium tert-butoxide (212 mg, 1.89 mmol) and tetrakis(triphenylphosphine)palladium(0) (12 mg, 0.01 mmol) in water (1 ml) and the resulting mixture stirred in a microwave (set at high absorbance) at 100° C. for 30 minutes. Additional (4-methyl-2-thienyl)boronic acid (30 mg, 0.21 mmol) and tetrakis(triphenylphosphine)palladium(0) (12 mg, 0.01 mmol) were then added and the mixture stirred in a microwave (set at high absorbance) at 100° C. for a further 45 minutes. The solvent was evaporated with the addition of a few drops of toluene and the residue passed through an SCX column eluting with methanol followed by 2M ammonia in methanol. The basic fractions were combined and the solvent evaporated. The crude product was purified by mass directed autoprep HPLC and relevant fractions collected and solvent evaporated to afford the title compound (E115). MS (ES+) m/e 490 [M+H]+.

The hydrochloride salt of the product was prepared by dissolving the pure material from chromatography in 1 ml dichloromethane and a few drops of methanol and acidifying with 0.5 ml HCl (1M) in ether.

Example 116

N-[5-(cis-3,5-Dimethyl-1-piperazinyl)-2-(methyloxy)phenyl]-3-fluoro-4-(3-furanyl)benzenesulfonamide (E116)

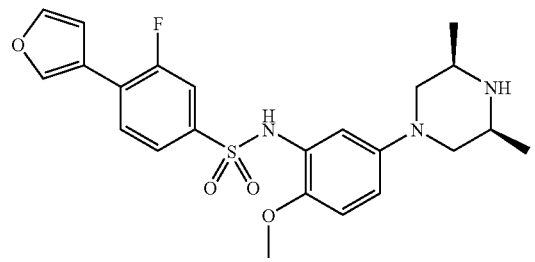

To a mixture of 4-bromo-N-[5-(cis-3,5-dimethyl-1-piperazinyl)-2-(methyloxy)phenyl]-3-fluorobenzenesulfonamide (E105) (100 mg, 0.21 mmol) and 3-furanylboronic acid (47 mg, 0.42 mmol) in DME (3 ml) was added potassium tert-butoxide (212 mg, 1.89 mmol) and tetrakis(triphenylphosphine)palladium(0) (12 mg, 0.01 mmol) in water (1 ml) and the resulting mixture stirred in a microwave (set at high absorbance) at 100° C. for 30 minutes. The solvent was evaporated with the addition of a few drops of toluene and the residue passed through an SCX column eluting with methanol followed by 2M ammonia in methanol. The basic fractions were combined and the solvent evaporated. The crude product was purified by mass directed autoprep HPLC and the relevant fractions collected and solvent evaporated to afford the title compound (E116). MS (ES+) m/e 460 [M+H]$^+$.

The hydrochloride salt of the product was prepared by dissolving the pure material from chromatography in 1 ml dichloromethane and a few drops methanol and acidifying with 0.5 ml HCl (1M) in ether.

Example 117

N-[5-(cis-3,5-Dimethyl-1-piperazinyl)-2-(methyloxy)phenyl]-3'-[(methyloxy)methyl]-4-biphenylsulfonamide (E117)

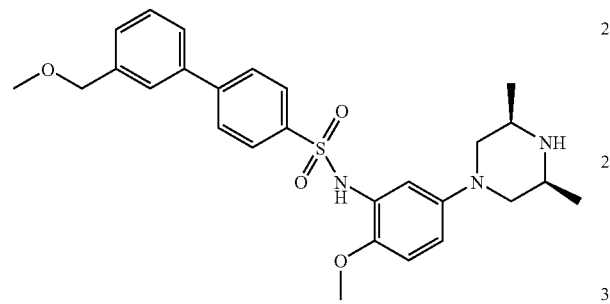

To a mixture of 4-bromo-N-[5-(cis-3,5-dimethyl-1-piperazinyl)-2-(methyloxy)phenyl]benzenesulfonamide (E106) (100 mg, 0.22 mmol) and {3-[(methyloxy)methyl]phenyl}boronic acid (75 mg, 0.45 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was then evaporated and purified by SCX followed by mass directed autoprep HPLC to afford the title compound (E117). MS (ES+) m/e 496 [M+H]$^+$.

The hydrochloride salt of the product was prepared by dissolving the pure material from chromatography in 1 ml dichloromethane, acidifying with 0.4 ml HCl (1M) and stirring at room temperature for 30 mins, evaporating and drying.

Example 118

N-[5-(cis-3,5-Dimethyl-1-piperazinyl)-2-(methyloxy)phenyl]-4-(3-furanyl)benzenesulfonamide (E118)

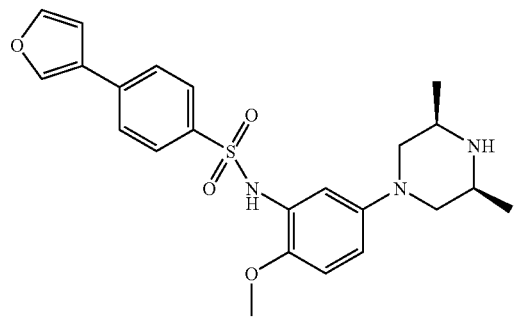

To a mixture of 4-bromo-N-[5-(cis-3,5-dimethyl-1-piperazinyl)-2-(methyloxy)phenyl]benzenesulfonamide (E106) (100 mg, 0.22 mmol) and 3-furanylboronic acid (54 mg, 0.48 mmol) in DME (3 ml) was added potassium tert-butoxide (220 mg, 1.96 mmol) and tetrakis(triphenylphosphine)palladium(0) (15 mg, 0.01 mmol) in water (1 ml) and the resulting mixture stirred in a microwave (set at high absorbance) at 100° C. for 30 minutes. The resulting mixture was purified by SCX followed by mass directed autoprep HPLC to afford the title compound (E118). MS (ES+) m/e 442 [M+H]$^+$.

The hydrochloride salt of the product was prepared by dissolving the solid material from chromatography in 1 ml dichloromethane and adding 0.4 ml HCl (1M) in ether, stirring at room temperature for 30 mins, evaporating and drying.

Example 119

N-[5-(cis-3,5-Dimethyl-1-piperazinyl)-2-(methyloxy)phenyl]-4-(3-thienyl)benzenesulfonamide (E119)

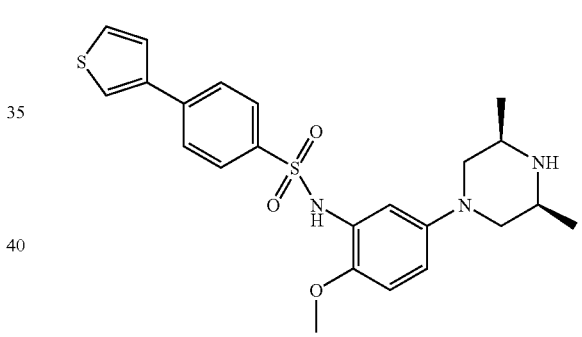

To a mixture of 4-bromo-N-[5-(cis-3,5-dimethyl-1-piperazinyl)-2-(methyloxy)phenyl]benzenesulfonamide (E106) (200 mg, 0.44 mmol) and 3-thienylboronic acid (113 mg, 0.88 mmol) in DME (3 ml) was added potassium tert-butoxide (445 mg, 3.97 mmol) and tetrakis(triphenylphosphine)palladium(0) (30.5 mg, 0.03 mmol) in water (1 ml) and the resulting mixture stirred in a microwave (set at high absorbance) at 100° C. for 30 minutes. 2-3 ml of toluene added and solvent evaporated, the residue dissolved in methanol and added to a preconditioned (methanol) SCX cartridge eluting with methanol (×3), ammonia (1M in methanol (×2)) and then ammonia (2M in methanol (×3)), followed by by mass directed autoprep HPLC followed by trituration with diethyl ether to afford the title compound (E119). MS (AP+) m/e 458 [M+H]$^+$.

The hydrochloride salt of the product was prepared by dissolving the pure material from chromatography in 1 ml dichloromethane and acidifying with 0.5 ml HCl (1M) in ether, stirring at room temperature for 1 hour.

Example 120

N-[5-(cis-3,5-Dimethyl-1-piperazinyl)-2-hydroxyphenyl]-5-(2-pyridinyl)-2-thiophenesulfonamide (E120)

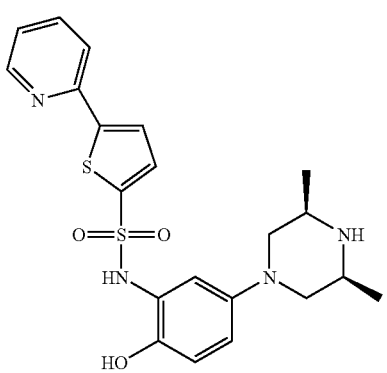

N-[5-(cis-3,5-Dimethyl-1-piperazinyl)-2-(methyloxy)phenyl]-5-(2-pyridinyl)-2-thiophenesulfonamide (E13) (277 mg, 0.66 mmol) was dissolved in dichloromethane (5 ml) and treated with 1M boron tribromide in dichloromethane (1.8 ml, 1.8 mol) for 4.5 hours. Further 1M boron tribromide in dichloromethane (3 ml, 3 mmol) was added and the mixture stirred at room temperature overnight. Water and methanol were cautiously added and the solution basified to pH9 with saturated aqueous sodium bicarbonate solution. The precipitated solids were filtered, washed with ether and purified by mass directed autoprep HPLC to afford the title compound (E120). MS (ES+) m/e 445 [M+H]+.

Example 121

N-[5-(cis3,5-Dimethyl-1-piperazinyl)-2-(methyloxy)phenyl]-4-(2-oxo-1-pyrrolidinyl)benzenesulfonamide (E121)

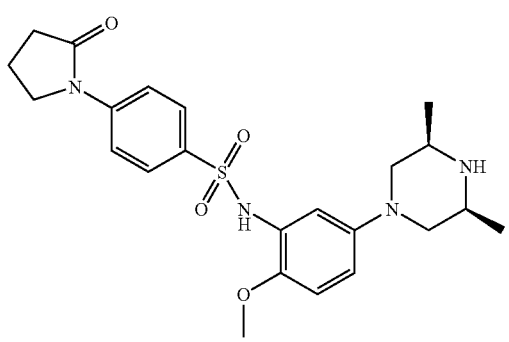

The title compound (E121) was prepared from 4-bromo-N-[5-(cis-3,5-dimethyl-1-piperazinyl)-2-(methyloxy)phenyl]benzenesulfonamide (E106) and 2-pyrrolidinone using a similar method to that described for Example 23 (E23). MS (ES+) m/e 459 [M+H]+.

Example 122

5-Bromo-N-[5-(cis-3,5-dimethyl-1-piperazinyl)-2-(methyloxy)phenyl]-2-thiophenesulfonamide (E122)

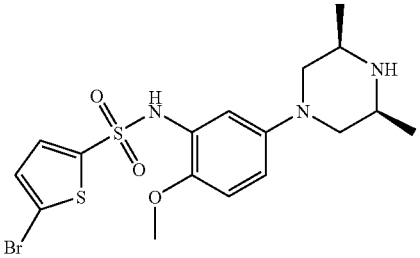

A solution of 5-(cis-3,5-dimethyl-1-piperazinyl)-2-(methyloxy)aniline (D4) (1.00 g, 4.25 mmol) in dichloromethane (50 ml) was treated with morpholinomethyl-polystyrene HL resin (2.10 g, 4.0 mmol/g loading, 8.50 mmol) followed by 5-bromo-2-thiophenesulfonyl chloride (1.33 g, 5.09 mmol). The resulting solution was stirred at room temperature overnight and was then filtered and the solvent evaporated. The residue was then chromatographed over silica gel (Flashmaster (II)) eluting with 0 to 10% methanol in dichloromethane 90% for 5 mins, 0-10% 20 mins and 10% 10 mins). The compound was then purified by mass directed autoprep HPLC and the residue further purified by SCX, eluting with methanol first and then NH4OH/methanol. (E122). MS (ES+) m/e 460/462 [M+H]+.

Example 123

N-[5-(cis-3,5-Dimethyl-1-piperazinyl)-2-(methyloxy)phenyl]-5-{3-[(methyloxy)methyl]phenyl}-2-thiophenesulfonamide (E123)

To a mixture of 5-bromo-N-[5-(cis-3,5-dimethyl-1-piperazinyl)-2-(methyloxy)phenyl]-2-thiophenesulfonamide (E122) (100 mg, 0.22 mmol) and {3-[(methyloxy)methyl]phenyl}boronic acid (83 mg, 0.5 mmol) in DME (3 ml) was added potassium tert-butoxide (210 mg, 1.9 mmol) and tetrakis(triphenylphosphine)palladium(0) (15 mg, 0.013 mmol) in water (1 ml) and the resulting mixture stirred in a microwave (set at high absorbance) at 100° C. for 30 minutes. The resulting mixture was then concentrated in Genevac and residues passed over SCX. Basic fractions were re-concentrated in Genevac and the residue purified using mass directed autoprep HPLC to afford the title compound (E123). MS (ES+) m/e 502 [M+H]+.

Example 124

N-[5-(cis-3,5-Dimethyl-1-piperazinyl)-2-(methyloxy)phenyl]-5-(2-fluorophenyl)-2-thiophenesulfonamide (E124)

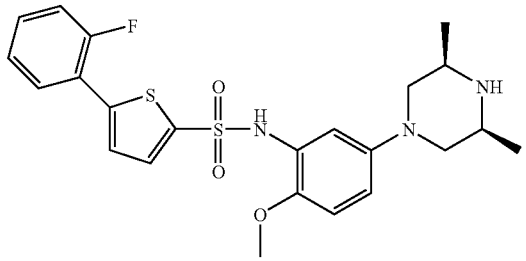

To a mixture of 5-bromo-N-[5-(cis-3,5-dimethyl-1-piperazinyl)-2-(methyloxy)phenyl]-2-thiophenesulfonamide (E122) (150 mg, 0.33 mmol) and (2-fluorophenyl)boronic acid (91 mg, 0.65 mmol) in DME (3 ml) was added potassium tert-butoxide (329 mg, 2.94 mmol) and tetrakis(triphenylphosphine)palladium(0) (37 mg, 0.033 mmol) in water (1 ml) and the resulting mixture stirred in a microwave (set at high absorbance) at 100° C. for 30 minutes. The resulting mixture was then reduced in vacuo, azeotroped with toluene (×3) and purified using SCX then mass directed autoprep HPLC to afford the title product (E124). MS (ES+) m/e 476 [M+H]$^+$.

The hydrochloride salt of the product was prepared by dissolving the pure material from chromatography in 1 ml dichloromethane and acidifying with 1 ml HCl (1M) in ether, stirring for 30 mins at room temperature and reduced under vacuum.

Example 125

5-Chloro-N-[5-(cis-3,5-dimethyl-1-piperazinyl)-2-(methyloxy)phenyl]-2-naphthalenesulfonamide (E125)

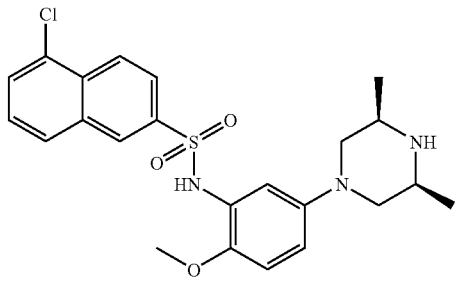

To a solution of 5-(cis-3,5-Dimethyl-1-piperazinyl)-2-(methyloxy)aniline (D4) (100 mg, 0.42 mmol) in pyridine (3 ml) was added 5-chloro-2-naphthalenesulfonyl chloride (167 mg, 0.64 mmol) and the resulting mixture stirred at room temperature for 1 hour. The pyridine was then evaporated and the crude residue dissolved in dichloromethane (25 ml) and extracted with saturated aqueous sodium bicarbonate solution (25 ml). The aqueous layer was re-extracted with dichloromethane (2×25 ml) and the combined organic layers washed with brine, dried over anhydrous magnesium sulfate, and solvent evaporated. The crude residue was then dissolved in methanol and added to a pre-conditioned log SCX cartridge (methanol) eluting with methanol (×2) followed by ammonia (1M in methanol (×3) to 2M in methanol (×2)). The appropriate fractions were combined and reduced in vacuo and the residue purified further by mass directed autoprep HPLC to afford the title (E125). MS (AP+) m/e 460/462 [M+H]$^+$.

The hydrochloride salt of the product was prepared by dissolving the pure material from chromatography in 1 ml dichloromethane, 1 ml methanol, acidifying with 0.5 ml HCl (1M) in ether and stirring at room temperature for 45 mins.

Examples 126-196

Examples 126-196 (E126-E196) were prepared using methods similar to that described below from the appropriate aryl halide and boronic acid as listed in the table:

To a mixture of the appropriate aryl halide (1 eq) and boronic acid (2 eq) (or boronate ester) in DME (ca. 0.1M) was added a solution of potassium tert-butoxide (9 eq) and tetrakis(triphenylphosphine)palladium(0) (5-10 mol %) in water (ca. 0.2M) and the resulting mixture stirred in a microwave (set at high absorbance) at 100° C. for 30 minutes. If appropriate, additional boronic acid and tetrakis(triphenylphosphine)palladium(0) were added and the mixture stirred in a microwave (set at high absorbance) at 100° C. for a further 30-45 minutes. The resulting mixture was then reduced in vacuo and purified using an SCX ion exchange cartridge (Varian bond-elute) eluting with methanol followed by ammonia (2M in methanol). Alternatively, the crude reaction mixture was added directly to the SCX ion exchange cartridge (Varian bond-elute) eluting with methanol followed by ammonia (2M in methanol). The appropriate fractions were combined and reduced in vacuo and the residue purified by mass directed autoprep HPLC or chromatography on silica gel to afford the title compound which was characterized as either the free base or hydrochloride salt.

| Example | Aryl Halide | Boronic acid or boronate ester | MS [M + H]$^+$ |
|---|---|---|---|
| N-[5-(cis-3,5-Dimethyl-1-piperazinyl)-2-(methyloxy)phenyl]-4-(6-methyl-2-pyridinyl)benzenesulfonamide (E126) | E106 | Bis(1,1-Dimethylethyl) (6-methyl-2-pyridinyl)boronate (WO 02/094815) | 467 |
| N-[5-(cis-3,5-Dimethyl-1-piperazinyl)-2-(methyloxy)phenyl]-5-(6-methyl-2-pyridinyl)-2-thiophenesulfonamide (E127) | E122 | Bis(1,1-Dimethylethyl) (6-methyl-2-pyridinyl)boronate (WO 02/094815) | 473 |

-continued

| Example | Aryl Halide | Boronic acid or boronate ester | MS [M + H]+ |
|---|---|---|---|
| N-[3-(cis-3,5-Dimethyl-1-piperazinyl)-4-(methyloxy)phenyl]-4-(6-methyl-2-pyridinyl)benzenesulfonamide (E128) | E101 | Bis(1,1-Dimethylethyl) (6-methyl-2-pyridinyl)boronate (WO 02/094815) | 467 |
| N-[5-(cis-3,5-Dimethyl-1-piperazinyl)-2-(methyloxy)phenyl]-4-(3-pyridinyl)benzenesulfonamide (E129) | E106 | 3-Pyridinylboronic acid | 453 |
| N-[5-(cis-3,5-Dimethyl-1-piperazinyl)-2-(methyloxy)phenyl]-2,2'-bithiophene-5-sulfonamide (E130) | E122 | 2-Thienylboronic acid | 464 |
| N-[5-(cis-3,5-Dimethyl-1-piperazinyl)-2-(methyloxy)phenyl]-3-(2-thienyl)benzenesulfonamide (E131) | E76 | 2-Thienylboronic acid | 458 |
| N-[3-(cis-3,5-Dimethyl-1-piperazinyl)-4-(methyloxy)phenyl]-4-(3-thienyl)benzenesulfonamide (E132) | E101 | 3-Thienylboronic acid | 458 |
| 4-(1-Benzothien-3-yl)-N-[5-(cis-3,5-dimethyl-1-piperazinyl)-2-(methyloxy)phenyl]benzenesulfonamide (E133) | E106 | 1-Benzothien-3-ylboronic acid | 508 |
| N-[3-(cis-3,5-Dimethyl-1-piperazinyl)-4-(methyloxy)phenyl]-2,3'-bithiophene-5-sulfonamide (E134) | E74 | 3-Thienylboronic acid | 464 |
| N-[3-(cis-3,5-Dimethyl-1-piperazinyl)-4-(methyloxy)phenyl]-5-phenyl-2-thiophenesulfonamide (E135) | E74 | Phenylboronic acid | 458 |
| 5-(1-Benzothien-3-yl)-N-[5-(cis-3,5-dimethyl-1-piperazinyl)-2-(methyloxy)phenyl]-2-thiophenesulfonamide (E136) | E122 | 1-Benzothien-3-ylboronic acid | 514 |
| N-[5-(cis-3,5-Dimethyl-1-piperazinyl)-2-(methyloxy)phenyl]-5-[4-(methyloxy)-3-pyridinyl]-2-thiophenesulfonamide (E137) | E122 | [4-(methyloxy)-3-pyridinyl]boronic acid hydrochloride | 489 |
| N-[3-(cis-3,5-Dimethyl-1-piperazinyl)-4-(methyloxy)phenyl]-2,2'-bithiophene-5-sulfonamide (E138) | E74 | 2-Thienylboronic acid | 464 |
| N-[5-(cis-3,5-Dimethyl-1-piperazinyl)-2-(methyloxy)phenyl]-2'-(ethyloxy)-4-biphenylsulfonamide (E139) | E106 | [2-(Ethyloxy)phenyl]boronic acid | 496 |
| N-[3-(cis-3,5-Dimethyl-1-piperazinyl)-4-(methyloxy)phenyl]-4'-fluoro-2'-methyl-4-biphenylsulfonamide (E140) | E101 | (4-Fluoro-2-methylphenyl)boronic acid | 484 |
| N-[3-(cis-3,5-Dimethyl-1-piperazinyl)-4-(methyloxy)phenyl]-2'-fluoro-4-biphenylsulfonamide (E141) | E101 | (2-Fluorophenyl)boronic acid | 470 |
| N-[5-(cis-3,5-Dimethyl-1-piperazinyl)-2-(methyloxy)phenyl]-2,3'-bithiophene-5-sulfonamide (E142) | E122 | 3-Thienylboronic acid | 464 |
| N-[3-(cis-3,5-Dimethyl-1-piperazinyl)-4-(methyloxy)phenyl]-2-methyl-4-(2-thienyl)benzenesulfonamide (E143) | E72 | 2-Thienylboronic acid | 472 |
| N-[3-(cis-3,5-Dimethyl-1-piperazinyl)-4-(methyloxy)phenyl]-2-methyl-4-(6-methyl-2-pyridinyl)benzenesulfonamide (E144) | E72 | Bis(1,1-Dimethylethyl) (6-methyl-2-pyridinyl)boronate (WO 02/094815) | 481 |
| 3'-Chloro-N-[3-(cis-3,5-dimethyl-1-piperazinyl)-4-(methyloxy)phenyl]-4'-fluoro-4-biphenylsulfonamide (E145) | E101 | (3-Chloro-4-fluorophenyl)boronic acid | 504/506 |
| N-[3-(cis-3,5-Dimethyl-1-piperazinyl)-4-(methyloxy)phenyl]-3',5'-difluoro-4-biphenylsulfonamide (E146) | E101 | (3,5-Difluorophenyl)boronic acid | 488 |
| N-[3-(cis-3,5-Dimethyl-1-piperazinyl)-4-(methyloxy)phenyl]-3'-fluoro-4-biphenylsulfonamide (E147) | E101 | (3-Fluorophenyl)boronic acid | 470 |
| N-[3-(cis-3,5-Dimethyl-1-piperazinyl)-4-(methyloxy)phenyl]-3',4'-difluoro-4-biphenylsulfonamide (E148) | E101 | (3,4-Difluorophenyl)boronic acid | 488 |
| N-[3-(cis-3,5-Dimethyl-1-piperazinyl)-4-(methyloxy)phenyl]-2',6'-dimethyl-4-biphenylsulfonamide (E149) | E101 | (2,6-Dimethylphenyl)boronic acid | 480 |
| N-[3-(cis-3,5-Dimethyl-1-piperazinyl)-4-(methyloxy)phenyl]-4'-fluoro-4-biphenylsulfonamide (E150) | E101 | (4-Fluorophenyl)boronic acid | 470 |

-continued

| Example | Aryl Halide | Boronic acid or boronate ester | MS [M + H]+ |
|---|---|---|---|
| N-[3-(cis-3,5-Dimethyl-1-piperazinyl)-4-(methyloxy)phenyl]-4'-methyl-4-biphenylsulfonamide (E151) | E101 | (4-Methylphenyl)boronic acid | 466 |
| N-[3-(cis-3,5-Dimethyl-1-piperazinyl)-4-(methyloxy)phenyl]-2',3'-difluoro-4-biphenylsulfonamide (E152) | E101 | (2,3-Difluorophenyl)boronic acid | 488 |
| N-[3-(cis-3,5-Dimethyl-1-piperazinyl)-4-(methyloxy)phenyl]-3'-methyl-4-biphenylsulfonamide (E153) | E101 | (3-Methylphenyl)boronic acid | 466 |
| 2'-Chloro-N-[5-(cis-3,5-dimethyl-1-piperazinyl)-2-(methyloxy)phenyl]-4-biphenylsulfonamide (E154) | E106 | (2-Chlorophenyl)boronic acid | 486/488 |
| N-[5-(cis-3,5-Dimethyl-1-piperazinyl)-2-(methyloxy)phenyl]-2-methyl-4-(2-thienyl)benzenesulfonamide (E155) | E102 | 2-Thienylboronic acid | 472 |
| N-[3-(cis-3,5-Dimethyl-1-piperazinyl)-4-(methyloxy)phenyl]-3'-[(methyloxy)methyl]-4-biphenylsulfonamide (E156) | E101 | {3-[(Methyloxy)methyl]phenyl}boronic acid | 496 |
| N-[5-(cis-3,5-Dimethyl-1-piperazinyl)-2-(methyloxy)phenyl]-2-fluoro-4-(2-thienyl)benzenesulfonamide (E157) | E103 | 2-Thienylboronic acid | 476 |
| N-[3-(cis-3,5-Dimethyl-1-piperazinyl)-4-(methyloxy)phenyl]-2-methyl-4-(4-methyl-2-thienyl)benzenesulfonamide (E158) | E72 | (4-Methyl-2-thienyl)boronic acid | 486 |
| N-[5-(cis-3,5-Dimethyl-1-piperazinyl)-2-(methyloxy)phenyl]-4-(5-methyl-2-thienyl)benzenesulfonamide (E159) | E106 | (5-Methyl-2-thienyl)boronic acid | 472 |
| N-[3-(cis-3,5-Dimethyl-1-piperazinyl)-4-(methyloxy)phenyl]-3-fluoro-4-(2-thienyl)benzenesulfonamide (E160) | E50 | 2-Thienylboronic acid | 476 |
| 2-Chloro-N-[3-(cis-3,5-dimethyl-1-piperazinyl)-4-(methyloxy)phenyl]-4-(4-methyl-2-thienyl)benzenesulfonamide (E161) | E51 | (4-Methyl-2-thienyl)boronic acid | 506/508 |
| N-[5-(cis-3,5-Dimethyl-1-piperazinyl)-2-(methyloxy)phenyl]-4-(4-methyl-3-thienyl)benzenesulfonamide (E162) | E106 | (4-Methyl-3-thienyl)boronic acid | 472 |
| N-[5-(cis-3,5-Dimethyl-1-piperazinyl)-2-(methyloxy)phenyl]-4-(3-furanyl)-2-methylbenzenesulfonamide (E163) | E102 | 3-Furanylboronic acid | 456 |
| N-[3-(cis-3,5-Dimethyl-1-piperazinyl)-4-(methyloxy)phenyl]-4-(3-furanyl)-2-methylbenzenesulfonamide (E164) | E72 | 3-Furanylboronic acid | 456 |
| N-[5-(cis-3,5-Dimethyl-1-piperazinyl)-2-(methyloxy)phenyl]-2-fluoro-4-(3-furanyl)benzenesulfonamide (E165) | E103 | 3-Furanylboronic acid | 460 |
| N-[5-(cis-3,5-Dimethyl-1-piperazinyl)-2-(methyloxy)phenyl]-2-fluoro-4-(6-methyl-2-pyridinyl)benzenesulfonamide (E166) | E103 | (6-Methyl-2-pyridinyl)boronic acid | 485 |
| 2-Chloro-N-[5-(cis-3,5-dimethyl-1-piperazinyl)-2-(methyloxy)phenyl]-4-(6-methyl-2-pyridinyl)benzenesulfonamide (E167) | E104 | (6-Methyl-2-pyridinyl)boronic acid | 501/503 |
| N-[5-(cis-3,5-Dimethyl-1-piperazinyl)-2-(methyloxy)phenyl]-2-fluoro-4-(3-thienyl)benzenesulfonamide (E168) | E103 | 3-Thienylboronic acid | 476 |
| N-[3-(cis-3,5-Dimethyl-1-piperazinyl)-4-(methyloxy)phenyl]-3-methyl-4-(2-thienyl)benzenesulfonamide (E169) | E49 | 2-Thienylboronic acid | 472 |
| N-[3-(cis-3,5-Dimethyl-1-piperazinyl)-4-(methyloxy)phenyl]-2-fluoro-4-(2-thienyl)benzenesulfonamide (E170) | E52 | 2-Thienylboronic acid | 476 |
| N-[3-(cis-3,5-Dimethyl-1-piperazinyl)-4-(methyloxy)phenyl]-2-fluoro-4-(6-methyl-2-pyridinyl)benzenesulfonamide (E171) | E52 | Bis(1,1-Dimethylethyl) (6-methyl-2-pyridinyl)boronate (WO 02/094815) | 485 |
| 2-Chloro-N-[3-(cis-3,5-dimethyl-1-piperazinyl)-4-(methyloxy)phenyl]-4-(6-methyl-2-pyridinyl)benzenesulfonamide (E172) | E51 | Bis(1,1-Dimethylethyl) (6-methyl-2-pyridinyl)boronate (WO 02/094815) | 501/503 |

-continued

| Example | Aryl Halide | Boronic acid or boronate ester | MS [M + H]+ |
|---|---|---|---|
| N-[5-(cis-3,5-Dimethyl-1-piperazinyl)-2-methylphenyl]-4-(2-thienyl)benzenesulfonamide (E173) | E81 | 2-Thienylboronic acid | 442 |
| N-[5-(cis-3,5-Dimethyl-1-piperazinyl)-2-methylphenyl]-4-(4-methyl-2-thienyl)benzenesulfonamide (E174) | E81 | (4-Methyl-2-thienyl)boronic acid | 456 |
| N-[5-(cis-3,5-Dimethyl-1-piperazinyl)-2-(methyloxy)phenyl]-3-methyl-4-(2-thienyl)benzenesulfonamide (E175) | E73 | 2-Thienylboronic acid | 472 |
| N-[5-(cis-3,5-Dimethyl-1-piperazinyl)-2-(methyloxy)phenyl]-3-methyl-4-(4-methyl-2-thienyl)benzenesulfonamide (E176) | E73 | (4-Methyl-2-thienyl)boronic acid | 486 |
| N-[3-(cis-3,5-Dimethyl-1-piperazinyl)-4-(methyloxy)phenyl]-4-(4-methyl-2-thienyl)benzenesulfonamide (E177) | E101 | (4-Methyl-2-thienyl)boronic acid | 472 |
| N-[5-(cis-3,5-Dimethyl-1-piperazinyl)-2-(methyloxy)phenyl]-2-methyl-4-(6-methyl-2-pyridinyl)benzenesulfonamide (E178) | E102 | (6-Methyl-2-pyridinyl)boronic acid | 481 |
| N-[5-(cis-3,5-Dimethyl-1-piperazinyl)-2-(methyloxy)phenyl]-3-methyl-4-(3-thienyl)benzenesulfonamide (E179) | E73 | 3-Thienylboronic acid | 472 |
| N-[5-(cis-3,5-Dimethyl-1-piperazinyl)-2-(methyloxy)phenyl]-4-(2-furanyl)-2-methylbenzenesulfonamide (E180) | E102 | 2-Furanylboronic acid | 456 |
| N-[5-(cis-3,5-Dimethyl-1-piperazinyl)-2-(methyloxy)phenyl]-2-(methyloxy)-5-(4-methyl-2-thienyl)benzenesulfonamide (E181) | E77 | (4-Methyl-2-thienyl)boronic acid | 502 |
| 2-Chloro-N-[5-(cis-3,5-dimethyl-1-piperazinyl)-2-(methyloxy)phenyl]-4-(2-thienyl)benzenesulfonamide (E182) | E104 | 2-Thienylboronic acid | 492/494 |
| 2-Chloro-N-[5-(cis-3,5-dimethyl-1-piperazinyl)-2-(methyloxy)phenyl]-4-(3-furanyl)benzenesulfonamide (E183) | E104 | 3-Furanylboronic acid | 476/478 |
| N-[5-(cis-3,5-Dimethyl-1-piperazinyl)-2-(methyloxy)phenyl]-4-(3-furanyl)-3-methylbenzenesulfonamide (E184) | E73 | 3-Furanylboronic acid | 456 |
| N-[3-(cis-3,5-Dimethyl-1-piperazinyl)-4-(methyloxy)phenyl]-4-(3-furanyl)benzenesulfonamide (E185) | E101 | 3-Furanylboronic acid | 442 |
| N-[5-(cis-3,5-Dimethyl-1-piperazinyl)-2-(methyloxy)phenyl]-2'-fluoro-4-biphenylsulfonamide (E186) | E106 | (2-Fluorophenyl)boronic acid | 470 |
| 3'-Chloro-N-[5-(cis-3,5-dimethyl-1-piperazinyl)-2-(methyloxy)phenyl]-4'-fluoro-4-biphenylsulfonamide (E187) | E106 | (3-Chloro-4-fluorophenyl)boronic acid | 504/506 |
| N-[5-(cis-3,5-Dimethyl-1-piperazinyl)-2-(methyloxy)phenyl]-2',3'-difluoro-4-biphenylsulfonamide (E188) | E106 | (2,3-Difluorophenyl)boronic acid | 488 |
| 5'-Chloro-N-[5-(cis-3,5-dimethyl-1-piperazinyl)-2-(methyloxy)phenyl]-2'-(methyloxy)-4-biphenylsulfonamide (E189) | E106 | [5-Chloro-2-(methyloxy)phenyl]boronic acid | 516/518 |
| N-[5-(cis-3,5-Dimethyl-1-piperazinyl)-2-(methyloxy)phenyl]-3'-methyl-4-biphenylsulfonamide (E190) | E106 | (3-Methylphenyl)boronic acid | 466 |
| N-[5-(cis-3,5-Dimethyl-1-piperazinyl)-2-(methyloxy)phenyl]-3-fluoro-4-(6-methyl-2-pyridinyl)benzenesulfonamide (E191) | E105 | (6-Methyl-2-pyridinyl)boronic acid | 485 |
| N-[5-(cis-3,5-Dimethyl-1-piperazinyl)-2-(methyloxy)phenyl]-5-(2-fluorophenyl)-4-methyl-2-thiophenesulfonamide (E192) | E78 | (2-Fluorophenyl)boronic acid | 490 |
| N-[5-(cis-3,5-Dimethyl-1-piperazinyl)-2-(methyloxy)phenyl]-4-methyl-5-(6-methyl-2-pyridinyl)-2-thiophenesulfonamide (E193) | E78 | (6-Methyl-2-pyridinyl)boronic acid | 487 |
| N-[5-(cis-3,5-Dimethyl-1-piperazinyl)-2-(methyloxy)phenyl]-4-methyl-5-{3-[(methyloxy)methyl]phenyl}-2-thiophenesulfonamide (E194) | E78 | {3-[(Methyloxy)methyl]phenyl}boronic acid | 516 |
| N-[5-(cis-3,5-Dimethyl-1-piperazinyl)-2-(ethyloxy)phenyl]-4-(2-thienyl)benzenesulfonamide (E195) | E99 | 2-Thienylboronic acid | 472 |

| Example | Aryl Halide | Boronic acid or boronate ester | MS [M + H]+ |
|---|---|---|---|
| N-{5-(cis-3,5-Dimethyl-1-piperazinyl)-2-[(1-methylethyl)oxy]phenyl}-4-(2-thienyl)benzenesulfonamide (E196) | E100 | 2-Thienylboronic acid | 486 |

Examples 197-211

Examples 197-211 (E197-E211) were prepared from 5-bromo-N-[5-(cis-3,5-dimethyl-1-piperazinyl)-2-(methyloxy)phenyl]-2-thiophenesulfonamide (E122) and the appropriate boronic acid indicated in the table using a similar method to that described for Examples 126-196.

| Example | Boronic acid | MS [M + H]+ |
|---|---|---|
| N-[5-(cis-3,5-Dimethyl-1-piperazinyl)-2-(methyloxy)phenyl]-5-phenyl-2-thiophenesulfonamide (E197) | Phenylboronic acid | 458 |
| 5-(2,4-Difluorophenyl)-N-[5-(cis-3,5-dimethyl-1-piperazinyl)-2-(methyloxy)phenyl]-2-thiophenesulfonamide (E198) | (2,4-Difluorophenyl)boronic acid | 494 |
| N-[5-(cis-3,5-Dimethyl-1-piperazinyl)-2-(methyloxy)phenyl]-5-[2-(ethyloxy)phenyl]-2-thiophenesulfonamide (E199) | [2-(Ethyloxy)phenyl]boronic acid | 502 |
| N-[5-(cis-3,5-Dimethyl-1-piperazinyl)-2-(methyloxy)phenyl]-4'-methyl-2,2'-bithiophene-5-sulfonamide (E200) | (4-Methyl-2-thienyl)boronic acid | 478 |
| 5-(3-Chloro-4-fluorophenyl)-N-[5-(cis-3,5-dimethyl-1-piperazinyl)-2-(methyloxy)phenyl]-2-thiophenesulfonamide (E201) | (3-Chloro-4-fluorophenyl)boronic acid | 510/512 |
| N-[5-(cis-3,5-Dimethyl-1-piperazinyl)-2-(methyloxy)phenyl]-5-(2-methylphenyl)-2-thiophenesulfonamide (E202) | (2-Methylphenyl)boronic acid | 472 |
| 5-(2,6-Dimethylphenyl)-N-[5-(cis-3,5-dimethyl-1-piperazinyl)-2-(methyloxy)phenyl]-2-thiophenesulfonamide (E203) | (2,6-Dimethylphenyl)boronic acid | 486 |
| 5-[5-Chloro-2-(methyloxy)phenyl]-N-[5-(cis-3,5-dimethyl-1-piperazinyl)-2-(methyloxy)phenyl]-2-thiophenesulfonamide (E204) | [5-Chloro-2-(methyloxy)phenyl]boronic acid | 522/524 |
| N-[5-(cis-3,5-Dimethyl-1-piperazinyl)-2-(methyloxy)phenyl]-5-(3-methylphenyl)-2-thiophenesulfonamide (E205) | (3-Methyl-2-thienyl)boronic acid | 472 |
| N-[5-(cis-3,5-Dimethyl-1-piperazinyl)-2-(methyloxy)phenyl]-5-(4-fluorophenyl)-2-thiophenesulfonamide (E206) | (4-Fluorophenyl)boronic acid | 476 |
| N-[5-(cis-3,5-Dimethyl-1-piperazinyl)-2-(methyloxy)phenyl]-5-(4-fluoro-2-methylphenyl)-2-thiophenesulfonamide (E207) | (4-Fluoro-2-methylphenyl)boronic acid | 490 |
| 5-(2-Chlorophenyl)-N-[5-(cis-3,5-dimethyl-1-piperazinyl)-2-(methyloxy)phenyl]-2-thiophenesulfonamide (E208) | (2-Chlorophenyl)boronic acid | 492/494 |
| N-[5-(cis-3,5-Dimethyl-1-piperazinyl)-2-(methyloxy)phenyl]-5-(3-fluorophenyl)-2-thiophenesulfonamide (E209) | (3-Fluorophenyl)boronic acid | 476 |
| N-[5-(cis-3,5-Dimethyl-1-piperazinyl)-2-(methyloxy)phenyl]-5-(4-methylphenyl)-2-thiophenesulfonamide (E210) | (4-Methylphenyl)boronic acid | 472 |
| 5-(3-Chlorophenyl)-N-[5-(cis-3,5-dimethyl-1-piperazinyl)-2-(methyloxy)phenyl]-2-thiophenesulfonamide (E211) | (3-Chlorophenyl)boronic acid | 492/494 |

Examples 212-227

Examples 212-227 (E212-E227) were prepared from 5-bromo-N-[3-(cis-3,5-dimethyl-1-piperazinyl)-4-(methyloxy)phenyl]-2-thiophenesulfonamide (E74) and the appropriate boronic acid indicated in the table using similar methods to that described for Examples 126-196.

A mixture of aryl halide (1 eq), boronic acid (1.5 eq), 2M aqueous sodium carbonate solution (6 eq) and bis(triphenylphosphine)palladium(II) chloride (5-10 mol %) in DME (0.05-0.4M) was stirred in a microwave reactor (set at high absorbance) at 130° C. for 30 minutes. The mixture was filtered through a hydromatrix cartridge washing with dichloromethane and the solvent was evaporated in vacuo.

| Example | Boronic acid | MS [M + H]$^+$ |
|---|---|---|
| 5-(2,4-Difluorophenyl)-N-[3-(cis-3,5-dimethyl-1-piperazinyl)-4-(methyloxy)phenyl]-2-thiophenesulfonamide (E212) | (2,4-Difluorophenyl)boronic acid | 494 |
| N-[3-(cis-3,5-Dimethyl-1-piperazinyl)-4-(methyloxy)phenyl]-5-[2-(ethyloxy)phenyl]-2-thiophenesulfonamide (E213) | [2-(Ethyloxy)phenyl]boronic acid | 502 |
| N-[3-(cis-3,5-Dimethyl-1-piperazinyl)-4-(methyloxy)phenyl]-4'-methyl-2,2'-bithiophene-5-sulfonamide (E214) | (4-Methyl-2-thienyl)boronic acid | 478 |
| N-[3-(cis-3,5-Dimethyl-1-piperazinyl)-4-(methyloxy)phenyl]-5-{3-[(methyloxy)methyl]phenyl}-2-thiophenesulfonamide (E215) | {3-[(Methyloxy)methyl]phenyl}boronic acid | 502 |
| 5-(3-Chloro-4-fluorophenyl)-N-[3-(cis-3,5-dimethyl-1-piperazinyl)-4-(methyloxy)phenyl]-2-thiophenesulfonamide (E216) | (3-Chloro-4-fluorophenyl)boronic acid | 510/512 |
| N-[3-(cis-3,5-Dimethyl-1-piperazinyl)-4-(methyloxy)phenyl]-5-(2-methylphenyl)-2-thiophenesulfonamide (E217) | (2-Methylphenyl)boronic acid | 472 |
| 5-(2,6-Dimethylphenyl)-N-[3-(cis-3,5-dimethyl-1-piperazinyl)-4-(methyloxy)phenyl]-2-thiophenesulfonamide (E218) | (2,6-Dimethylphenyl)boronic acid | 486 |
| 5-[5-Chloro-2-(methyloxy)phenyl]-N-[3-(cis-3,5-dimethyl-1-piperazinyl)-4-(methyloxy)phenyl]-2-thiophenesulfonamide (E219) | [5-Chloro-2-(methyloxy)phenyl]boronic acid | 522/524 |
| 5-(3,5-Difluorophenyl)-N-[3-(cis-3,5-dimethyl-1-piperazinyl)-4-(methyloxy)phenyl]-2-thiophenesulfonamide (E220) | (3,5-Difluorophenyl)boronic acid | 494 |
| 5-(4-Chlorophenyl)-N-[3-(cis-3,5-dimethyl-1-piperazinyl)-4-(methyloxy)phenyl]-2-thiophenesulfonamide (E221) | (4-Chlorophenyl)boronic acid | 492/494 |
| N-[3-(cis-3,5-Dimethyl-1-piperazinyl)-4-(methyloxy)phenyl]-5-(2-fluorophenyl)-2-thiophenesulfonamide (E222) | (2-Fluorophenyl)boronic acid | 476 |
| N-[3-(cis-3,5-Dimethyl-1-piperazinyl)-4-(methyloxy)phenyl]-5-(3-methylphenyl)-2-thiophenesulfonamide (E223) | (3-Methylphenyl)boronic acid | 472 |
| 5-(2,3-Difluorophenyl)-N-[3-(cis-3,5-dimethyl-1-piperazinyl)-4-(methyloxy)phenyl]-2-thiophenesulfonamide (E224) | (2,3-Difluorophenyl)boronic acid | 494 |
| 5-(2-Chlorophenyl)-N-[3-(cis-3,5-dimethyl-1-piperazinyl)-4-(methyloxy)phenyl]-2-thiophenesulfonamide (E225) | (2-Chlorophenyl)boronic acid | 492/494 |
| N-[3-(cis-3,5-Dimethyl-1-piperazinyl)-4-(methyloxy)phenyl]-5-(3-fluorophenyl)-2-thiophenesulfonamide (E226) | (3-Fluorophenyl)boronic acid | 476 |
| 5-(3-Chlorophenyl)-N-[3-(cis-3,5-dimethyl-1-piperazinyl)-4-(methyloxy)phenyl]-2-thiophenesulfonamide (E227) | (3-Chlorophenyl)boronic acid | 492/494 |

Examples 228-236

Examples 228-236 (E228-E236) were prepared using methods similar to that described below from the appropriate aryl halide and boronic acid as indicated in the table below:

The residue was applied to an SCX ion exchange cartridge (Varian bond-elute) and washed with methanol and 2M ammonia in methanol. The combined basic fractions were concentrated in vacuo and the residue purified by mass directed autoprep HPLC or chromatography on silica gel to afford the desired product which was characterized as either the free base or hydrochloride salt.

| Example | Aryl Halide | Boronic acid | MS [M + H]⁺ |
|---|---|---|---|
| N-[5-(cis-3,5-Dimethyl-1-piperazinyl)-2-fluorophenyl]-4-(2-thienyl)benzenesulfonamide (E228) | E85 | 2-Thienylboronic acid | 446 |
| N-[5-(cis-3,5-Dimethyl-1-piperazinyl)-2-fluorophenyl]-4-(3-furanyl)benzenesulfonamide (E229) | E85 | 3-Furanylboronic acid | 430 |
| N-[5-(cis-3,5-Dimethyl-1-piperazinyl)-2-fluorophenyl]-2-fluoro-4-(2-thienyl)benzenesulfonamide (E230) | E86 | 2-Thienylboronic acid | 464 |
| 2-Chloro-N-[5-(cis-3,5-dimethyl-1-piperazinyl)-2-fluorophenyl]-4-(2-thienyl)benzenesulfonamide (E231) | E87 | 2-Thienylboronic acid | 480/482 |
| 2-Chloro-N-[5-(cis-3,5-dimethyl-1-piperazinyl)-2-fluorophenyl]-4-(3-furanyl)benzenesulfonamide (E232) | E87 | 3-Furanylboronic acid | 464/466 |
| N-[5-(cis-3,5-Dimethyl-1-piperazinyl)-2-fluorophenyl]-2-methyl-4-(2-thienyl)benzenesulfonamide (E233) | E88 | 2-Thienylboronic acid | 460 |
| N-[5-(cis-3,5-Dimethyl-1-piperazinyl)-2-fluorophenyl]-4-(3-furanyl)-2-methylbenzenesulfonamide (E234) | E88 | 3-Furanylboronic acid | 444 |
| N-[5-(cis-3,5-Dimethyl-1-piperazinyl)-2-fluorophenyl]-3-fluoro-4-(2-thienyl)benzenesulfonamide (E235) | E89 | 2-Thienylboronic acid | 464 |
| N-[5-(cis-3,5-Dimethyl-1-piperazinyl)-2-fluorophenyl]-3-fluoro-4-(3-furanyl)benzenesulfonamide (E236) | E89 | 3-Furanylboronic acid | 448 |

Examples E237-E243

Examples 237-243 (E237-243) were prepared using methods similar to that described below from the appropriate aryl bromide and boronic acid as indicated in the table below:

A mixture of aryl bromide (1 eq), boronic acid (2 eq), 1M aqueous sodium carbonate solution (5 eq) and tetrakis(triphenylphosphine)palladium(0) (5-10 mol %) in 1:1 toluene:ethanol (0.05-0.2M) was stirred at reflux under an atmosphere of argon for 1-18 hours. After cooling to room temperature the reaction mixture was applied to an SCX ion exchange cartridge (Varian bond-elute) and washed with methanol and 2M ammonia in methanol. The combined basic fractions were concentrated in vacuo and the residue purified by mass directed autoprep HPLC or chromatography on silica gel to afford the desired product which was characterized as either the free base or hydrochloride salt.

| Example | Aryl Halide | Boronic acid | MS [M + H]⁺ |
|---|---|---|---|
| N-[3-(cis-3,5-Dimethyl-1-piperazinyl)-4-(methyloxy)phenyl]-2-(methyloxy)-4-(2-thienyl)benzenesulfonamide (E237) | E82 | 2-Thienylboronic acid | 488 |
| N-[5-(cis-3,5-Dimethyl-1-piperazinyl)-2-fluoro-4-(methyloxy)phenyl]-4-(2-thienyl)benzenesulfonamide (E238) | E90 | 2-Thienylboronic acid | 476 |
| N-[5-(cis-3,5-Dimethyl-1-piperazinyl)-2-(methyloxy)phenyl]-5-(3-furanyl)-2-thiophenesulfonamide (E239) | E122 | 3-Furanylboronic acid | 448 |
| 5-(2,3-Difluorophenyl)-N-[5-(cis-3,5-dimethyl-1-piperazinyl)-2-(methyloxy)phenyl]-2-thiophenesulfonamide (E240) | E122 | (2,3-Difluorophenyl)boronic acid | 494 |

-continued

| Example | Aryl Halide | Boronic acid | MS [M + H]+ |
|---|---|---|---|
| N-[5-(cis-3,5-Dimethyl-1-piperazinyl)-2-(methyloxy)phenyl]-5'-methyl-2,2'-bithiophene-5-sulfonamide (E241) | E122 | (5-Methyl-2-thienyl)boronic acid | 478 |
| N-[3-(cis-3,5-Dimethyl-1-piperazinyl)-4-(methyloxy)phenyl]-5-(3-furanyl)-2-thiophenesulfonamide (E242) | E74 | 3-Furanylboronic acid | 448 |
| N-[3-(cis-3,5-Dimethyl-1-piperazinyl)-4-(methyloxy)phenyl]-5'-methyl-2,2'-bithiophene-5-sulfonamide (E243) | E74 | (5-Methyl-2-thienyl)boronic acid | 478 |

Example 244

N-[5-(cis-3,5-Dimethyl-1-piperazinyl)-2,4-bis(methyloxy)phenyl]-4-(2-thienyl)benzenesulfonamide (E244)

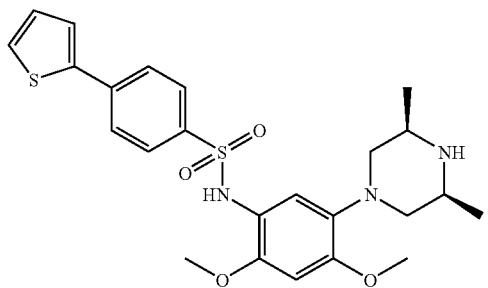

Step 1: N-[5-(cis-3,5-Dimethyl-1-piperazinyl)-2,4-bis(methyloxy)phenyl]-4-iodobenzenesulfonamide The title compound was prepared from 5-(cis-3,5-dimethyl-1-piperazinyl)-2,4-bis(methyloxy)aniline (D25) and 4-iodobenzenesulfonyl chloride using a similar procedure to that described for Example 81. MS (ES+) m/e 532 [M+H]+.

Step 2: N-[5-(cis-3,5-Dimethyl-1-piperazinyl)-2,4-bis(methyloxy)phenyl]-4-(2-thienyl)benzenesulfonamide (E244)

The title compound (E244) was prepared from the product of Step 1 and 2-thienylboronic acid using a similar method to that described for Examples 237-243. MS (ES+) m/e 488 [M+H]+.

Example 245

N-{3-(cis-3,5-Dimethyl-1-piperazinyl)-4-[(trifluoromethyl)oxy]phenyl}-4-(2-thienyl)benzenesulfonamide (E245)

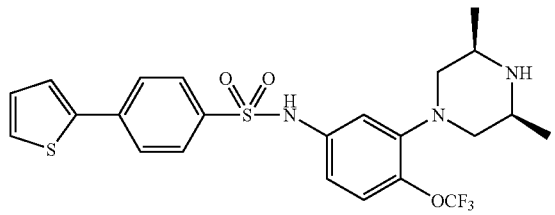

Step 1: N-{3-Bromo-4-[(trifluoromethyl)oxy]phenyl}-4-iodobenzenesulfonamide

The title compound was prepared from 3-bromo-4-[(trifluoromethyl)oxy]aniline and 4-iodobenzenesulfonyl chloride using a similar method to that described for Examples 82-100. MS (ES−) m/e 520/522 [M−H]−.

Step 2: N-{3-Bromo-4-[(trifluoromethyl)oxy]phenyl}-4-(2-thienyl)benzenesulfonamide The title compound was prepared from the product of Step 1 and 2-thienylboronic acid using a similar method to that described for Examples 126-196. MS (ES−) m/e 476/478 [M−H]−.

Step 3: N-{3-(cis-3,5-Dimethyl-1-piperazinyl)-4-[(trifluoromethyl)oxy]phenyl}-4-(2-thienyl)benzenesulfonamide (E245)

The product of Step 2 (162 mg, 0.34 mmol), cis-2,6-dimethyl piperazine (78 mg, 0.68 mmol), sodium tert-butoxide (169 mg, 0.68 mmol), tris(dibenzylideneacetone)dipalladium(0) (16 mg, 0.017 mmol) and 2-dicyclohexylphosphino-2'-(N,N-dimethylamino)biphenyl (20 mg, 0.051 mmol) in dioxane (4 ml) were heated in a microwave reactor at 125° C. for 30 minutes. The reaction mixture was applied to an SCX ion exchange cartridge (Varian bond-elute) and washed with methanol and 2M ammonia in methanol. The combined basic fractions were concentrated in vacuo and the residue purified by mass directed autoprep HPLC to afford the title compound (E245). MS (ES+) m/e 512 [M+H]+.

Example 246

N-{3-(cis-3,5-Dimethyl-1-piperazinyl)-4-[(trifluoromethyl)oxy]phenyl}-5-(2-pyridinyl)-2-thiophenesulfonamide (E246)

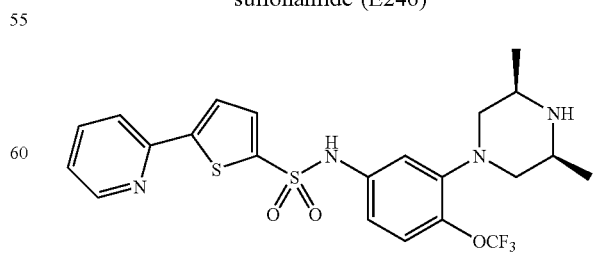

The title compound (E246) was prepared from 3-bromo-4-[(trifluoromethyl)oxy]aniline and 5-(2-pyridinyl)-2- thiophenesulfonyl chloride using a similar method to that described for Example 245 (Step 1 followed by Step 3). MS (ES+) m/e 513 [M+H]+.

Example 247

N-[5-(cis-3,5-Dimethyl-1-piperazinyl)-2-(methyloxy)phenyl]-4-(5-methyl-2-furanyl)benzenesulfonamide (E247)

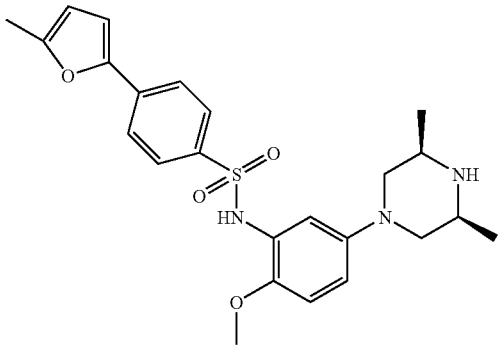

Step 1. 5-(cis-3,5-Dimethyl-1-piperazinyl)-2-(methyloxy)aniline trihydrochloride A mixture of cis-3,5-dimethyl-1-[4-(methyloxy)-3-nitrophenyl]piperazine (D3) (74 g, 279 mmol) was dissolved in ethanol (500 ml) and hydrogenated (palladium on charcoal 7.4 g, 10% paste) at room temperature under one atmosphere of hydrogen gas overnight. The catalyst was filtered, washed with ethanol and concentrated. The residue was re-dissolved in methanol and treated drop-wise with a solution of 4M HCl in dioxane (140 ml, 560 mmol). The solution was filtered through charcoal and concentrated to a solid. The solid residue was triturated with ether and dried in a vacuum oven to afford the title compound. MS (ES+) m/e 236 [M+H]+.

Step 2. 4-Bromo-N-[5-(cis-3,5-dimethyl-1-piperazinyl)-2-(methyloxy)phenyl]benzenesulfonamide 5-(cis-3,5-Dimethyl-1-piperazinyl)-2-(methyloxy)aniline trihydrochloride (40.66 g, 118 mmol) was slurried in dichloromethane (300 ml) cooled 0° C. and treated with pyridine (300 ml). 4-Bromobenzenesulfonyl chloride (33.20 g, 130 mmol) dissolved in dichloromethane (300 ml) was added drop-wise and the solution stirred at room temperature for 3 hours. The mixture was concentrated in vacuo and partitioned between ethyl acetate and saturated sodium bicarbonate solution. Insoluble material was filtered, washed with water and a small volume of ethyl acetate and pentane added to afford the hydrochloride salt of the title product. The filtrate was washed with saturated sodium bicarbonate solution, water (×3), brine, dried over anhydrous sodium sulfate and concentrated in vacuo to a crude solid. This was then titurated with pentane and filtered. The hydrochloride salt obtained earlier was partitioned with 0.880 ammonia solution in dichloromethane and extracted with dichloromethane (×5). The combined extracts were washed with water, brine (×2), dried over anhydrous sodium sulfate and concentrated to a solid. All aqueous material was basified with 0.880 ammonia solution, extracted with dichloromethane and concentrated. Residue was dissolved in ethyl acetate, washed in water, brine and dried over anhydrous sodium sulphate to afford a solid. Solids were purified by flash chromatography on silica gel (Biotage Flash 75+L, dichloromethane 1:10 2M ammonia in methanol: dichloromethane) to give the title compound. MS (ES+) m/e 454/456 [M+H]+.

Step 3. N-[5-(cis-3,5-Dimethyl-1-piperazinyl)-2-(methyloxy)phenyl]-4-(5-methyl-2-furanyl)benzenesulfonamide (E247)

4-Bromo-N-[5-(cis-3,5-dimethyl-1-piperazinyl)-2-(methyloxy)phenyl]benzenesulfonamide (32.96 g, 72.5 mmol) was suspended in 1,2-dimethoxyethane (300 ml) and treated with sodium carbonate (38.4 g, 363 mmol) dissolved in water (150 ml). (5-Methyl-2-furanyl)boronic acid (13.7 g, 109 mmol) and bis(triphenylphosphine)palladium(II) chloride (108 mg, 0.15 mmol) were added and the mixture was heated at reflux for 1.5 hours. The mixture was cooled and diluted with ethyl acetate, charcoal added and the mixture was stirred with charcoal for 45 minutes. The mixture was filtered through celite, the filtrate separated and washed with saturated sodium bicarbonate solution, water (×3), brine, dried over anhydrous sodium sulfate and concentrated to a crude solid, titrated with pentane and filtered. The combined residues were purified by flash chromatography (Biotage Flash 75+L, dichloromethane to 1:10 2M ammonia in methanol: dichloromethane) followed by trituration with pentane to give the title compound (E247). MS (ES+) m/e 456 [M+H]+.

The title compound (33.13 g, 72.7 mmol) was slurried in methanol (400 ml) at 0° C. 1M HCl in diethylether (80 ml, 0.8 mmol) was added dropwise and the solution stirred at room temperature for 15 minutes. The solution was concentrated in vacuo, azeotroped with ether (×3), triturated with ether, filtered, washed with ether and then dried in a vacuum oven at 40° C. overnight to afford a solid containing ca. 6% diethyl ether (w/w). The solid was dried in a vacuum over at 60° C. for 4 hours and was found to contain ca. 4% diethyl ether (w/w). After drying at 60° C. in a vacuum over overnight, the diethyl ether content was found to be 3% (w/w). The solid was slurried in hot ethyl acetate and methanol added until solids dissolved. The solution was azeotroped until solids appeared, whereupon it was allowed to cool overnight. The solid was filtered, slurried in ethyl acetate (×3), filtered and dried in a vacuum oven at 50° C. overnight to afford the hydrochloride salt of the title compound.

Example 248

N-[5-(cis-3,5-Dimethyl-1-piperazinyl)-2-(methyloxy)phenyl]-3-fluoro-4-(5-methyl-2-furanyl)benzenesulfonamide (E248)

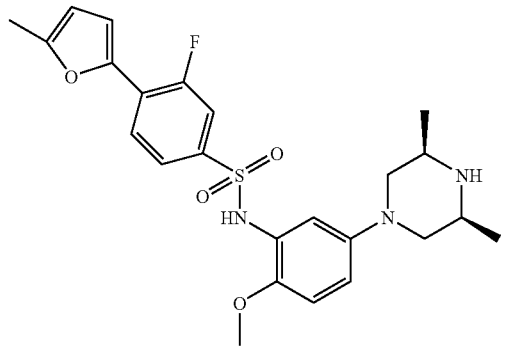

Step 1. 4-Bromo-N-[5-(cis-3,5-dimethyl-1-piperazinyl)-2-(methyloxy)phenyl]-3-fluorobenzenesulfonamide To a solution of 5-(cis-3,5-dimethyl-1-piperazinyl)-2-(methyloxy)aniline D4 (2.50 g, 10.62 mmol) in dichloromethane (50 ml) was added pyridine (53 ml) followed by 4-bromo-3-fluorobenzenesulfonyl chloride (5.81 g, 21.24 mmol) dissolved in dichloromethane (2 ml+1 ml), the latter being added drop-wise over 1-2 min. The resulting orange-red solution was stirred at room temperature, under Argon for 4 hours and was then reduced under vacuum and azeotroped with methanol (×3). The residue was then partitioned between dichloromethane (250 ml) and saturated sodium bicarbonate solution (250 ml), the layers separated and the aqueous re-extracted with dichloromethane (250 ml). The organic layers were combined and washed with brine (500 ml), dried over anhydrous magnesium sulfate, filtered and reduced. The residue was purified by column chromatography (SPE, Si, 50 g eluting with dichloromethane: methanol 50:1 to 5:1) to give pure fractions which were azeotroped and then triturated with hexane: diethyl ether (5:1) to give the title product. MS (ES+) m/e 472/474 [M+H]$^+$.

Step 2. N-[5-(cis-3,5-Dimethyl-1-piperazinyl)-2-(methyloxy)phenyl]-3-fluoro-4-(5-methyl-2-furanyl)benzenesulfonamide (E248)

A stirred suspension of 4-bromo-N-[5-(cis-3,5-dimethyl-1-piperazinyl)-2-(methyloxy)phenyl]-3-fluorobenzenesulfonamide (3.4 g, 7.2 mmol) in 1,2-dimethoxyethane (80 ml) was treated with a solution of sodium carbonate (3.8 g, 36 mmol) in water (20 ml). (5-Methyl-2-furanyl)boronic acid (1.4 g, 10.8 mmol) and bis(triphenylphosphine)palladium(II) chloride (10 mg, 0.2 mol %) were added with some water and the mixture was stirred at reflux for 3 hours. Additional (5-methyl-2-furanyl)boronic acid (420 mg, 3.3 mmol) was added and the mixture was heated at reflux for a further 30 minutes. After cooling to room temperature, ethyl acetate (50 ml), water (50 ml) and charcoal (3 g) were added and the mixture was stirred at room temperature for 30 minutes. The mixture was filtered through celite, the ethyl acetate layer separated and the aqueous layer was further extracted with ethyl acetate. The ethyl acetate extracts were combined washed with water and brine dried over anhydrous sodium sulfate and evaporated. The residue was purified by chromatography on a 100 g column eluting with 1:40 to 1:10 2M ammonia in methanol: dichloromethane. Residue was then triturated in ether, dissolved in ether/pentane and evaporated. Residue was then triturated in pentane, washed in pentane, air dried and then dried at 50° C. under argon and high vacuum to give the title compound (E248). MS (ES+) m/e 474 [M+H]$^+$.

The hydrochloride salt of the product was prepared by dissolving pure material in methanol and acidifying with ethereal HCl. After 5 mins at room temperature the solvent was evaporated and the mixture co-evaporated in ether (×2).The residue was triturated in ether, a small amount of ethyl acetate and methanol added to remove colour and the solid collected, washed in ether and dried.

Examples 249-253

Examples 249-253 (E249-E253) were prepared from the aniline and the sulfonyl chloride listed in the table using a similar method to that described for Examples 69-81 (E69-E81):

| Example | Sulfonyl Chloride | Aniline | MS [M + H]$^+$ |
|---|---|---|---|
| N-[5-(cis-3,5-Dimethyl-1-piperazinyl)-2-(methyloxy)phenyl]-5-(2-methyl-1,3-thiazol-4-yl)-2-thiophenesulfonamide (E249) | 5-(2-Methyl-1,3-thiazol-4-yl)-2-thiophenesulfonyl chloride | D4 | 479 |
| N-[5-(cis-3,5-Dimethyl-1-piperazinyl)-2-(methyloxy)phenyl]-4-methyl-3,4-dihydro-2H-1,4-benzoxazine-7-sulfonamide (E250) | 4-Methyl-3,4-dihydro-2H-1,4-benzoxazine-7-sulfonyl chloride | D4 | 447 |
| 4-Bromo-N-[3-(cis-3,5-dimethyl-1-piperazinyl)phenyl]-2-(methyloxy)benzenesulfonamide (E251) | 4-Bromo-2-(methyloxy)benzenesulfonyl chloride (D30) | D21 | 454/456 |
| N-[2-Chloro-5-(cis-3,5-dimethyl-1-piperazinyl)phenyl]-5-(2-pyridinyl)-2-thiophenesulfonamide (E252) | 5-(2-Pyridinyl)-2-thiophenesulfonyl chloride | D34 | 463/465 |
| 4-Bromo-N-[5-(cis-3,5-dimethyl-1-piperazinyl)-2-(methyloxy)phenyl]-1-naphthalenesulfonamide (E253) | 4-Bromo-1-naphthalenesulfonyl chloride | D4 | 504/506 |

Example 254

5-(5-Chloro-1,2,4-thiadiazol-3-yl)-N-[5-(cis-3,5-dimethyl-1-piperazinyl)-2-(methyloxy)phenyl]-2-thiophenesulfonamide (E254)

A solution of 5-(cis-3,5-dimethyl-1-piperazinyl)-2-(methyloxy)aniline (D4) (33 mg, 0.14 mmol) in dichloromethane (2 ml) and pyridine (0.5 ml) was treated with 5-(5-chloro-1,2,4-thiadiazol-3-yl)-2-thiophenesulfonyl chloride (50 mg, 0.17 mmol) and the resulting mixture stirred at room temperature overnight. The mixture was then concentrated in vacuo, co-evaporated with toluene and the crude product purified by mass directed autoprep HPLC to afford the desired product which was characterized as the hydrochloride salt. MS (ES+) m/e 500/502 [M+H]$^+$.

Examples 255-259

Examples 255-259 (E255-E259) were prepared using methods similar to that described below from 5-(cis-3,5-dimethyl-1-piperazinyl)-2-(methyloxy)aniline (D4) and the appropriate sulfonyl chloride listed in the table:

A solution of 5-(cis-3,5-dimethyl-1-piperazinyl)-2-(methyloxy)aniline (D4) (100 mg, 0.43 mmol) in dichloromethane (1 ml) and pyridine (3 ml) was treated with the appropriate sulfonyl chloride (1.2 eq) and the resulting solution stirred at room temperature for 2 hours. The mixture was then concentrated in vacuo and the crude product purified by mass directed autoprep HPLC to afford the desired product which was characterized as either the free base or hydrochloride salt.

| Example | Sulfonyl Chloride | MS [M + H]+ |
|---|---|---|
| 2-Bromo-N-[5-(cis-3,5-dimethyl-1-piperazinyl)-2-(methyloxy)phenyl]-4-(trifluoromethyl)benzenesulfonamide (E255) | 2-Bromo-4-(trifluoromethyl)benzenesulfonyl chloride | 522/524 |
| 4-Bromo-2,6-dichloro-N-[5-(cis-3,5-dimethyl-1-piperazinyl)-2-(methyloxy)phenyl]benzenesulfonamide (E256) | 4-Bromo-2,6-dichlorobenzenesulfonyl chloride | 522/524/526 |
| 2,6-Dichloro-N-[5-(cis-3,5-dimethyl-1-piperazinyl)-2-(methyloxy)phenyl]benzenesulfonamide (E257) | 2,6-Dichlorobenzenesulfonyl chloride | 444/446/448 |
| 2,4-Dibromo-N-[5-(cis-3,5-dimethyl-1-piperazinyl)-2-(methyloxy)phenyl]benzenesulfonamide (E258) | 2,4-Dibromobenzenesulfonyl chloride | 532/534/536 |
| 2,4-Dichloro-N-[5-(cis-3,5-dimethyl-1-piperazinyl)-2-(methyloxy)phenyl]-5-methylbenzenesulfonamide (E259) | 2,4-Dichloro-5-methylbenzenesulfonyl chloride | 458/460/462 |

Examples 260 and 261

Examples 260 and 261 (E260 and E261) were prepared from the appropriate aniline and sulfonyl chloride listed in the table using similar methods to that described for Examples 82-100 (E82-E100):

| Example | Sulfonyl Chloride | Aniline | MS [M + H]+ |
|---|---|---|---|
| 4-Bromo-N-[5-(cis-3,5-dimethyl-1-piperazinyl)-2-fluorophenyl]-2-(methyloxy)benzenesulfonamide (E260) | 4-Bromo-2-(methyloxy)benzenesulfonyl chloride (D30) | D13 | 472/474 |
| 4-Bromo-N-[5-(cis-3,5-dimethyl-1-piperazinyl)-2-fluorophenyl]-3-methylbenzenesulfonamide (E261) | 4-Bromo-3-methylbenzenesulfonyl chloride | D13 | 456/458 |

Examples 262-267

Examples 262-267 (E262-E267) were prepared from the appropriate aryl halide and boronic acid using similar methods to that described for Examples 228-236 (E228-E236):

| Example | Aryl Halide | Boronic acid | MS [M + H]+ |
|---|---|---|---|
| N-[5-(cis-3,5-Dimethyl-1-piperazinyl)-2-fluorophenyl]-2-(methyloxy)-4-(2-thienyl)benzenesulfonamide (E262) | E260 | 2-Thienylboronic acid | 476 |
| N-[5-(cis-3,5-Dimethyl-1-piperazinyl)-2-fluorophenyl]-4-(3-furanyl)-2-(methyloxy)benzenesulfonamide (E263) | E260 | 3-Furanylboronic acid | 460 |
| N-[5-(cis-3,5-Dimethyl-1-piperazinyl)-2-fluorophenyl]-2-(methyloxy)-4-(4-methyl-2-thienyl)benzenesulfonamide (E264) | E260 | (4-Methyl-2-thienyl)boronic acid | 490 |
| N-[5-(cis-3,5-Dimethyl-1-piperazinyl)-2-fluorophenyl]-4-(4-methyl-2-thienyl)benzenesulfonamide (E265) | E85 | (4-Methyl-2-thienyl)boronic acid | 460 |
| N-[5-(cis-3,5-Dimethyl-1-piperazinyl)-2-fluorophenyl]-2-methyl-4-(4-methyl-2-thienyl)benzenesulfonamide (E266) | E88 | (4-Methyl-2-thienyl)boronic acid | 474 |
| N-[5-(cis-3,5-Dimethyl-1-piperazinyl)-2-fluorophenyl]-3-methyl-4-(4-methyl-2-thienyl)benzenesulfonamide (E267) | E261 | (4-Methyl-2-thienyl)boronic acid | 474 |

Examples 268-271

Examples 268-271 (E268-E271) were prepared using methods similar to that described below from aryl iodide (E34) and appropriate stannane indicated in the table below:

A mixture of N-[5-(cis-3,5-dimethyl-1-piperazinyl)-2-(methyloxy)phenyl]-4-iodobenzenesulfonamide (E34) (1 eq), stannane (3 eq) and bis(triphenylphosphine)palladium (II) chloride (10 mol %) in dioxane (ca. 0.07M) was heated at reflux for 1-24 hours. After cooling to room temperature a solution of potassium fluoride (ca. 5.2 eq) in water (ca. 0.33M) was added. The mixture was applied to an SCX ion exchange cartridge (Varian bond-elute) and washed with methanol and 2M ammonia in methanol. The combined basic fractions were concentrated in vacuo and the residue purified by mass directed autoprep HPLC or chromatography on silica gel to afford the desired product which was characterized as either the free base or hydrochloride salt.

| Example | Stannane | MS [M + H]⁺ |
|---|---|---|
| N-[5-(cis-3,5-Dimethyl-1-piperazinyl)-2-(methyloxy)phenyl]-4-(1,3-thiazol-2-yl)benzenesulfonamide (E268) | 2-(Tributylstannanyl)-1,3-thiazole | 459 |
| N-[5-(cis-3,5-Dimethyl-1-piperazinyl)-2-(methyloxy)phenyl]-4-(1-methyl-1H-pyrrol-2-yl)benzenesulfonamide (E269) | 1-Methyl-2-(tributylstannanyl)-1H-pyrrole | 455 |
| N-[5-(cis-3,5-Dimethyl-1-piperazinyl)-2-(methyloxy)phenyl]-4-(2-pyrazinyl)benzenesulfonamide (E270) | 2-(Tributylstannanyl)pyrazine | 454 |
| N-[5-(cis-3,5-Dimethyl-1-piperazinyl)-2-(methyloxy)phenyl]-4-(2-pyrimidinyl)benzenesulfonamide (E271) | 2-(Tributylstannanyl)pyrimidine | 454 |

Example 272

N-[5-(cis-3,5-Dimethyl-1-piperazinyl)-2-(methyloxy)phenyl]-6-(2-furanyl)-3-pyridinesulfonamide (E272)

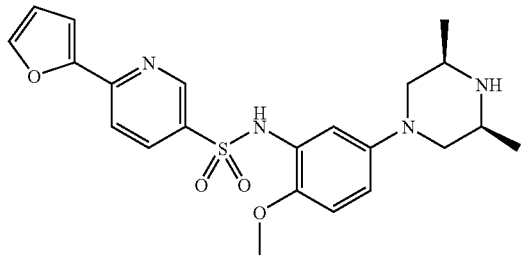

Step 1: 6-Chloro-N-[5-(cis-3,5-dimethyl-1-piperazinyl)-2-(methyloxy)phenyl]-3-pyridinesulfonamide A solution of 5-(cis-3,5-dimethyl-1-piperazinyl)-2-(methyloxy)aniline (D4) (587 mg, 2.5 mmol) in dichloromethane (4 ml) and pyridine (4 ml) was treated with a suspension of 6-chloro-3-pyridinesulfonyl chloride hydrochloride (D32) (700 mg, 3 mmol) in dichloromethane (4 ml). After stirring at room temperature for 15 minutes the mixture was evaporated and the residue co-evaporated with toluene (×2). The residue was then partitioned between dichloromethane and saturated aqueous sodium bicarbonate solution. The organic layer was separated, washed in water, brine, dried and evaporated. The residue was triturated with ether/and dried to give the title product. MS (ES+) 411/413 [M+H]⁺.

Step 2: N-[5-(cis-3,5-Dimethyl-1-piperazinyl)-2-(methyloxy)phenyl]-6-(2-furanyl)-3-pyridinesulfonamide (E272)

A mixture of the product of Step 1 (205 mg, 0.5 mmol), 2-furanylboronic acid (112 mg, 2 mmol), 1M sodium carbonate solution (2.5 ml, 2.5 mmol) and tetrakis(triphenylphosphine)palladium(0) (58 mg, 0.05 mmol) in 1:1 toluene:ethanol (10 ml) was stirred at reflux under an atmosphere of argon for 1.5 hours. After cooling to room temperature the reaction mixture was acidified with 2N hydrochloric acid and applied to a 10 g SCX column and eluted in methanol then 2M ammonia in methanol. The combined basic fractions were concentrated in vacuo. The crude residue was purified by mass directed autoprep to afford the title product (E272). MS (ES+) 443 [M+H]⁺.

Examples 273-275

Examples 273-275 (E273-E275) were prepared from 6-chloro-N-[5-(cis-3,5-dimethyl-1-piperazinyl)-2-(methyloxy)phenyl]-3-pyridinesulfonamide (Product of E272 Step 2) and the appropriate boronic acid as indicated in the Table below using similar methods to that described for Example 272, Step 2:

| Example | Boronic acid | MS [M + H]⁺ |
|---|---|---|
| N-[5-(cis-3,5-Dimethyl-1-piperazinyl)-2-(methyloxy)phenyl]-6-(2-thienyl)-3-pyridinesulfonamide (E273) | 2-Thienylboronic acid | 459 |
| N-[5-(cis-3,5-Dimethyl-1-piperazinyl)-2-(methyloxy)phenyl]-6-(5-methyl-2-furanyl)-3-pyridinesulfonamide (E274) | (5-Methyl-2-furanyl)boronic acid | 457 |
| N-[5-(cis-3,5-Dimethyl-1-piperazinyl)-2-(methyloxy)phenyl]-6-(4-methyl-2-thienyl)-3-pyridinesulfonamide (E275) | (4-Methyl-2-thienyl)boronic acid | 473 |

Example 276

N-[5-(cis-3,5-Dimethyl-1-piperazinyl)-2-(methyloxy)phenyl]-5-(5-methyl-2-furanyl)-2-pyridinesulfonamide (E276)

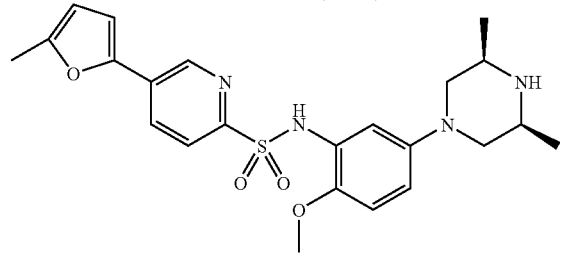

Step 1: 5-Bromo-N-[5-(cis-3,5-dimethyl-1-piperazinyl)-2-(methyloxy)phenyl]-2-pyridinesulfonanide The title compound was prepared from 5-(cis-3,5-dimethyl-1-piperazinyl)-2-(methyloxy)aniline (D4) and 5-bromo-2-pyridinesulfonyl chloride (D33) using a similar method to that described for Example 272, Step 1. MS (ES+) 455/457 [M+H]⁺.

Step 2: N-[5-(cis-3,5-Dimethyl-1-piperazinyl)-2-(methyloxy)phenyl]-5-(5-methyl-2-furanyl)-2-pyridinesulfonamide (E276)

The title compound (E276) was prepared from the product of Step 1 and (5-methyl-2-furanyl)boronic acid using a similar method to that described for Example 272, Step 2. MS (ES+) 457 [M+H]⁺.

Example 277

N-[2-(Methyloxy)-5-(cis-3,4,5-trimethyl-1-piperazinyl)phenyl]-4-(2-thienyl)benzenesulfonamide (E277)

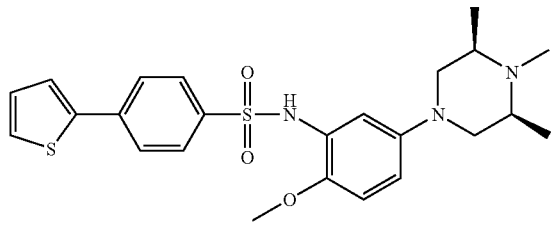

Step 1: N-[5-Bromo-2-(methyloxy)phenyl]-4-iodobenzenesulfonamide

The title compound was prepared from 5-bromo-2-(methyloxy)aniline and 4-iodobenzenesulfonyl chloride using a similar method to that described for Examples 82-100 (E82-E100). MS (ES−) 466/468 [M−H]⁻.

Step 2: N-[5-Bromo-2-(methyloxy)phenyl]-4-(2-thienyl)benzenesulfonamide

The title compound was prepared from the product of Step 1 and 2-thienylboronic acid using a similar method to that described for Examples 237-243 (E237-E243). MS (ES−) 422/424 [M−H]⁻.

Step 3: N-[2-(Methyloxy)-5-(cis-3,4,5-trimethyl-1-piperazinyl)phenyl]-4-(2-thienyl)benzenesulfonamide (E277)

The product of Step 2 (200 mg, 0.47 mmol), cis-1,2,6-trimethyl piperazine (118 mg, 0.94 mmol), sodium tert-butoxide (90 mg, 0.94 mmol), tris(dibenzylideneacetone)dipalladium(0) (22 mg, 0.024 mmol) and 2-dicyclohexylphosphino-2'-(N,N-dimethylamino)biphenyl (28 mg, 0.071 mmol) in dioxane (10 ml) was heated at reflux for 16 hours. After cooling to room temperature the solution was concentrated in vacuo. The residue was applied to an SCX ion exchange cartridge (Varian bond-elute) and washed with methanol and 2M ammonia in methanol. The combined basic fractions were concentrated in vacuo and the residue purified by mass directed autoprep to afford the title product (E277). MS (ES+) 472 [M+H]⁺.

Examples 278-298

Examples 278-298 (E278-E298) were prepared from the appropriate aryl halide and boronic acid indicated in the table using similar methods to that described for Examples 126-196 (E126-E196):

| Example | Aryl Halide | Boronic acid | MS [M + H]⁺ |
|---|---|---|---|
| 2-Chloro-N-[5-(cis-3,5-dimethyl-1-piperazinyl)-2-(methyloxy)phenyl]-4-(3-thienyl)benzenesulfonamide (E278) | E104 | 3-Thienylboronic acid | 492/494 |
| 2-Chloro-N-[5-(cis-3,5-dimethyl-1-piperazinyl)-2-(methyloxy)phenyl]-4-(5-methyl-2-thienyl)benzenesulfonamide (E279) | E104 | (5-Methyl-2-thienyl)boronic acid | 506/508 |
| N-[5-(cis-3,5-Dimethyl-1-piperazinyl)-2-(methyloxy)phenyl]-3-(2-furanyl)benzenesulfonamide (E280) | E76 | 2-Furanylboronic acid | 442 |
| N-[5-(cis-3,5-Dimethyl-1-piperazinyl)-2-(methyloxy)phenyl]-3-(3-furanyl)benzenesulfonamide (E281) | E76 | 3-Furanylboronic acid | 442 |
| N-[5-(cis-3,5-Dimethyl-1-piperazinyl)-2-(methyloxy)phenyl]-3-(4-methyl-2-thienyl)benzenesulfonamide (E282) | E76 | (4-Methyl-2-thienyl)boronic acid | 472 |
| N-[5-(cis-3,5-Dimethyl-1-piperazinyl)-2-(methyloxy)phenyl]-3-methyl-4-(5-methyl-2-thienyl)benzenesulfonamide (E283) | E73 | (5-Methyl-2-thienyl)boronic acid | 486 |
| N-[3-(cis-3,5-Dimethyl-1-piperazinyl)phenyl]-2-(methyloxy)-4-(4-methyl-2-thienyl)benzenesulfonamide (E284) | E251 | (4-Methyl-2-thienyl)boronic acid | 472 |
| N-[3-(cis-3,5-Dimethyl-1-piperazinyl)phenyl]-4-(2-furanyl)-2-(methyloxy)benzenesulfonamide (E285) | E251 | 2-Furanylboronic acid | 442 |
| N-[3-(cis-3,5-Dimethyl-1-piperazinyl)phenyl]-2-(methyloxy)-4-(2-thienyl)benzenesulfonamide (E286) | E251 | 2-Thienylboronic acid | 458 |
| N-[5-(cis-3,5-Dimethyl-1-piperazinyl)-2-(methyloxy)phenyl]-2-methyl-4-(3-thienyl)benzenesulfonamide (E287) | E102 | 3-Thienylboronic acid | 472 |
| N-[5-(cis-3,5-Dimethyl-1-piperazinyl)-2-(methyloxy)phenyl]-2-fluoro-4-(5-methyl-2-thienyl)benzenesulfonamide (E288) | E103 | (5-Methyl-2-thienyl)boronic acid | 490 |
| N-[5-(cis-3,5-Dimethyl-1-piperazinyl)-2-(methyloxy)phenyl]-2,5-difluoro-4-(4-methyl-2-thienyl)benzenesulfonamide (E289) | D37 | (4-Methyl-2-thienyl)boronic acid | 508 |

-continued

| Example | Aryl Halide | Boronic acid | MS [M + H]+ |
|---|---|---|---|
| N-[5-(cis-3,5-Dimethyl-1-piperazinyl)-2-(methyloxy)phenyl]-2-methyl-4-(5-methyl-2-thienyl)benzenesulfonamide (E290) | E102 | (5-Methyl-2-thienyl)boronic acid | 486 |
| N-[5-(cis-3,5-Dimethyl-1-piperazinyl)-2-(methyloxy)phenyl]-3-fluoro-4-(3-thienyl)benzenesulfonamide (E291) | E105 | 3-Thienylboronic acid | 476 |
| N-[5-(cis-3,5-Dimethyl-1-piperazinyl)-2-(methyloxy)phenyl]-3-fluoro-4-(5-methyl-2-thienyl)benzenesulfonamide (E292) | E105 | (5-Methyl-2-thienyl)boronic acid | 490 |
| N-[5-(cis-3,5-Dimethyl-1-piperazinyl)-2-(methyloxy)phenyl]-2,5-difluoro-4-(2-furanyl)benzenesulfonamide (E293) | D37 | 2-Furanylboronic acid | 478 |
| N-[5-(cis-3,5-Dimethyl-1-piperazinyl)-2-(methyloxy)phenyl]-5-(3-pyridinyl)-2-thiophenesulfonamide (E294) | E122 | 3-Pyridinylboronic acid | 459 |
| N-[3-(cis-3,5-Dimethyl-1-piperazinyl)-4-(methyloxy)phenyl]-2'-methyl-4-biphenylsulfonamide (E295) | E101 | (2-Methylphenyl)boronic acid | 466 |
| N-[3-(cis-3,5-Dimethyl-1-piperazinyl)-4-(methyloxy)phenyl]-5-(4-fluorophenyl)-2-thiophenesulfonamide (E296) | E74 | (4-Fluorophenyl)boronic acid | 476 |
| N-[5-(cis-3,5-Dimethyl-1-piperazinyl)-2-(methyloxy)phenyl]-2',4'-difluoro-4-biphenylsulfonamide (E297) | E106 | (2,4-Difluorophenyl)boronic acid | 488 |
| N-[5-(cis-3,5-Dimethyl-1-piperazinyl)-2-(methyloxy)phenyl]-3',4'-difluoro-4-biphenylsulfonamide (E298) | E106 | (3,4-Difluorophenyl)boronic acid | 488 |

Examples 299-305

Examples 299-305 (E299-E305) were prepared using methods similar to that described below from the appropriate aryl halide and boronic acid (or boronate ester) indicated in the table below:

To a mixture of the appropriate aryl halide (1 eq) and boronic acid (1.5-3 eq) (or boronate ester) in DME (0.04-0.07 M) was added a solution of potassium tert-butoxide (9 eq) and tetrakis(triphenylphosphine)palladium(0) (5-10 mol %) in water (0.22-0.33 M) and the resulting mixture heated at reflux (~110° C.) under argon for 2-4 hours. If appropriate, additional boronic acid and tetrakis(triphenylphosphine) palladium(0) were added. The crude reaction mixture was added directly to the SCX ion exchange cartridge (Varian bond-elute) eluting with methanol followed by ammonia (2M in methanol). The appropriate fractions were combined and reduced in vacuo and the residue purified by mass directed autoprep HPLC or chromatography on silica gel to afford the title compound which was characterized as either the free base or hydrochloride salt.

| Example | Aryl Halide | Boronic acid or boronate ester | MS [M + H]+ |
|---|---|---|---|
| N-[2-Chloro-5-(cis-3,5-dimethyl-1-piperazinyl)phenyl]-4-(2-furanyl)benzenesulfonamide (E299) | D35 | 2-Furanylboronic acid | 446/448 |
| N-[2-Chloro-5-(cis-3,5-dimethyl-1-piperazinyl)phenyl]-5-(2-fluorophenyl)-2-thiophenesulfonamide (E300) | D36 | (2-Fluorophenyl)boronic acid | 480/482 |
| N-[5-(cis-3,5-Dimethyl-1-piperazinyl)-2-(methyloxy)phenyl]-3-fluoro-4-(5-methyl-3-thienyl)benzenesulfonamide (E301) | E105 | 4,4,5,5-Tetramethyl-2-(5-methyl-3-thienyl)-1,3,2-dioxaborolane (D38) | 490 |
| N-[5-(cis-3,5-Dimethyl-1-piperazinyl)-2-(methyloxy)phenyl]-2-fluoro-4-(5-methyl-3-thienyl)benzenesulfonamide (E302) | E103 | 4,4,5,5-Tetramethyl-2-(5-methyl-3-thienyl)-1,3,2-dioxaborolane (D38) | 490 |
| N-[5-(cis-3,5-Dimethyl-1-piperazinyl)-2-(methyloxy)phenyl]-4-(5-methyl-3-thienyl)benzenesulfonamide (E303) | E106 | 4,4,5,5-Tetramethyl-2-(5-methyl-3-thienyl)-1,3,2-dioxaborolane (D38) | 472 |
| 2-Chloro-N-[5-(cis-3,5-dimethyl-1-piperazinyl)-2-(methyloxy)phenyl]-4-(5-methyl-3-thienyl)benzenesulfonamide (E304) | E104 | 4,4,5,5-Tetramethyl-2-(5-methyl-3-thienyl)-1,3,2-dioxaborolane (D38) | 506/508 |

| Example | Aryl Halide | Boronic acid or boronate ester | MS [M + H]+ |
|---|---|---|---|
| N-[5-(cis-3,5-Dimethyl-1-piperazinyl)-2-(methyloxy)phenyl]-7-(2-furanyl)-2,1,3-benzoxadiazole-4-sulfonamide (E305) | E93 | 2-Furanylboronic acid | 484 |

Example 306

2-Chloro-N-[5-(cis-3,5-dimethyl-1-piperazinyl)-2-(methyloxy)phenyl]-4-(5-methyl-2-furanyl)benzenesulfonamide (E306)

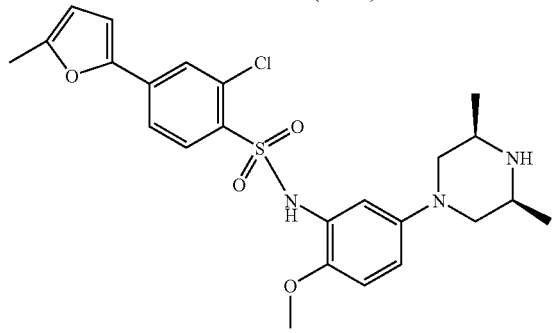

To a mixture of 4-bromo-2-chloro-N-[5-(cis-3,5-dimethyl-1-piperazinyl)-2-(methyloxy)phenyl]benzenesulfonamide (E104) (220 mg, 0.45 mmol), (5-methyl-2-furanyl) boronic acid (113 mg, 0.90 mmol) and tetrakis (triphenylphosphine)palladium(0) (58 mg, 0.05 mmol) in DME (3 ml) was added potassium tert-butoxide (454 mg, 4.10 mmol) in water (1 ml), and the reaction heated in the microwave (set at high absorbance) at 100° C. for 30 minutes. The reaction was poured on to the SCX column eluting first with methanol and then 2M ammonia in methanol. The basic fractions were combined and solvent evaporated in vacuo. The product was purified by mass directed autoprep HPLC, the relevant fractions collected and solvent evaporated in vacuo. The product was triturated in ether to give the title compound (E306). MS (ES+) m/e 490/492 [M+H]+.

The hydrochloride salt of the product was prepared by dissolving pure material in 1.5 ml dichloromethane and 0.5 ml methanol and treating with 0.7 ml of 1M HCl in ether.

Example 307

N-[5-(cis-3,5-Dimethyl-1-piperazinyl)-2-(methyloxy)phenyl]-3-fluoro-4-(2-furanyl)benzenesulfonamide (E307)

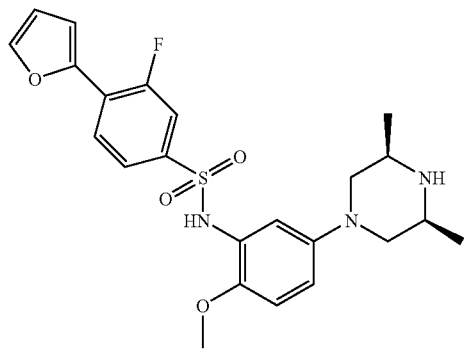

To a mixture of 4-bromo-N-[5-(cis-3,5-dimethyl-1-piperazinyl)-2-(methyloxy)phenyl]-3-fluorobenzenesulfonamide (E105) (150 mg, 0.32 mmol) and 2-furanylboronic acid (71 mg, 0.64 mmol) in DME (3 ml) was added potassium tert-butoxide (320 mg, 2.9 mmol) and tetrakis(triphenylphosphine)palladium(0) (20 mg, 0.017 mmol) in water (1 ml) and the resulting mixture stirred in a microwave (set at high absorbance) at 100° C. for 30 minutes. The reaction was checked by LC-MS and as starting material was still present (20%) more boronic acid (71 mg, 0.64 mmol) and tetrakis(triphenylphosphine)palladium(0) (20 mg, 0.017 mmol) were added. The mixture was stirred in the microwave (set at high absorbance) at 100° C. for another 30 minutes. The resulting mixture was then purified using an SCX cartridge and mass directed autoprep HPLC to afford the title compound (E307). MS (ES+) m/e 460 [M+H]+.

Example 308

2-Chloro-N-[5-(cis-3,5-dimethyl-1-piperazinyl)-2-(methyloxy)phenyl]-4-(2-furanyl)benzenesulfonamide (E308)

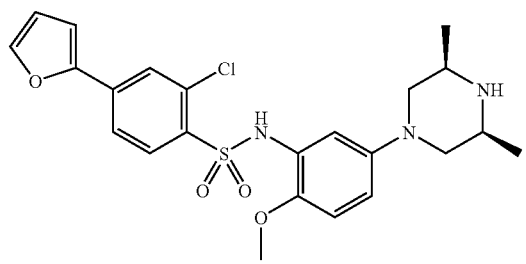

To a mixture of 4-bromo-2-chloro-N-[5-(cis-3,5-dimethyl-1-piperazinyl)-2-(methyloxy)phenyl]benzenesulfonamide (E104) (150 mg, 0.31 mmol) and 2-furanylboronic acid (69 mg, 0.62 mmol) in DME (3 ml) was added potassium tert-butoxide (312 mg, 2.8 mmol) and tetrakis (triphenylphosphine)palladium(0) (20 mg, 0.017 mmol) in water (1 ml) and the resulting mixture stirred in a microwave (set at high absorbance) at 100° C. for 30 minutes. The resulting mixture was then purified using an SCX cartridge followed by mass directed autoprep HPLC to afford the title compound (E308). MS (ES+) m/e 476/478 [M+H]+.

Example 309

N-[5-(cis-3,5-Dimethyl-1-piperazinyl)-2-(methyloxy)phenyl]-2-fluoro-4-(5-methyl-2-furanyl)benzenesulfonamide (E309)

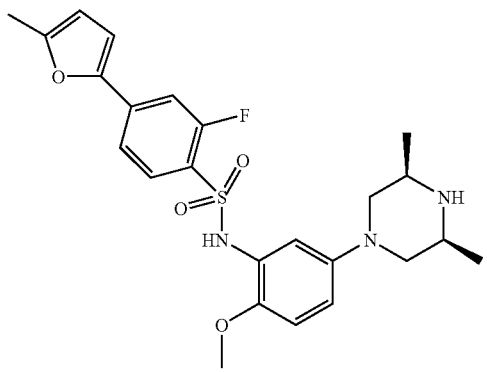

To a mixture of 4-bromo-N-[5-(cis-3,5-dimethyl-1-piperazinyl)-2-(methyloxy)phenyl]-2-fluorobenzenesulfonamide (E103) (200 mg, 0.42 mmol) and (5-methyl-2-furanyl)boronic acid (106 mg, 0.84 mmol) in DME (3 ml) was added potassium tert-butoxide (430 mg, 3.8 mmol) and tetrakis(triphenylphosphine)palladium(0) (20 mg, 0.017 mmol) in water (1 ml) and the resulting mixture stirred in a microwave (set at high absorbance) at 100° C. for 30 minutes. The solvent was evaporated in vacuo and residue purified using an SCX column followed by mass directed autoprep HPLC (with addition of 0.1 ml of 10% citric acid in water to the DMSO/MeCN sample to help dissolution) to afford the title compound (E309). MS (ES+) m/e 474 [M+H]$^+$.

The hydrochloride salt of the product was prepared by dissolving pure product in 1 ml dichloromethane, adding 1M HCl in ether (0.5 ml) and stirring at room temperature for 30 mins. The solvent was evaporated in vacuo and solid dried in a vacuum oven overnight.

Example 310

N-[3-(cis-3,5-Dimethyl-1-piperazinyl)-4-(ethyloxy)phenyl]-4-(2-thienyl)benzenesulfonamide (E310)

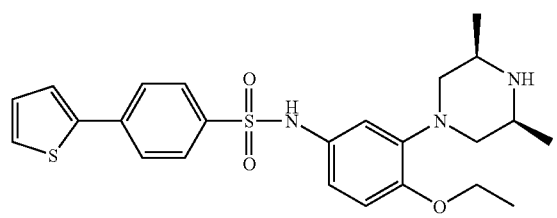

A mixture of N-[3-(cis-3,5-dimethyl-1-piperazinyl)-4-(ethyloxy)phenyl]-4-iodobenzenesulfonamide (E94) (206 mg, 0.4 mmol), 2-thienylboronic acid (103 mg, 0.8 mmol), 2M aqueous sodium carbonate solution (1 ml, 2 mmol) and bis(triphenylphosphine)palladium(II) chloride (14 mg, 0.02 mmol) in 1:1 toluene:ethanol (3 ml) was stirred in a microwave reactor (set at high absorbance) at 125° C. for 15 minutes. After cooling to room temperature the reaction mixture was acidified with 5N hydrochloric acid the mixture applied to an SCX ion exchange cartridge (Varian bond-elute) and washed with methanol and 2M ammonia in methanol. The combined basic fractions were concentrated in vacuo and the residue purified by chromatography on silica gel to afford the desired product (E310). MS (ES+) m/e 472 [M+H]$^+$.

Examples 311 and 312

Examples 311 and 312 (E311 and E312) were prepared from N-[5-bromo-2-(methyloxy)phenyl]-4-(2-thienyl)benzenesulfonamide (Product of E272 Step 2) and the appropriate amine as indicated in the Table below using similar methods to that described in for Example 277 (Step 3).

| Example | Amine | MS [M + H]$^+$ |
|---|---|---|
| N-{2-(Methyloxy)-5-[(3S)-3-methyl-1-piperazinyl]phenyl}-4-(2-thienyl)benzenesulfonamide (E311) | (2S)-2-Methylpiperazine | 444 |
| N-{2-(Methyloxy)-5-[(3R)-3-methyl-1-piperazinyl]phenyl}-4-(2-thienyl)benzenesulfonamide (E312) | (2R)-2-Methylpiperazine | 444 |

Example 313

N-[5-(cis-3,5-dimethyl-1-piperazinyl)-2-hydroxyphenyl]-4-(5-methyl-2-furanyl)benzenesulfonamide (E313)

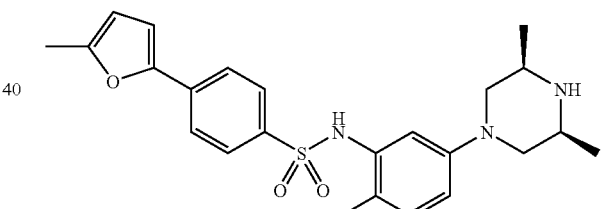

A solution of N-{5-(cis-3,5-dimethyl-1-piperazinyl)-2-[(phenylmethyl)oxy]phenyl}-4-(5-methyl-2-furanyl)benzenesulfonamide (D43) (100 mg, 0.19 mmol) in ethanol (4 ml) and N,N-dimethylformamide (2.5 ml) was treated with palladium hydroxide on carbon (25 mg) and the mixture stirred under an atmosphere of hydrogen for 3.75 h. The mixture was then filtered through celite, washing with ethanol and the filtrate reduced in vacuo and the residue purified by mass directed autoprep HPLC to afford the title compound. MS (ES+) m/e 442 [M+H]$^+$.

The hydrochloride salt of the product was prepared by dissolving the pure material in methanol and acidifying with ethereal HCl.

Examples 314-316

Examples 314-316 (E314-E316) were prepared from the appropriate benzyl ether listed in the table using similar methods to that described for Example 313 (E313):

| Example | Benzyl ether | MS [M + H]+ |
|---|---|---|
| N-[5-(cis-3,5-Dimethyl-1-piperazinyl)-2-hydroxyphenyl]-4-(2-furanyl)benzenesulfonamide (E314) | D44 | 428 |
| N-[5-(cis-3,5-Dimethyl-1-piperazinyl)-2-hydroxyphenyl]-3-fluoro-4-(5-methyl-2-furanyl)benzenesulfonamide (E315) | D45 | 460 |
| N-[5-(cis-3,5-Dimethyl-1-piperazinyl)-2-hydroxyphenyl]-5-(2-fluorophenyl)-2-thiophenesulfonamide (E316) | D46 | 462 |

Example 317

N-[15-(cis-3,5-dimethyl-1-piperazinyl)-2-(methyloxy)phenyl]-4-[(phenylmethyl)oxy]benzenesulfonamide (E317)

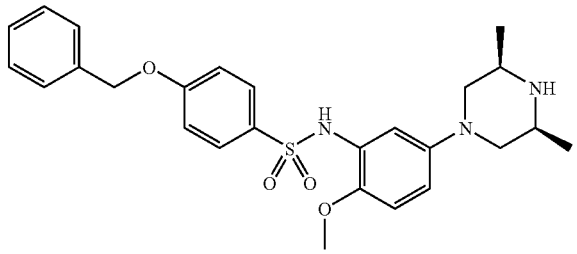

A mixture of methanesulfonic acid (4 mg, 0.043 mmol) and 2-tert-butylimino-2-diethylamino-1,3-dimethyl-perhydro-1,3,2-diazaphosphorine (BEMP) (12 mg, 0.043 mmol) was shaken and then treated with 5-(cis-3,5-dimethyl-1-piperazinyl)-2-(methyloxy)aniline (D4) (100 mg, 0.43 mmol) and pentafluorophenyl 4-[(phenylmethyl)oxy]benzenesulfonate (D49) (170 mg, 0.39 mmol) followed by DMSO (0.5 ml) and triethylamine (0.060 ml, 0.43 mmol). The mixture was then heated in a microwave at 140° C. for 30 min. The crude mixture was then applied to an SCX cartridge eluting with methanol then 2M ammonia in methanol to give a residue which was purified further by mass directed autoprep autoprep HPLC to afford the title compound. MS (ES+) m/e 482 [M+H]+.

ASSAY PROCEDURES

Cloning of the Ghrelin Receptor GHS-R

Human GHS-R was cloned from human hypothalamus cDNA and TOPO Ta cloned into pCR2.1. The sequence was confirmed and transferred into pCDN for expression analysis. The sequence was confirmed again and the plasmid was electroporated into CHO cells. The clones were screened by FLIPR (Fluorometric hanging Plate Reader).

Generation of the GHS-R Bacmam Virus and Viral Titre Determination Virus Generation The open reading frame of GHS-R was transferred from pCDN into pFastBacmam vector. This vector was used to generate recombinant baculoviruses in which the insect cell-specific polyhedrin promoter has been replaced with a mammalian cell-active promoter, in this case CMV. This was then used with the Bac to Bac expression system (Invitrogen). Briefly the vector was transformed into DH10 bac E.coli and the bacmid isolated from the transformed cells. The bacmid was then transfected into Sf9 insect cells grown in ExCell 420 (JRH) medium in 6-well dishes for the production of recombinant baculovirus particles.

The supernatant from these cells was harvested containing the recombinant GHS-R bacmam virus. This P0 viral stock was then used to infect 200 mls of $1\times10^{-6}$ cells/ml Sf9 cells in ExCell 420 medium to further amplify the virus and provide a P1 stock. This P1 viral stock was then used to amplify a P2 viral stock of 10×1 liter erlemeyer shake flasks again harvesting the supernatant from the cells. This was then used to transduce mammalian cells for assay.

The open reading frame of rat Gαo G-protein was cloned by PCR from rat brain cDNA into pCDNA3 vector. This was then transferred into the pFast Bacmam vector and recombinant baculovirus particles generated as above.

Viral Titre Determination

Viral titres were determined at all stages of the virus scale up with a plaque ELISA method using a gp64 envelope protein monoclonal antibody.

SF9 cells were plated out into a 96 well plate and a dilution range of virus was added to the cells for 1 hour. The virus was removed and a 1% methylcellulose and media mix was added to the cells and incubated for 48 hrs. The cells were then fixed in a formaldehyde and acetone mix for 8 minutes. The cells were then washed with a phosphate buffered saline solution (PBS) and normal goat serum added for 25 mins. This was then removed and a gp64 monoclonal antibody added for 25 mins. The wells were then washed with PBS and a goat anti-mouse/HRP conjugated antibody added for 25 mins. The wells were again washed with PBS and True Blue peroxidase substrate solution (Kirkegaard & Perry Laboratories) added and incubated for 60 mins. Individual wells were counted for blue foci and taking into account the dilution factor, the plaque forming units/ml of the virus was determined.

1. GHS-R GTPγS Functional Agonist Assay

Generation of Cells Transiently Expressing the Ghrelin Receptor GHS-R

HEK293T cells (HEK293 cells stably expressing the SV40 large T-antigen) were maintained in DMEM containing 10% (v/v) newborn calf serum and 2 mM glutamine. Cells were seeded in 60 mm culture dishes and grown to 60-80% confluency (18-24 hrs) prior to transfection with pCDNA3 containing the relevant DNA species using Lipofectamine reagent. For transfection, 3 µg of DNA was mixed with 10 µl of Lipofectamine in 0.2 mL of Opti-MEM (Life Technologies Inc.) and was incubated at room temperature for 30 min prior to the addition of 1.6 mL of Opti-MEM. For cotransfection experiments, 1.5 µg of each cDNA species was used. Cells were exposed to the Lipofectamine/DNA mixture for 5 hrs and 2 mL of 10% (v/v) newborn calf serum in DMEM was then added. Cells were harvested 48 hrs after transfection.

Generation of Cells Transiently Expressing the Ghrelin Receptor GHS-R and Rat Gαo G-protein.

HEK293F cells maintained in Freestyle media (Invitrogen) were co-transduced with both GHS-R and rat Gαo G-protein by adding 300 mls of GHS-R virus ($1\times10^8$ pfu/ml) and 30 mls of Gαo G-protein ($4\times10^8$ pfu/ml) to $3\times10^8$ HEKF cells in 1 liter of freestyle media. 24 hours post transduction 2 mM sodium butyrate was added to enhance expression. 24 hours post sodium butyrate addition. The cells were harvested by membrane preparation.

Membrane Preparation from Cultured Cells

All steps of the protocol are carried out at 4° C. and with pre-cooled reagents. The cell pellet was resuspended in 10 volumes of buffer A2 containing 50 mM N-2-hydroxyethylpiperazine-N'-2-ethanesulfonic acid (HEPES) (pH 7.40) supplemented with 10 e-4M leupeptin (acetyl-leucyl-leucyl-arginal; Sigma L2884), 25 µg/mL bacitracin (Sigma B0125), 1 mM ethylenediamine tetra-acetic acid (EDTA), 1 mM phenylmethylsulfonyl fluoride (PMSF) and 2×10 e-6M pepstain A (Sigma). The cells were then homogenized by 2×15 sec bursts in a 1 liter glass Waring blender, followed by centrifugation at 500 g for 20 mins. The supernatant was then spun at 48,000 g for 30 mins. The pellet was resuspended in 4 volumes of buffer A2 by vortexing for 5 secs, followed by homogenization in a Dounce homogenizer (10-15 strokes). At this point the preparation was aliquoted into polypropylene tubes and stored at −70° C.

Compounds of the invention were tested for in vitro biological activity in accordance with the following GTPγS assays:

GHS-R GTPγS Functional Agonist Assay Protocol (I)

For each compound being assayed, in an Opti clear bottom 96 well plate, is added:
(a) 20 µl of test compound (or 10 µl of guanosine 5'-triphosphate (GTP) (Sigma) as non-specific binding control) diluted to required concentration in assay buffer (20 mM N-2-Hydroxyethylpiperazine-N'-2-ethanesulfonic acid (HEPES)+100 mM NaCl+10 mM $MgCl_2$, pH adjusted to 7.4 with NaOH);
(b) 60 µl bead/membrane/GDP mix prepared by suspending wheat germ agglutinin-polyvinyltoluene (WGA-PVT) scintillation proximity assay (SPA) beads at 100 mg/mL in assay buffer followed by mixing with membrane (prepared in accordance with the methodology described above) and diluting in assay buffer to give a final volume of 60 µl which contains 10 µg protein and 0.5 mg bead per well—mixture was pre-mixed at 4° C. for 30 mins on a roller and just prior to addition to the plate, 10 µM final concentration of guanosine 5' diphosphate (GDP) (Sigma; diluted in assay buffer) was added;
(c) 10 µl guanosine 5' [γ35-S] thiotriphosphate, triethylamine salt (Amersham;
radioactivity concentration=37 kBq/µl or 1 mCi/ml; Specific Activity 1160 Ci/mmol) diluted to 3.8 nM in assay buffer to give 0.38 nM final.

The plate was then incubated on a shaker at room temperature for 30 mins followed by centrifugation for 5 mins at 1500 rpm. The plate was read between 3 and 6 hours after completion of centrifuge run in a Wallac Microbeta counter on a 1 min normalized tritium count protocol. Data was analyzed using a 4-parameter logistic equation. Basal activity used as minimum.

GHS-R GTPγS Functional Agonist Assay Protocol (II)

For each compound being assayed, in an Opti clear bottom 96 well plate, is added:
(a) 5 µl of test compound diluted to require concentration in 100% DMSO and added to 15 µl assay buffer (20 mM N-2-Hydroxyethylpiperazine-N'-2-ethanesulfonic acid (HEPES)+100 mM NaCl+10 mM $MgCl_2$, pH adjusted to 7.4 with NaOH);
(b) 20 µl guanosine 5' [γ35-S] thiotriphosphate, triethylamine salt (Amersham; radioactivity concentration=37 kBq/µl or 1 mCi/ml; Specific Activity 1160 Ci/mmol) diluted to 1.9 nM in assay buffer to give 0.38 nM final.
(c) Membrane (prepared in accordance with the methodology described above) were diluted in assay buffer to give a final concentration which contains 5 µg protein per well in 60 µl. 40 µM final concentration of guanosine 5' diphosphate (GDP) (Sigma; diluted in assay buffer) was added and left to incubate for 10 minutes before addition to the assay The assay is started by the mixing of components from a, b and c and allowed was to incubated at room temperature for 30 mins.
(d) Wheat germ agglutinin-polyvinyltoluene (WGA-PVT) scintillation proximity assay (SPA) beads were diluted in assay buffer to a concentration of 20 mgs/ml. 25 µl of bead was then added to the reaction mix and the assay was incubated for another 30 mins at room temperature with shaking. This was followed by centrifugation for 5 mins at 1500 rpm. The plate was read between 3 and 6 hours after completion of centrifuge run in a Wallac Microbeta counter on a 1 min normalized tritium count protocol. Data was analyzed using a 4-parameter logistic equation. Basal activity used as minimum.

Examples 1 to 317 all have an activity of <1 µM in the GHS-R GTPγS functional agonist assays.

2. GHSR Agonist BACMAM FLIPR Assay

Generation of HEK MSR II Cells Transiently Expressing the Ghrelin Receptor GHS-R 24 hours prior to assay HEK MSR II cells at confluence 80-95% are harvested and spun down. The supernatant is removed and the cells resuspended in media (Earls MEM+10% FBS+1% L-Glutamine). A cell count is performed using the Cedex instrumentation, and the concentration of cells is adjusted using media to give 280K cells per ml (14K cells/50 ul).

Human GHSR BACMAM virus is added to the cell suspension at an appropriate % volume (calculated for individual batches of BACMAM virus as viral titres vary). The transduced cell suspension is dispensed into FLIPR 384-well clear bottom plates, 50 ul per well. Cell plates are incubated at 37° C. overnight.

Generation of U2OS Cells Transiently Expressing the Ghrelin Receptor GHS-R 24 hours prior to assay U2OS cells at confluence 100% are harvested and spun down. The supernatant is removed and the cells resuspended in media (DMEM+10% FBS+1% L-Glutamine). A cell count is performed using the Cedex instrumentation, and the concentration of cells is adjusted using media to give 20K cells per ml (10K cells/50 ul).

Human GHSR BACMAM virus is added to the cell suspension at an appropriate % volume (calculated for individual batches of BACMAM virus as viral titres vary). The transduced cell suspension is dispensed into FLIPR 384-well clear bottom plates, 50 ul per well. Cell plates are incubated at 37° C. overnight.

Compound Preparation

Master compound plates are prepared in 100% DMSO. 3 mM is the top concentration (giving 10 µM final concentration) and they are serially diluted 1 in 4. 2 ul from the master plate is transferred to a daughter plate, to which is added 100 µl of compound dilution buffer (Tyrodes+1 mg/ml BSA+1.5 mM $CaCl_2$). This plate is used for the assay.

Compounds of the invention were tested for in vitro biological activity in accordance with the following FLIPR assay:

GHSR Agonist BACMAM FLIPR Assay Protocol

Media is aspirated from cell plates using a cell washer (leaving 10 ul of media). Cells are immediately loaded with loading buffer (Tyrodes (Elga water+145 mM NaCl+5 mM KCl+20 mM HEPES+10 mM glucose+1 mM $MgCl_2$)+1.5 mM $CaCl_2$+0.714 mg/ml Probenicid (predissolved in 1 M NaOH)+0.5 mM brilliant black+2.5 uM Fluo 4 dye, and incubated at 37.5° C. for 1 hour. 10 µl from compound plates is then added immediately to cell plates using a FLIPR 3 calcium imaging instrument. Fluorescence measurements are taken.

Examples 1 to 317 all have an $EC_{50}$ value a of <1 μM in the GHSR Agonist BACMAM FLIPR Assay.

What is claimed is:

1. A compound of formula (I):

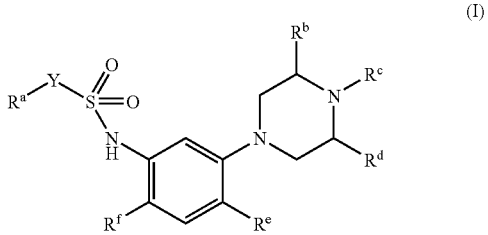

in which $R^a$ is aryl or heteroaryl;
Y is a single bond, $CH_2$, $CH_2CH_2$, or CH=CH;
$R^b$ is hydrogen or $C_{1-6}$alkyl;
$R^c$ is hydrogen or methyl;
$R^d$ is $C_{1-6}$alkyl;
$R^e$ is hydrogen, $C_{1-6}$alkyl, $C_{3-6}$cycloalkyl, $COC_{1-6}$alkyl, $C_{1-6}$alkoxy, halogen, hydroxyl, trifluoromethyl, trifluoromethoxy or cyano; and
$R^f$ is hydrogen, $C_{1-6}$alkyl, $C_{3-6}$cycloalkyl, $COC_{1-6}$alkyl, $C_{1-6}$alkoxy, $C_{1-6}$alkoxy, $C_{1-6}$alkyl, halogen, hydroxyl, trifluoromethyl, or cyano;
or a pharmaceutically acceptable salt thereof.

2. A compound of claim 1 having the formula (IA):

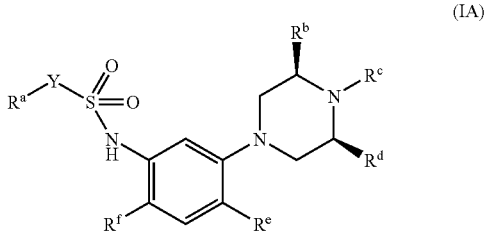

wherein $R^a$, $R^b$, $R^c$, $R^d$, $R^e$, $R^f$ and Y are as defined in claim 1.

3. A compound of claim 1 wherein:
$R^a$ is optionally substituted with one to three substituents selected from $C_{1-6}$alkyl, halogen, dimethylamino, trifluoromethyl, optionally substituted aryl or optionally substituted heteroaryl;
Y is a single bond or CH=CH;
$R^b$ is hydrogen or methyl;
$R^c$ is hydrogen;
$R^d$ is methyl;
$R^e$ is H, $C_{1-6}$ alkoxy, cyano, halogen or trifluoromethoxy; and
$R^f$ as H, $C_{1-6}$ alkoxy cyano, halogen, hydroxyl, $C_{1-6}$ alkoxy $C_{1-6}$ alkyl or $COC_{1-6}$alkyl.

4. A compound of claim 1 wherein:
$R^a$ is optionally substituted with one to two substituents selected from $C_{1-6}$alkyl, halogen, oxo, optionally substituted aryl or optionally substituted heteroaryl;
Y as a single bond or CH=CH;
$R^b$ is methyl;
$R^c$ is hydrogen or methyl;
$R^d$ is methyl;
$R^e$ is H or $C_{1-6}$ alkoxy; and
$R^f$ is H, $C_{1-6}$ alkoxy or $COC_{1-6}$alkyl.

5. A compound of claim 1 wherein:

$R^a$ is phenyl, thienyl, benzothiophene, naphthyl, quinolinyl, thienopyridyl, pyridyl, oxazolyl, benzoxazolyl, chromene or benzoxadiazolyl optionally substituted with one to three substituents selected from optionally substituted pyridyl, optionally substituted phenyloxy, chloro, methyl, dimethylamino, optionally substituted thienyl, optionally substituted pyrazolyl, iodo, optionally substituted pyrrolidinyl, optionally substituted isoxazolyl, fluoro, bromo, optionally substituted oxazolyl, optionally substituted phenyl, isopropyl, methoxy, optionally substituted furanyl, optionally substituted benzothiophenyl, optionally substituted thiazolyl, trifluoromethyl, optionally substituted pyrazolyl, optionally substituted pyrazinyl, optionally substituted pyrimidinyl and optionally substituted phenylethoxy;
Y is a single bond or CH=CH;
$R^b$ is hydrogen or methyl;
$R^c$ is hydrogen;
$R^d$ is ethyl;
$R^e$ is hydrogen, methoxy, cyano, fluoro, ethoxy or trifluoromethoxy; and
$R^f$ is hydrogen, methoxy, cyano, fluoro, ethoxy, isopropoxy, hydroxyl, chloro or acetyl.

6. A compound of claim 1 wherein:
$R^a$ is phenyl, thienyl, pyridinyl, naphthyl, quinolinyl, benzothiophenyl, or thienopyridinyl optionally substituted with one to two substituents selected from methyl, chloro, cyano, iodo, oxo, dimethylamino, optionally substituted phenoxy, optionally substituted phenyl, optionally substituted pyridinyl, optionally substituted thienyl, optionally substituted pyrozolyl or optionally substituted pyrrolidinyl;
Y is a single bond or CH=CH;
$R^b$ is methyl;
$R^c$ is hydrogen;
$R^d$ is methyl;
$R^e$ is H or methoxy; and
$R^f$ is H, methoxy or acetyl.

7. A compound of claim 1 wherein:
$R^a$ is phenyl, thienyl, or naphthyl optionally substituted with one to two substituents selected from chloro, optionally substituted thienyl, fluoro, optionally substituted phenyl and optionally substituted furanyl;
Y is a single bond;
$R^b$ is methyl;
$R^c$ is hydrogen;
$R^d$ is methyl;
$R^e$ is hydrogen; and
$R^f$ is methoxy.

8. A compound of claim 1 wherein:
$R^a$ is phenyl optionally substituted with one to two substituents selected from, fluoro and optionally substituted furanyl,
Y is a single bond;
$R^b$ is methyl;
$R^c$ is hydrogen;
$R^d$ is methyl;
$R^e$ is hydrogen; and
$R^f$ is methoxy.

9. A compound of claim 1 selected from:
N-[3-(cis-3,5-Dimethyl-1-piperazinyl)-4-(methyloxy) phenyl]-5-(2-pyridinyl)-2-thiophenesulfonamide
4-[(3-Chloro-2-cyanophenyl)oxy]-N-[3-(cis-3,5-dimethyl-1-piperazinyl)-4-(methyloxy)phenyl]benzenesulfonamide
5-Chloro-N-[3-(cis-3,5-dimethyl-1-piperazinyl)-4-(methyloxy)phenyl]-3-methyl-1-benzothiophene-2-sulfonamide
5-(Dimethylamino)-N-[3-(cis-3,5-dimethyl-1piperazinyl)-4-(methoxy)phenyl]-1-naphthalenesulfonamide N-[3-(cis-3,5-Dimethyl-1-piperazinyl)-4(methyloxy)phenyl]-1-naphthalenesulfonamide
(E)-N-[3-(cis-3,5-Dimethyl-1-piperazinyl)-4(methyloxy)phenyl]-2-phenylethenesulfonamide
5-Chloro-N-[3-(cis-3,5-dimethyl-1-piperazinyl)-4-(methyloxy)phenyl]-1-bezothiophene-2-sulfonamide
N-[3-(cis-3,5-Dimethyl-1-piperazinyl)-4-(methyloxy)phenyl]-4-(phenyloxy)benzenesulfonamide
N-[3-(cis-3,5-Dimethyl-1-piperazinyl)-4-(methyloxy)phenyl]-8-quinolinesulfonamide
N-[3-(cis-3,5-Dimethyl-1-piperazinyl)-4-(methyloxy)phenyl]thieno[2,3-b]pyridine-2-sulfonamide
N-[3-(cis-3,5-Dimethyl-1piperazinyl)-4-(methyloxy)phenyl]-4-(2-thienyl)benzenesulfonamide
8-Chloro-N-[3-[(cis-3,5-dimethyl-1-piperazinyl)-4-(methyloxy)phenyl]-1-naphthalenesulfonamide
N-[5-(cis-3,5-Dimethyl-1-piperazinyl)-2-(methyloxy)phenyl]-5-(2-pyridinyl)-2-thiophenesulfonamide
4-[(3-Chloro-2-cyanophenyl)oxy]-N-[5-(cis-3,5-dimethyl-1piperazinyl)-2-(methyloxy)phenyl]benzenesulfonamide
N-[5-(cis-3,5-Dimethyl-1piperazinyl)-2-(methyloxy)phenyl]-4-(1H-pyrazol-1-yl)benzenesulfonamide
5-Chloro-N-[5-(cis-3,5-dimethyl-1piperazinyl)-2-(methyloxy)phenyl)-3-methyl-1-benzothiophene-2-sulfonamide
N-[5-(cis-3,5-Dimethyl-1-piperazinyl)-2(methyloxy)phenyl]-4-(2-thienyl)benzenesulfonamide
N-[3-(cis-3,5-Dimethyl-1-piperazinyl)-4-(methyloxy)phenyl]-2-naphthalenesulfonamide
N-[3-(cis-3,5-Dimethyl-1-piperazinyl)-4-(methyloxy)phenyl]-4-(1H-pyrazol-1-yl)benzenesulfonamide
N-[3-(cis-3,5-Dimethyl-1-piperazinyl)-4-(methyloxy)phenyl]-6-(3-thienyl)-2-pyridinesulfonamide
N-[3-(cis-3,5-Dimethyl-1-piperazinyl)-4-(methyloxy)phenyl]-5-(6-methyl-2pyridinyl)-2-thiophenesulfonamide
N-[3-cis-3,5-Dimethyl-1-piperazinyl)-4-(methyloxy)phenyl]-4-iodobenzenesulfonamide
N-[3-(cis-3,5-Dimethyl-1-piperazinyl)-4-(methlloxy)phenyl]-4-(2-oxo-1-pyrrolidinyl)benzenesulfonamide
N-[2-Acetyl-5-(cis-3,5-dimethyl-1-piperazinyl)phenyl]-4-[(3-chloro-2-cyanophenyl)oxy]benzenesulfonamide
N-[2-Acetyl-5-(cis-3,5-dimethyl-1-piperazinyl)phenyl]-5-(2-pyridinyl)-2-thiophenesulfonamide
N-[2-Acetyl-5-(cis-3,5-dimethyl-1-piperazinyl)phenyl]-4-(2-thienyl)benzenesulfonamide
N-[2-Acetyl-5-(cis-3,5-dimethyl-1-piperazinyl)phenyl]-4-(1H-pyrazol-1-yl)benzenesulfonamide
N-[3-(cis-3,5-Dimethyl-1-piperazinyl)-4-(methyloxy)phenyl]-3,5-dimethyl-4-isoxazolesulfonamide
2,3-Dichloro-N-[3-(cis-3,5-dimethyl-1-piperazinyl)-4-(methyloxy)phenyl]benzenesulfonamide
3,4-Dichloro-N-[3-(cis-3,5-dimethyl-1-piperazinyl)-4-(methyloxy)phenyl]benzenesulfonamide
N-[5-(cis-3,5-Dimethyl-1-piperazinyl)-2-(methyloxy)phenyl]-2-naphthalenesulfonamide
N-[5-(cis-3,5-Dimethyl-1-piperazinyl)-2-(methyloxy)phenyl]-1-naphthalenesulfonamide
N-[5-(cis-3,5-Dimethyl-1-piperazinyl)-2-(methyloxy)phenyl]-4-(phenyloxy)benzenesulfonamide
N-[5-(cis-3,5-Dimethyl-1-piperazinyl)-2-(methyloxy)phenyl]-4-iodobenzenesulfonamide
N-[5-(cis-3,5-Dimethyl-1-piperazinyl)-2-(methyloxy)phenyl]-8-quinolinesulfonamide
3,4-Dichloro-N-[5-(cis-3,5-dimethyl-1-piperazinyl)-2-(methyloxy)phenyl]benzenesulfonamide
2,3-Dichloro-N-[5-(cis-3,5-dimethyl-1-piperazinyl)-2-(methyloxy)phenyl]benzenesulfonamide
(E)-N-[5-(cis-3,5-Dimethyl-1-piperazinyl)-2-(methyloxy)phenyl]-2-phenylethenesulfonamide
N-[4-Cyano-3-(cis-3,5-dimethyl-1-piperazinyl)phenyl]-4-(2-thienyl)benzenesulfonamide
N-[5-(cis-3,5-Dimethyl-1-piperazinyl)-2-(methyloxy)phenyl]-5-fluoro-3-methyl-1-benzothiophene-2-sulfonamide
5'-Chloro-N-[5-(cis-3,5-dimethyl-1-piperazinyl)-2-(methyloxy)phenyl]-2,2'-bithiophene-5-sulfonamide
2-Bromo-N-[5-(cis-3,5-dimethyl-1-piperazinyl)-2-(methyloxy)phenyl]benzenesulfonamide
N-[3-(cis-3,5-Dimethyl-1-piperazinyl)-4-(methyloxy)phenyl]-5-(1,3-oxazol-5-yl)-2-thiophenesulfonamide
N-[3-(cis-3,5-Dimethyl-1-piperazinyl)phenyl]-4-(2-thienyl)benzenesulfonamide
4-(5-Chloro-2-thienyl)-N-[3-(cis-3,5-dimethyl-1-piperazinyl)phenyl]benzenesulfonamide
N-[3-(cis-3,5-Dimethyl-1-piperazinyl)phenyl]-4-(1H-pyrazol-1-yl)benzenesulfonamide
5-Chloro-N-[3-(cis-3,5-dimethyl-1-piperazinyl)-4-(methyloxy)phenyl]-2-naphthalenesulfonamide
N-[3-(cis-3,5-Dimethyl-1-piperazinyl)-4-(methyloxy)phenyl]-4-biphenylsulfonamide
4-Bromo-N-[3-(cis-3,5-dimethyl-1-piperazinyl)-4-(methyloxy)phenyl]-3-methylbenzenesulfonamide
4-Bromo-N-[3-(cis-3,5-dimethyl-1-piperazinyl)-4-(methyloxy)phenyl]-3-fluorobenzenesulfonamide
4-Bromo-2-chloro-N-[3-(cis-3,5-dimethyl-1-piperazinyl)-4-(methyloxy)phenyl]benzenesulfonamide
4-Bromo-N-[3-(cis-3,5-dimethyl-1-piperazinyl)-4-(methyloxy)phenyl]-2-fluorobenzenesulfonamide
N-[5-(cis-3,5-Dimethyl-1-piperazinyl)-4-fluoro-2-(methyloxy)phenyl]-4-(2-thienyl)benzenesulfonamide
N-[5-(cis-3,5-Dimethyl-1-piperazinyl)-4-fluoro-2-(methyloxy)phenyl]-5-(2-pyridinyl)-2-thiophenesulfonamide
5-Chloro-N-[5-(cis-3,5-dimethyl-1-piperazinyl)-2-(methyloxy)phenyl]-1-benzothiophene-2-sulfonamide
N-[5-(cis-3,5-Dimethyl-1-piperazinyl)-2-(methyloxy)phenyl]-4-(1,3-oxazol-5-yl)benzenesulfonamide
N-[3-(cis-3,5-Dimethyl-1-piperazinyl)-4-(methyloxy)phenyl]-4-(1,3-oxazol-5-yl)benzenesulfonamide
N-[3-(cis-3,5-Dimethyl-1-piperazinyl)-4-(methyloxy)phenyl]-4-methyl-3,4-dihydro-2H-1,4-benzoxazine-7-sulfonamide
N-[3-(cis-3,5-Dimethyl-1-piperazinyl)-4-(methyloxy)phenyl]-4-(1-methylethyl)benzenesulfonamide
N-[5-(cis-3,5-Dimethyl-1-piperazinyl)-2-(methyloxy)phenyl]-3-{[4-(methyloxy)phenyl]oxy}benzenesulfonamide
N-[5-(cis-3,5-Dimethyl-1-piperazinyl)-2-(methyloxy)phenyl]-1-benzothiophene-3sulfonamide
N-[5-(cis-3,5-Dimethyl-1-piperazinyl)-2-(methyloxy)phenyl]-5-(1,3-oxazol-5-yl)-2-thiophenesulfonamide
N-[5-(cis-3,5-Dimethyl-1-piperazinyl)-2-(methyloxy)phenyl]-4-biphenylsulfonamide
N-[3-(cis-3,5-Dimethyl-1-piperazinyl)phenyl]-1-naphthalenesulfonamide
N-[3-(cis-3,5-Dimethyl-1-piperazinyl)phenyl]-2-naphthalenesulfonamide
2,3-Dichloro-N-[3-(cis-3,5-dimethyl-1-piperazinyl)phenyl]benzenesulfonamide
N-[3-(cis-3,5-Dimethyl-1-piperazinyl)phenyl]-1-benzothiophene-2-sulfonamide
N-[3-(cis-3,5-Dimethyl-1-piperazinyl)phenyl]-4-(1,3-oxazol-5-yl)benzenesulfonamide
N-[5-(cis-3,5-Dimethyl-1-piperazinyl)-2-methylphenyl]-2-naphthalenesulfonamide
N-[5-(cis-3,5-Dimethyl-1-piperazinyl)-2-methylphenyl]-1-naphthalenesulfonamide 8-Chloro-N-[5-(cis-3,5-dimethyl-1-piperazinyl)-2-(methyloxy)phenyl]-1-naphthalenesulfonamide
4-Bromo-N-[3-(cis-3,5-dimethyl-1-piperazinyl)-4(methyloxy)phenyl]-2-methylbenzenesulfonamide
4-Bromo-N-[5-(cis-3,5-dimethyl-1-piperazinyl-2-(methyloxy)phenyl]-3-methylbenzenesulfonamide
5-Bromo-N-[3-(cis-3,5-dimethyl-1-piperazinyl)-4-(methyloxy)phenyl]-2-thiophenesulfonamide
4-Chloro-N-[5-(cis-3,5-dimethyl-1-piperazinyl)-2-(methyloxy)phenyl]-1-naphthalenesulfonamide
3-Bromo-N-[5-(cis-3,5-dimethyl-1-piperazinyl)-2-(methyloxy)phenyl]benzenesulfonamide
5-Bromo-N-[5-(cis-3,5-dimethyl-1-piperazinyl)-2-(methyloxy)phenyl]-2-(methyloxy)benzenesulfonamide
5-Bromo-N-[5-(cis-3,5-dimethyl-1-piperazinyl)-2-(methyloxy)phenyl]-4-methyl-2-thiophenesulfonamide
N-[5-(cis-3,5-Dimethyl-1-piperazinyl)-2-(methyloxy)phenyl]-5-(1,2,3-thiadiazol-4-yl)-2-thiophenesulfonamide
N-[5-(cis-3,5-Dimethyl-1-piperazinyl)-2-(methyloxy)phenyl]-2,2-dimethyl-3,4-dihydro-2H-chromene-6-sulfonamide
4-Bromo-N-[5-(cis-3,5-dimethyl-1-piperazinyl)-2-methylphenyl]benzenesulfonamide
4-Bromo-N-[3-(cis-3,5-dimethyl-1-piperazinyl)-4-(methyloxy)phenyl]-2-(methyloxy)benzenesulfonamide
N-[5-(cis-3,5-Dimethyl-1-piperazinyl)-2-fluorophenyl]-5-(2-pyridinyl)-2-thiophenesulfonamide
N-[5-(cis-3,5-Dimethyl-1-piperazinyl)-2-fluorophenyl]-4-biphenylsulfonamide
N-[5-(cis-3,5-Dimethyl-1-piperazinyl)-2-fluorophenyl]-4-iodobenzenesulfonamide
4-Bromo-N-[5-(cis-3,5-dimethyl-1-piperazinyl)-2-fluorophenyl]-2-fluorobenzenesulfonamide
4-Bromo-2-chloro-N-[5-(cis-3,5-dimethyl-1-piperazinyl)-2-fluorophenyl]benzenesulfonamide
4-Bromo-N-[5-(cis-3,5-dimethyl-1-piperazinyl)-2-fluorophenyl]-2-methylbenzenesulfonamide
4-Bromo-N-[5-(cis-3,5-dimethyl-1-piperazinyl)-2-fluorophenyl]-3-fluorobenzenesulfonamide
N-[5-(cis-3,5-Dimethyl-1-piperazinyl)-2-fluoro-4-(methyloxy)phenyl]-4-iodobenzenesulfonamide
N-[5-(cis-3,5-Dimethyl-1-piperazinyl)-2-(ethyloxy)phenyl]-5-(2-pyridinyl)-2-thiophenesulfonamide
N-{5-(cis-3,5-Dimethyl-1-piperazinyl)-2[(methyloxy)methyl]phenyl}-4-biphenylsulfonamide
7-Chloro-N-[5-(cis-3,5-dimethyl-1-piperazinyl)-2-(methyloxy)phenyl]-2,1,3-benzoxadiazole-4-sulfonamide
N-[3-(cis-3,5-Dimethyl-1-piperazinyl)-4-(ethyloxy)phenyl]-4-iodobenzenesulfonamide
4-(5-Chloro-2-thienyl)-N-[5-(cis-3,5-dimethyl-1-piperazinyl)-2-(methyloxy)phenyl]benzenesulfonamide
4-(5-Chloro-2-thienyl)-N-[2-cyano-5-(cis-3,5-dimethyl-1-piperazinyl)phenyl]benzenesulfonamide
N-[2-Cyano-5-(cis-3,5-dimethyl-1-piperazinyl)phenyl]-4-(2-thienyl)benzenesulfonamide
4-(5-Chloro-2-thienyl)-N-[5-(cis-3,5-dimethyl-1-piperazinyl)-4-fluoro-2-(methyloxy)phenyl]benzenesulfonamide
N-[5-(cis-3,5-Dimethyl-1-piperazinyl)-2-(ethyloxy)phenyl]-4-iodobenzenesulfonamide
N-{5-(cis-3,5-Dimethyl-1-piperazinyl)-2-[(1-methylethyl)oxy]phenyl}-4-iodobenzenesulfonamide
4-Bromo-N-[3-(cis-3,5-dimethyl-1-piperazinyl)-4-(methyloxy)phenyl]benzenesulfonamide
4-Bromo-N-[5-(cis-3,5-dimethyl-1-piperazinyl)-2-(methyloxy)phenyl]-2-methylbenzenesulfonamide
4-Bromo-N-[5-(cis-3,5-dimethyl-1-piperazinyl)-2-(methyloxy)phenyl]-2-fluorobenzenesulfonamide
4-Bromo-2-chloro-N-[5-(cis-3,5-dimethyl-1-piperazinyl)-2-(methyloxy)phenyl]benzenesulfonamide
4-Bromo-N-[5-(cis-3,5-dimethyl-1-piperazinyl)-2-(methyloxy)phenyl]-3-fluorobenzenesulfonamide
4-Bromo-N-[5-(cis-3,5-dimethyl-1-piperazinyl)-2-(methyloxy)phenyl]benzenesulfonamide
N-[5-(cis-3,5-Dimethyl-1-piperazinyl)-2-(methyloxy)phenyl]-4-(4-methyl-2-thienyl)benzenesulfonamide
N-[5-(cis-3,5-Dimethyl-1-piperazinyl)-2-(methyloxy)phenyl]-2-methyl-4-(4-methyl-2-thienyl)benzenesulfonamide
N-[5-(cis-3,5-Dimethyl-1-piperazinyl)-2-(methyloxy)phenyl]-4-(2-furanyl)benzenesulfonamide
N-[5-(cis-3,5-Dimethyl-1-piperazinyl)-2-(methyloxy)phenyl]-2-fluoro-4-(4-methyl-2-thienyl)benzenesulfonamide
3'-Chloro-N-[5-(cis-3,5-dimethyl-1-piperazinyl)-2-(methyloxy)phenyl]-4-biphenylsulfonamide
N-[5-(cis-3,5-Dimethyl-1-piperazinyl)-2-(methyloxy)phenyl]-2-fluoro-4-(2-furanyl)benzenesulfonamide
2-Chloro-N-[5-(cis-3,5-dimethyl-1-piperazinyl)-2-(methyloxy)phenyl]-4-(4-methyl-2-thienyl)benzenesulfonamide
N-[5-(cis-3,5-Dimethyl-1-piperazinyl)-2-(methyloxy)phenyl]-3-fluoro-4-(2-thienyl)benzenesulfonamide
N-[5-(cis-3,5-Dimethyl-1-piperazinyl)-2-(methyloxy)phenyl]-3-fluoro-4-(4-methyl-2-thienyl)benzenesulfonamide
N-[5-(cis-3,5-Dimethyl-1-piperazinyl)-2-(methyloxy)phenyl]-3-fluoro-4-(3-furanyl)benzenesulfonamide
N-[5-(cis-3,5-Dimethyl-1-piperazinyl)-2-(methyloxy)phenyl]-3'-[(methyloxy)methyl]-4-biphenylsulfonamide
N-[5-(cis-3,5-Dimethyl-1-piperazinyl)-2-(methyloxy)phenyl]-4-(3-furanyl)benzenesulfonamide
N-[5-(cis-3,5-Dimethyl-1-piperazinyl)-2-(methyloxy)phenyl]-4-(3-thienyl)benzenesulfonamide
N-[5-(cis-3,5-Dimethyl-1-piperazinyl)-2-hydroxyphenyl]-5-(2-pyridinyl)-2-thiophenesulfonamide
N-[5-(cis-3,5-Dimethyl-1-piperazinyl)-2-(methyloxy)phenyl]-4-(2-oxo-1-pyrrolidinyl)benzenesulfonamide
5-Bromo-N-[5-(cis-3,5-dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5-{3-[(methyloxy)methyl]phenyl}-2-thiophenesulfonamide
N-[5-(cis-3,5-Dimethyl-1-piperazinyl)-2-(methyloxy)phenyl]-5-(2-fluorophenyl)-2-thiophenesulfonamide
5-Chloro-N-[5-(cis-3,5-dimethyl-1-piperazinyl)-2-(methyloxy)phenyl]-2-naphthalenesulfonamide
N-[5-(cis-3,5-Dimethyl-1-piperazinyl)-2-(methyloxy)phenyl]-4-(6-methyl-2-pyridinyl)benzenesulfonamide
N-[5-(cis-3,5-Dimethyl-1-piperazinyl)-2-(methyloxy)phenyl]-5-(6-methyl-2-pyridinyl)-2-thiophenesulfonamide
N-[3-(cis-3,5-Dimethyl-1-piperazinyl)-4-(methyloxy)phenyl]-4-(6-methyl-2-pyridinyl)benzenesulfonamide
N-[5-(cis-3,5-Dimethyl-1-piperazinyl)-2-(methyloxy)phenyl]-4-(3-pyridinyl)benzenesulfonamide
N-[5-(cis-3,5-Dimethyl-1-piperazinyl)-2-(methyloxy)phenyl]-2,2'-bithiophene-5-sulfonamide
N-[5-(cis-3,5-Dimethyl-1-piperazinyl)-2-(methyloxy)phenyl]-3-(2-thienyl)benzenesulfonamide
N-[3-(cis-3,5-Dimethyl-1-piperazinyl)-4-(methyloxy)phenyl]-4-(3-thienyl)benzenesulfonamide
4-(1-Benzothien-3-yl)-N-[5-(cis-3,5-dimethyl-1-piperazinyl)-2-(methyloxy)phenyl]benzenesulfonamide
N-[3-(cis-3,5-Dimethyl-1-piperazinyl)-4-(methyloxy)phenyl]-2,3'-bithiophene-5-sulfonamide N-[3-(cis-3,5-Dimethyl-1-piperazinyl)-4-(methyloxy)phenyl]-5-phenyl-2-thiophenesulfonamide 5-(1-Benzothien-3-yl)-N-[5-(cis-3,5-dimethyl-1-piperazinyl)-2-(methyloxy)phenyl]-2-thiophenesulfonamide N-[5-(cis-3,5-Dimethyl-1-piperazinyl)-2-(methyloxy)phenyl]-5-[4-(methyloxy)-3-pyridinyl]-2-thiophenesulfonamide N-[3-(cis-3,5-Dimethyl-1-piperazinyl)-4-(methyloxy)phenyl]-2,2'-bithiophene-5-sulfonamide N-[5-(cis-3,5-Dimethyl-1-piperazinyl)-2-(methyloxy)phenyl]-2'-(ethyloxy)-4-biphenylsulfonamide N-[3-(cis-3,5-Dimethyl-1-piperazinyl)-4-(methyloxy)phenyl]-4'-fluoro-2'-methyl-4-biphenylsulfonamide N-[3-(cis-3,5-Dimethyl-1-piperazinyl)-4-(methyloxy)phenyl]-2'-fluoro-4-biphenylsulfonamide N-[5-(cis-3,5-Dimethyl-1-piperazinyl)-2-(methyloxy)phenyl]-2,3'-bithiophene-5-sulfonamide N-[3-(cis-3,5-Dimethyl-1-piperazinyl)-4-(methyloxy)phenyl]-2-methyl-4-(2-thienyl)benzenesulfonamide N-[3-(cis-3,5-Dimethyl-1-piperazinyl)-4-(methyloxy)phenyl]-2-methyl-4-(6-methyl-2-pyridinyl)benzenesulfonamide 3'-Chloro-N-[3-(cis-3,5-dimethyl-1-piperazinyl)-4-(methyloxy)phenyl]-4'-fluoro-4-biphenylsulfonamide N-[3-(cis-3,5-Dimethyl-1-piperazinyl)-4-(methyloxy)phenyl]-3',5'-difluoro-4-biphenylsulfonamide N-[3-(cis-3,5-Dimethyl-1-piperazinyl)-4-(methyloxy)phenyl]-3'-fluoro-4-biphenylsulfonamide N-[3-(cis-3,5-Dimethyl-1-piperazinyl)-4-(methyloxy)phenyl]-3',4'-difluoro-4-biphenylsulfonamide N-[3-(cis-3,5-Dimethyl-1-piperazinyl)-4-(methyloxy)phenyl]-2',6'-dimethyl-4-biphenylsulfonamide N-[3-(cis-3,5-Dimethyl-1-piperazinyl)-4-(methyloxy)phenyl]-4'-fluoro-4-biphenylsulfonamide N-[3-(cis-3,5-Dimethyl-1-piperazinyl)-4-(methyloxy)phenyl]-4'-methyl-4-biphenylsulfonamide N-[3-(cis-3,5-Dimethyl-1-piperazinyl)-4-(methyloxy)phenyl]-2',3'-difluoro-4-biphenylsulfonamide N-[3-(cis-3,5-Dimethyl-1-piperazinyl)-4-(methyloxy)phenyl]-3'-methyl-4-biphenylsulfonamide 2'-Chloro-N-[5-(cis-3,5-dimethyl-1-piperazinyl)-2-(methyloxy)phenyl]-4-biphenylsulfonamide N-[5-(cis-3,5-Dimethyl-1-piperazinyl)-2-(methyloxy)phenyl]-2-methyl-4-(2-thienyl)benzenesulfonamide N-[3-(cis-3,5-Dimethyl-1-piperazinyl)-4-(methyloxy)phenyl]-3'-[(methyloxy)methyl]-4-biphenylsulfonamide N-[5-(cis-3,5-Dimethyl-1-piperazinyl)-2-(methyloxy)phenyl]-2-fluoro-4-(2-thienyl)benzenesulfonamide N-[3-(cis-3,5-Dimethyl-1-piperazinyl)-4-(methyloxy)phenyl]-2-methyl-4-(4-methyl-2-thienyl)benzenesulfonamide N-[5-(cis-3,5-Dimethyl-1-piperazinyl)-2-(methyloxy)phenyl]-4-(5-methyl-2-thienyl)benzenesulfonamide N-[3-(cis-3,5-Dimethyl-1-piperazinyl)-4-(methyloxy)phenyl]-3-fluoro-4-(2-thienyl)benzenesulfonamide 2-Chloro-N-[3-(cis-3,5-Dimethyl-1-piperazinyl)-4-(methyloxy)phenyl]-4-(4-methyl-2-thienyl)benzenesulfonamide N-[5-(cis-3,5-Dimethyl-1-piperazinyl)-2-(methyloxy)phenyl]-4-(4-methyl-3-thienyl)benzenesulfonamide N-[5-(cis-3,5-Dimethyl-1-piperazinyl)-2-(methyloxy)phenyl]-4-(3-furanyl)-2-methylbenzenesulfonamide N-[3-(cis-3,5-Dimethyl-1-piperazinyl)-4-(methyloxy)phenyl]-4-(3-furanyl)-2-methylbenzenesulfonamide N-[5-(cis-3,5-Dimethyl-1-piperazinyl)-2-(methyloxy)phenyl]-2-fluoro-4-(3-furanyl)benzenesulfonamide N-[5-(cis-3,5-Dimethyl-1-piperazinyl)-2-(methyloxy)phenyl]-2-fluoro-4-(6-methyl-2-pyridinyl)benzenesulfonamide 2-Chloro-N-[5(cis-3,5-dimethyl-1-piperazinyl)-2-(methyloxy)phenyl]-4-(6-methyl-2-pyridinyl)benzenesulfonamide N-[5-(cis-3,5-Dimethyl-1-piperazinyl)-2-(methyloxy)phenyl]-2-fluoro-4-(3-thienyl)benzenesulfonamide N-[3-(cis-3,5-Dimethyl-1-piperazinyl)-4-(methyloxy)phenyl]-3-methyl-4-(2-thienyl)benzenesulfonamide N-[3-(cis-3,5-Dimethyl-1-piperazinyl)-4-(methyloxy)phenyl]-2-fluoro-4-(2-thienyl)benzenesulfonamide N-[3-(cis-3,5-Dimethyl-1-piperazinyl)-4-(methyloxy)phenyl]-2-fluoro-4-(6-methyl-2-pyridinyl)benzenesulfonamide 2-Chloro-N-[3-(cis-3,5-Dimethyl-1-piperazinyl)-4-(methyloxy)phenyl]-4-(6-methyl-2-pyridinyl)benzenesulfonamide N-[5-(cis-3,5-Dimethyl-1-piperazinyl)-2-(methylphenyl]-4-(2-thienyl)benzenesulfonamide N-[5-(cis-3,5-Dimethyl-1-piperazinyl)-2-(methylphenyl]-4-(4-methyl-2-thienyl)benzenesulfonamide N-[5-(cis-3,5-Dimethyl-1-piperazinyl)-2-(methyloxy)phenyl]-3-methyl-4-(2-thienyl)benzenesulfonamide N-[5-(cis-3,5-Dimethyl-1-piperazinyl)-2-(methyloxy)phenyl]-3-methyl-4-(4-methyl-2-thienyl)benzenesulfonamide N-[3-(cis-3,5-Dimethyl-1-piperazinyl)-4-(methyloxy)phenyl]-4-(4-methyl-2-thienyl)benzenesulfonamide N-[5-(cis-3,5-Dimethyl-1-piperazinyl)-2-(methyloxy)phenyl]-2-methyl-4-(6-methyl-2-pyridinyl)benzenesulfonamide N-[5-(cis-3,5-Dimethyl-1-piperazinyl)-2-(methyloxy)phenyl]-3-methyl-4-(3-thienyl)benzenesulfonamide N-[5-(cis-3,5-Dimethyl-1-piperazinyl)-2-(methyloxy)phenyl]-4-(2-furanyl)-2-methylbenzenesulfonamide N-[5-(cis-3,5-Dimethyl-1-piperazinyl)-2-(methyloxy)phenyl]-2-(methyloxy)-5-(4-methyl-2-thienyl)benzenesulfonamide 2-Chloro-N-[5-(cis-3,5-Dimethyl-1-piperazinyl)-2-(methyloxy)phenyl]-4-(2-thienyl)benzenesulfonamide 2-Chloro-N-[5-(cis-3,5-dimethyl-1-piperazinyl)-2-(methyloxy)phenyl]-4-(3-furanyl)benzenesulfonamide N-[5-(cis-3,5-Dimethyl-1-piperazinyl)-2-(methyloxy)phenyl]-4-(3-furanyl)-3-methylbenzenesulfonamide N-[3-(cis-3,5-Dimethyl-1-piperazinyl)-4-(methyloxy)phenyl]-4-(3-furanyl)benzenesulfonamide N-[5-(cis-3,5-Dimethyl-1-piperazinyl)-2-(methyloxy)phenyl]-2'-fluoro-4-biphenylsulfonamide 3'-Chloro-N-[5-(cis-3,5-dimethyl-1-piperazinyl)-2-(methyloxy)phenyl]-4'-fluoro-4-biphenylsulfonamide N-[5-(cis-3,5-Dimethyl-1-piperazinyl)-2-(methyloxy)phenyl]-2',3'-difluoro-4-biphenylsulfonamide 5'-Chloro-N-[5-(cis-3,5-dimethyl-1-piperazinyl)-2-(methyloxy)phenyl]-2'-(methyloxy)-4-biphenylsulfonamide N-[5-(cis-3,5-Dimethyl-1-piperazinyl)-2-(methyloxy)phenyl]-3'-methyl-4-biphenylsulfonamide N-[5-(cis-3,5-Dimethyl-1-piperazinyl)-2-(methyloxy)phenyl]-3-fluoro-4-(6-methyl-2-pyridinyl)benzenesulfonamide N-[5-(cis-3,5-Dimethyl-1-piperazinyl)-2-(methyloxy)phenyl]-5-(2-fluorophenyl)-4-methyl-2-thiophenesulfonamide N-[5-(cis-3,5-Dimethyl-1-piperazinyl)-2-(methyloxy)phenyl]-4-methyl-5-(6-methyl-2-pyridinyl)-2-thiophenesulfonamide N-[5-(cis-3,5-Dimethyl-1-piperazinyl)-2-(methyloxy)phenyl]-4-methyl-5-{3-[(methyloxy)methyl]phenyl}-2-thiophenesulfonamide N-[5-(cis-3,5-Dimethyl-1-piperazinyl)-2-(ethyloxy)phenyl]-4-(2-thienyl)benzenesulfonamide N-{5-(cis-3,5-Dimethyl-1-piperazinyl)-2[(1-methylethyl)oxy]phenyl}-4-(2-thienyl)benzenesulfonamide
N-[5-(cis-3,5-Dimethyl-1-piperazinyl)-2-(methyloxy)phenyl]-5-phenyl-2-thiophenesulfonamide
5-(2,4-Difluorophenyl)-N-[5-(cis-3,5-dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5-[2-(ethyloxy)phenyl]-2-thiophenesulfonamide
N-[5-(cis-3,5-Dimethyl-1-piperazinyl)-2-(methyloxy)phenyl]-4'-methyl-2,2'-bithiophene-5-sulfonamide
5-(3-Chloro-4-fluorophenyl)-N-[5-(cis-3,5-dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5-(2-methylphenyl)-2-thiophenesulfonamide
5-(2,6-Dimethylphenyl)-N-[5-(cis-3,5-dimethyl-1-piperazinyl)-2-(methyloxy)phenyl]-2-thiophenesulfonamide
5-[5-Chloro-2-(methyloxy)phenyl]-N-[5-(cis-3,5-Dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5-(3-methylphenyl)-2-thiophenesulfonamide
N-[5-(cis-3,5-Dimethyl-1-piperazinyl)-2-(methyloxy)phenyl]-5-(4-fluorophenyl)-2-thiophenesulfonamide
N-[5-(cis-3,5-Dimethyl-1-piperazinyl)-2-(methyloxy)phenyl]-5-(4-fluoro-2-methylphenyl)-2-thiophenesulfonamide
5-(2-Chlorophenyl)-N-[5-(cis-3,5-dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5-(3-fluorophenyl)-2-thiophenesulfonamide
N-[5-(cis-3,5-Dimethyl-1-piperazinyl)-2-(methyloxy)phenyl]-5-(4-methylphenyl)-2-thiophenesulfonamide
5-(3-Chlorophenyl)-N-[5-(cis-3,5-Dimethyl-1-piperazinyl)-2-(methyloxy)phenyl]-2-thiophenesulfonamide
5-(2,4-Difluorophenyl)-N-[3-(cis-3,5-Dimethyl-1-piperazinyl)-4-(methyloxy)phenyl]-2-thiophenesulfonamide
N-[3-(cis-3,5-Dimethyl-1-piperazinyl)-4-(methyloxy)phenyl]-5-[2-(ethyloxy)phenyl]-2-thiophenesulfonamide
N-[3-(cis-3,5-Dimethyl-1-piperazinyl)-4-(methyloxy)phenyl]-4'-methyl-2,2'-bithiophene-5-sulfonamide
N-[3-(cis-3,5-Dimethyl-1-piperazinyl)-4-(methyloxy)phenyl]-5-{3-[(methyloxy)methyl]phenyl}-2-thiophenesulfonamide
5-(3-Chloro-4-fluorophenyl)-N-[3-(cis-3,5-dimethyl-1-piperazinyl)-4-(methyloxy)pheny;]-2-thiophenesulfonamide
N-[3-(cis-3,5-Dimethyl-1-piperazinyl)-4-methloxy)phenyl]-5-(2-methylphenyl)-2-thiophenesulfonamide
5-(2,6-Dimethylphenyl)-N-[3-(cis-3,5-dimethyl-1-piperazinyl)-4-(methyloxy)phenyl]-2-thiophenesulfonamide
5-[5-Chloro-2-(methyloxy)phenyl]-N-[3-(cis-3,5-dimethyl-1-piperazinyl)-4-(methyloxy)phenyl]-2-thiophenesulfonamide
5-(3,5-Difurophenyl)-N-[3-(cis-3,5-dimethyl-1-piperzinyl)-4-(methyloxy)phenyl]-2-thiophenesulfonamide
5-(4-Chlorophenyl)-N-[3-(cis-3,5-dimethyl-1-piperzinyl)-4-(methyloxy)phenyl]-2-thiophenesulfonamide
N-[3-(cis-3,5-Dimethyl-1-piperazinyl)-4-(methyloxy)phenyl]-5-(2-fluorophenyl)-2-thiophenesulfonamide
N-[3-(cis-3,5-Dimethyl-1-piperazinyl)-4-(methyloxy)phenyl]-5-(3-fluorophenyl)-2-thiophenesulfonamide
5-(2,3-Difurophenyl)-N-[3-(cis-3,5-dimethyl-1-piperzinyl)-4-(methyloxy)phenyl]-2-thiophenesulfonamide
5-(2-Chlorophenyl)-N-[3-(cis-3,5-dimethyl-1-piperzinyl)-4-(methyloxy)phenyl]-2-thiophenesulfonamide
N-[3-(cis-3,5-Dimethyl-1-piperazinyl)-4-(methyloxy)phenyl]-5-(3-fluorophenyl)-2-thiophenesulfonamide
5-(3-Chlorophenyl)-N-[3-(cis-3,5-dimethyl-1-piperzinyl)-4-(methyloxy)phenyl]-2-thiophenesulfonamide
N-[5-(cis-3,5-Dimethyl-1-piperazinyl)-2-fluorophenyl]-4-(2thienyl)benzensulfonamide
N-[5-(cis-3,5-Dimethyl-1-piperazinyl)-2-fluorophenyl]-4-(3furanyl)benzensulfonamide
N-[5-(cis-3,5-Dimethyl-1-piperazinyl)-2-fluorophenyl]-2-fluoro-4-(2thienyl)benzensulfonamide
2-Chloro-N-[5-(cis-3,5-dimethyl-1-piperazinyl)-2-fluorophenyl]-4-(2-thienyl)benzenesulfonamide
2-Chloro-N-[5-(cis-3,5-dimethyl-1-piperazinyl)-2-fluorophenyl]-4-(3-furanyl)benzenesulfonamide
N-[5-(cis-3,5-Dimethyl-1-piperazinyl)-2-fluorophenyl]-2-methyl-4-(2-thienyl)benzenesulfonamide
N-[5-(cis-3,5-Dimethyl-1-piperazinyl)-2-fluorophenyl]-4-(3-furanyl)-2-methylbenzenesulfonamide
N-[5-(cis-3,5-Dimethyl-1-piperazinyl)-2-fluorophenyl]-3-fluoro-4-(2-thienyl)benzenesulfonamide
N-[5-(cis-3,5-Dimethyl-1-piperazinyl)-2-fluorophenyl]-3-fluoro-4-(3-furanyl)benzenesulfonamide
N-[3-(cis-3,5-Dimethyl-1-piperazinyl)-4-(methyloxy)phenyl]-2-(methyloxy)-4-(2-thienyl)benzenesulfonamide
N-[5-(cis-3,5-Dimethyl-1-piperazinyl)-2-fluoro-4-(methyloxy)phenyl]-4-(2-thienyl)benzenesulfonamide
N-[5-(cis-3,5-Dimethyl-1-piperazinyl)-2-(methyloxy)phenyl]-5-(3-furanyl)-2-thiophenesulfonamide
5-(2,3-Difluorophenyl)-N-[5-(cis-3,5-dimethyl-1-piperazinyl)-2-(methyloxy)phenyl]-2-thiophenesulfonamide
N-[5-(cis-3,5-Dimethyl-1-piperazinyl)-2-(methyloxy)phenyl]-5'-methyl-2,2'-bithiophene-5-sulfonamide
N-[5-(cis-3,5-Dimethyl-1-piperazinyl)-4-(methyloxy)phenyl]-5-(3-furanyl)-2-thiophenesulfonamide
N-[5-(cis-3,5-Dimethyl-1-piperazinyl)-4-(methyloxy)phenyl]-5'-methyl-2,2'-bithiophene-5-sulfonamide
N-[5-(cis-3,5-Dimethyl-1-piperazinyl)-2,4-bis(methyloxy)phenyl]-4-(2-thienyl)benzenesulfonamide
N-{3-(cis-3,5-Dimethyl-1-piperazinyl)-4-[(trifluoromethyl)oxy]phenyl}-4-(2-thienyl)benzenesulfonamide
N-{5-(cis-3,5-Dimethyl-1-piperazinyl)-4-[(trifluoromethyl)oxy]phenyl}-5-(2-pyridinyl)-2-thiophenesulfonamide
N-[5-(cis-3,5-Dimethyl-1-piperazinyl)-2-(methyloxy)phenyl]-4-(5-methyl-2-furanyl)benzenesulfonamide
N-[5-(cis-3,5-Dimethyl-1-piperazinyl)-2-(methyloxy)phenyl]-3-fluoro-4-(5-methyl-2-furanyl)benzenesulfonamide
N-[5-(cis-3,5-Dimethyl-1-piperazinyl)-2-(methyloxy)phenyl]-5-(2-methyl-1,3-thiazol-4-yl)-2-thiophenesulfonamide
N-[5-(cis-3,5-Dimethyl-1-piperazinyl)-2-(methyloxy)phenyl]-4-methyl-3,4-dihydro-2H-1,4-benzoxazine-7-sulfonamide
4-Bromo-N-[cis-3,5-dimethyl-1-piperazinyl)phenyl]-2-(methyloxy)benzenesulfonamide
N-[2-Chloro-5-(cis-3,5-dimethyl-1-piperazinyl)phenyl]-5-(2-pyridinyl)-2-thiophenesulfonamide
4-Bromo-N-[5-(cis-3,5-dimethyl-1-piperazinyl)-2-(methyloxy)phenyl]-1-naphthalenesulfonamide
5-(5-Chloro-1,2,4-thiadiazol-3-yl)-N-[5-(cis-3,5-dimethyl-1-piperazinyl)-2-(methyloxy)phenyl]-2-thiophenesulfonamide
2-Bromo-N-[5-(cis-3,5-dimethyl-1-piperazinyl)-2-(methyloxy)phenyl]-4-(trifluoromethyl)benzenesulfonamide
4-Bromo-2,6-dichloro-N-[5-(cis-3,5-dimethyl-1-piperazinyl)-2-(methyloxy)phenyl]benzenesulfonamide
2,6-Dichloro-N-[5-(cis-3,5-dimethyl-1-piperazinyl)-2-(methyloxy)phenyl]benzenesulfonamide 2,4-Dibromo-N-[5-(cis-3,5-dimethyl-1-piperazinyl)-2-(methyloxy)phenyl]benzenesulfonamide
2,4-Dichloro-N-[5-(cis-3,5-dimethyl-1-piperazinyl)-2-(methyloxy)phenyl]-5-methylbenzenesulfonamide
4-Bromo-N-[5-(cis-3,5-dimethyl-1-piperazinyl)-2-fluorophenyl]-2-(methyloxy)benzenesulfonamide
4-Bromo-N-[5-(cis-3,5-dimethyl-1-piperazinyl)-2-fluorophenyl]-3-methylbenzenesulfonamide
N-[5-(cis-3,5-Dimethyl-1-piperazinyl)-2-fluorophenyl]-2-(methyloxy)-4-(2-thienyl)benzenesulfonamide
N-[5-(cis3,5-Dimethyl-1-piperazinyl)-2-fluorophenyl]-4-(3-furanyl)-2-(methyloxy)benzenesulfonamide
N-[5-(cis-3,5-Dimethyl-1-piperazinyl)-2-fluorophenyl]-2-(methyloxy)-4-(4-methyl-2-thienyl)benzenesulfonamide
N-[5-(cis-3,5-Dimethyl-1-piperazinyl)-2-fluorophenyl]-4-(4-methyl-2-thienyl)benzenesulfonamide
N-[5-(cis-3,5-Dimethyl-1-piperazinyl)-2-fluorophenyl]-2-methyl-4-(4-methyl-2-thienyl)benzenesulfonamide
N-[5-(cis-3,5-Dimethyl-1-piperazinyl)-2-fluorophenyl]-3-methyl-4-(4-methyl-2-thienyl)benzenesulfonamide
N-[5-(cis-3,5-Dimethyl-1-piperazinyl)-2-(methyloxy)phenyl]-4-(1,3-thiazol-2-yl)benzenesulfonamide
N-[5-(cis-3,5-Dimethyl-1-piperazinyl)-2-(methyloxy)phenyl]-4-(1-methyl-1H-pyrrol-2-yl)benzenesulfonamide
N-[5-(cis-3,5-Dimethyl-1-piperazinyl)-2-(methyloxy)phenyl]-4-(2-pyrazinyl)benzenesulfonamide
N-[5-(cis-3,5-Dimethyl-1-piperazinyl)-2-(methyloxy)phenyl]-4-(2-pyrimidinyl)benzenesulfonamide
N-[5-(cis-3,5-Dimethyl-1-piperazinyl)-2-(methyloxy)phenyl]-6-(2-furanyl)-3-pyridinesulfonamide
N-[5-(cis-3,5-Dimethyl-1-piperazinyl)-2-(methyloxy)phenyl]-6-(2-thienyl)-3-pyridinesulfonamide
N-[5-(cis-3,5-Dimethyl-1-piperazinyl)-2-(methyloxy)phenyl]-6-(5-methyl-2-furanyl)-3-pyridinesulfonamide
N-[5-(cis-3,5-Dimethyl-1-piperazinyl)-2-(methyloxy)phenyl]-6-(4-methyl-2-thienyl)-3-pyridinesulfonamide
N-[5-(cis-3,5-Dimethyl-1-piperazinyl)-2-(methyloxy)phenyl]-5-(5-methyl-2-furanyl)-2-pyridinesulfonamide
N-[2-(Methyloxy)-5-(cis-3,5-trimethyl-1-piperazinyl)phenyl]-4-(2-thienyl)benzenesulfonamide
2-Chloro-N-[5-(cis-3,5-dimethyl-1-piperazinyl)-2-(methyloxy)phenyl]-4-(3-thienyl)benzenesulfonamide
2-Chloro-N-[5-(cis-3,5-dimethyl-1-piperazinyl)-2-(methyloxy)phenyl]-4-(5-methyl-2-thienyl)benzenesulfonamide
N-[5-(cis-3,5-Dimethyl-1-piperazinyl)-2-(methyloxy)phenyl]-3-(2-furanyl)benzenesulfonamide
N-[5-(cis-3,5-Dimethyl-1-piperazinyl)-2-(methyloxy)phenyl]-3-(3-furanyl)benzenesulfonamide
N-[5-(cis-3,5-Dimethyl-1-piperazinyl)-2-(methyloxy)phenyl]-3-(4-methyl-2-thienyl)benzenesulfonamide
N-[5-(cis-3,5-Dimethyl-1-piperazinyl)-2-(methyloxy)phenyl]-3-methyl-4-(5-methyl-2-thienyl)benzenesulfonamide
N-[3-(cis-3,5-Dimethyl-1-piperazinyl)phenyl]-2-(methyloxy)-4-(4-methyl-2-thienyl)benzenesulfonamide
N-[3-(cis-3,5-Dimethyl-1-piperazinyl)phenyl]-4-(2-furanyl)-2-(methyloxy)benzenesulfonamide
N-[3-(cis-3,5-Dimethyl-1-piperazinyl)phenyl]-2-(methyloxy)-4-(2-thienyl)benzenesulfonamide
N-[5-(cis-3,5-Dimethyl-1-piperazinyl)-2-(methyloxy)phenyl]-2-methyl-4-(3-thienyl)benzenesulfonamide
N-[5-(cis-3,5-Dimethyl-1-piperazinyl)-2-(methyloxy)phenyl]-2-fluoro-4-(5-methyl-2-thienyl)benzenesulfonamide
N-[5-(cis-3,5-Dimethyl-1-piperazinyl)-2-(methyloxy)phenyl]-2,5-difluoro-4-(4-methyl-2-thienyl)benzenesulfonamide
N-[5-(cis-3,5-Dimethyl-1-piperazinyl)-2-(methyloxy)phenyl]-2-methyl-4-(5-methyl-2-thienyl)benzenesulfonamide
N-[5-(cis-3,5-Dimethyl-1-piperazinyl)-2-(methyloxy)phenyl]-3-fluoro-4-(3-thienyl)benzenesulfonamide
N-[5-(cis-3,5-Dimethyl-1-piperazinyl)-2-(methyloxy)phenyl]-3-fluoro-4-(5-methyl-2-thienyl)benzenesulfonamide
N-[5-(cis-3,5-Dimethyl-1-piperazinyl)-2-(methyloxy)phenyl]-2,5-difluoro-4-(2-furanyl)benzenesulfonamide
N-[5-(cis-3,5-Dimethyl-1-piperazinyl)-2-(methyloxy)phenyl]-5-(3-pyridinyl)-2-thiophenesulfonamide
N-[3-(cis-3,5-Dimethyl-1-piperazinyl)-4-(methyloxy)phenyl]-2'-methyl-4-biphenylsulfonamide
N-[3-(cis-3,5-Dimethyl-1-piperazinyl)-4-(methyloxy)phenyl]-5-(4-fluorophenyl)-2-thiophenesulfonamide
N-[5-(cis-3,5-Dimethyl-1-piperazinyl)-2-(methyloxy)phenyl]-2',4'-difluoro-4-biphenylsulfonamide
N-[5-(cis-3,5-Dimethyl-1-piperazinyl)-2-(methyloxy)phenyl]-3',4'-difluoro-4-biphenylsulfonamide
N-[2-Chloro-5-(cis-3,5-dimethyl-1-piperazinyl)phenyl]-4-(2-furanyl)benzenesulfonamide
N-[2-Chloro-5-(cis-3,5-dimethyl-1-piperazinyl)phenyl]-5-(2-fluorophenyl)-2-thiophenesulfonamide
N-[5-(cis-3,5-Dimethyl-1-piperazinyl)-2-(methyloxy)phenyl]-3-fluoro-4-(5-methyl-3-thienyl)benzenesulfonamide
N-[5-(cis-3,5-Dimethyl-1-piperazinyl)-2-(methyloxy)phenyl]-3-fluoro-4-(5-methyl-3-thienyl)benzenesulfonamide
N-[5-(cis-3,5-Dimethyl-1-piperazinyl)-2-(methyloxy)phenyl]-4-(5-methyl-3-thienyl)benzenesulfonamide
2-Chloro-N-[5-(cis-3,5-dimethyl-1-piperazinyl)-2-(methyloxy)phenyl]-4-(5-methyl-3-thienyl)benzenesulfonamide
N-[5-(cis-3,5-Dimethyl-1-piperazinyl)-2-(methyloxy)phenyl]-7-(2-furanyl)-2,1,3-benzoxadiazole-4-sulfonamide
2-Chloro-N-[5-(cis-3,5-dimethyl-1-piperazinyl)-2-(methyloxy)phenyl]-4-(5-methyl-2-furanyl)benzenesulfonamide
N-[5-(cis-3,5-Dimethyl-1-piperazinyl)-2-(methyloxy)phenyl]-3-fluoro-4-(2-furanyl)benzenesulfonamide
2-Chloro-N-[5-(cis-3,5-dimethyl-1-piperazinyl)-2-(methyloxy)phenyl]-4-(2-furanyl)benzenesulfonamide
N-[5-(cis-3,5-Dimethyl-1-piperazinyl)-2-(methyloxy)phenyl]-2-fluoro-4-(5-methyl-2-furanyl)benzenesulfonamide
N-[3-(cis-3,5-Dimethyl-1-piperazinyl)-4-(ethyloxy)phenyl]-4-(2-thienyl)benzenesulfonamide
N-{2-(Methyloxy)-5-[(3S)-3-methyl-1-piperazinyl]phenyl}-4-(2-thienyl)benzenesulfonamide
N-{2-(Methyloxy)-5-[(3R)-3-methyl-1-piperazinyl]phenyl}-4-(2-thienyl)benzenesulfonamide
N-[5-(cis-3,5-Dimethyl-1-piperazinyl)-2-hydroxyphenyl]-4-(5-methyl-2-furanyl)benzenesulfonamide
N-[5-(cis-3,5-Dimethyl-1-piperazinyl)-2-hydroxyphenyl]-4-(2-furanyl)benzenesulfonamide
N-[5-(cis-3,5-Dimethyl-1-piperazinyl)-2-hydroxyphenyl]-3-fluoro-4-(5-methyl-2-furanyl)benzenesulfonamide
N-[5-(cis-3,5-Dimethyl-1-piperazinyl)-2-hydroxyphenyl]-5-(2-fluorophenyl)-2-thiophenesulfonamide and
N-[5-(cis-3,5-Dimethyl-1-piperazinyl)-2-(methyloxy)phenyl]-4-[(phenylmethyl)oxy]benzenesulfonamide.

10. A process for the preparation of a compound according to claim 1 comprising (i) coupling a compound of formula (II)

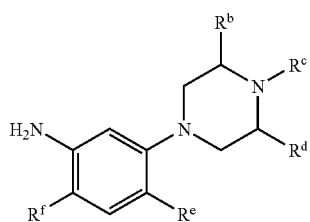

(II)

wherein $R^b$, $R^c$, $R^d$, $R^e$ and $R^f$ are as defined in claim 1 or protected derivatives thereof, with a compound of formula (III) wherein $R^a$ and Y are as defined in claim 1 and $L^1$ is a suitable leaving group

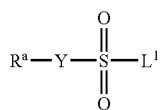

(III)

or (ii) by interconversion of compounds of claim 1 to other compounds of claim 1.

11. A pharmaceutical composition comprising a compound according to claim 1.

12. A method of treatment for conditions or disorders which can be mediated via the growth hormone secretagogue (GHS) receptors comprising the administration of an effective amount of a compound of claim 1 to a mammal, wherein the condition or disorder is selected from the group consisting of cachexia, sarcopenia, osteoporosis, rheumatoid arthritis, osteoarthritis, growth hormone deficiency, congestive heart failure, symptoms associated with gastro-esophageal reflux, symptoms associated with dyspepsia, symptoms associated with appetite-related cachexia, symptoms associated with metabolic-related cachexia, treatments of paralytic lieus, treatments of pseudo-obstruction, conditions associated with constipation, and constipation-predominant irritable bowel syndrome.

13. The method of claim 12 wherein said mammal is a human.

* * * * *